US011806246B2

(12) United States Patent
Altarac et al.

(10) Patent No.: US 11,806,246 B2
(45) Date of Patent: Nov. 7, 2023

(54) EXPANDABLE INTERBODY SPACER

(71) Applicant: Neurostructures, Inc., Irvine, CA (US)

(72) Inventors: Moti Altarac, Irvine, CA (US); Joey Reglos, Dumaguete (PH)

(*) Notice: Subject to any disclaimer, the term of this patent is extended or adjusted under 35 U.S.C. 154(b) by 0 days.

(21) Appl. No.: 17/862,232

(22) Filed: Jul. 11, 2022

(65) Prior Publication Data

US 2022/0346967 A1 Nov. 3, 2022

Related U.S. Application Data

(63) Continuation of application No. 16/846,324, filed on Apr. 11, 2020, now Pat. No. 11,382,761.

(51) Int. Cl.
*A61F 2/44* (2006.01)
*A61F 2/30* (2006.01)

(52) U.S. Cl.
CPC .............. *A61F 2/442* (2013.01); *A61F 2/447* (2013.01); *A61F 2/4465* (2013.01); *A61F 2002/30507* (2013.01); *A61F 2002/30579* (2013.01); *A61F 2002/30593* (2013.01); *A61F 2002/30904* (2013.01); *A61F 2230/0013* (2013.01)

(58) Field of Classification Search
CPC ........ A61F 2/442; A61F 2/447; A61F 2/4465; A61F 2/44; A61F 2002/30507; A61F 2002/30579; A61F 2002/30593; A61F 2002/30904; A61F 2230/0013

USPC ............................................ 623/17.11–17.16
See application file for complete search history.

(56) References Cited

U.S. PATENT DOCUMENTS

| 8,062,375 | B2 * | 11/2011 | Glerum | A61F 2/4611 |
| | | | | 623/17.16 |
| 8,518,120 | B2 * | 8/2013 | Glerum | A61F 2/447 |
| | | | | 623/17.16 |
| 11,382,761 | B2 * | 7/2022 | Altarac | A61F 2/4637 |
| 2018/0185163 | A1 * | 7/2018 | Weiman | A61F 2/442 |
| 2019/0000643 | A1 * | 1/2019 | Weiman | A61F 2/4455 |
| | | | | 623/17.16 |

* cited by examiner

*Primary Examiner* — Jessica Weiss
(74) *Attorney, Agent, or Firm* — Rimas T. Lukas

(57) ABSTRACT

An expandable interbody spacer for the spine is provided. The interbody spacer includes a housing, a top endplate and a bottom endplate. An actuator is located inside the housing between the top and bottom endplates. A locking screw is configured to drive the actuator and move the endplates between collapsed and expanded configurations. Variations of the expandable spacer are provided in which the endplates move bilaterally outwardly into uniform and parallel expansion along the latitudinal axis, the endplates angulate about a pivot point along a longitudinal axis such that the distal end of the spacer increases in height relative to the proximal end, and the endplates angulate about a pivot along a lateral axis such that the height along one lateral side of the spacer increases in height relative to the other lateral side.

20 Claims, 39 Drawing Sheets

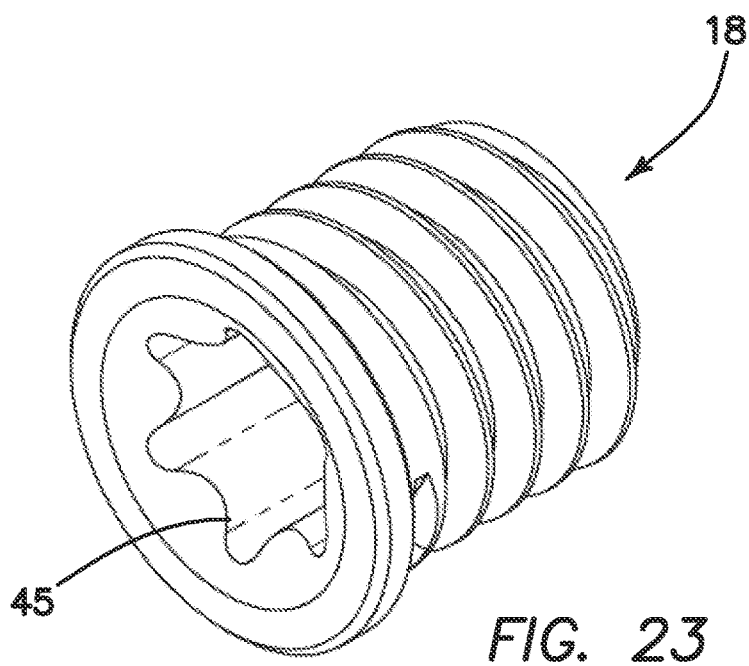
FIG. 23
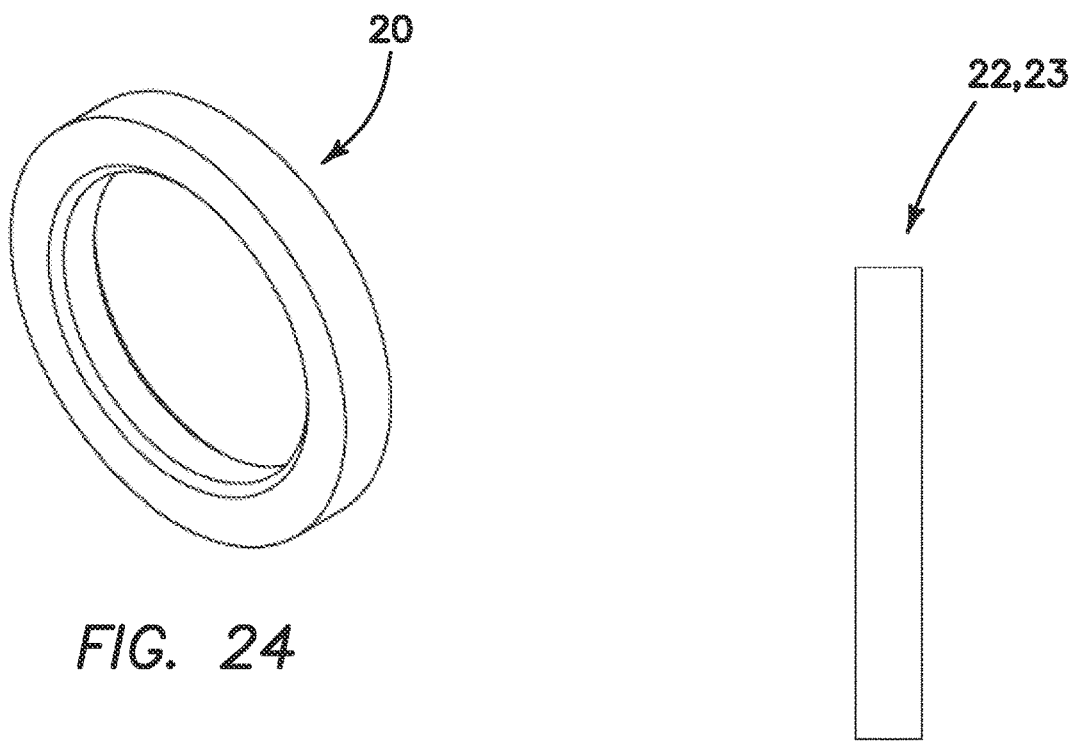
FIG. 24
FIG. 25

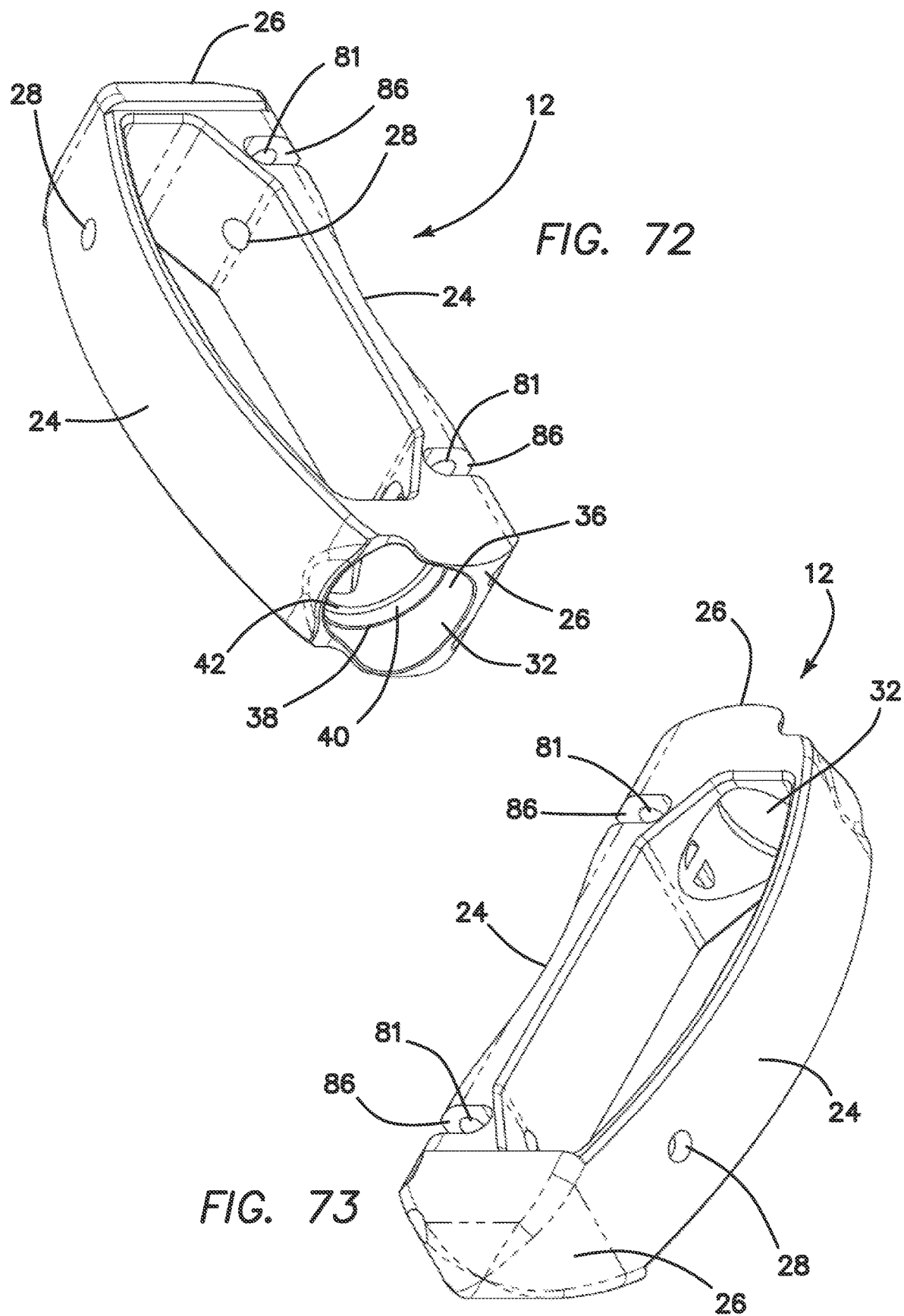

EXPANDABLE INTERBODY SPACER

CROSS-REFERENCE TO RELATED APPLICATION

This application is a continuation of U.S. patent application Ser. No. 16/846,324 filed on Apr. 11, 2020, entitled "Expandable interbody spacer" now issued as U.S. Pat. No. 11,382,761 incorporated herein by reference in its entirety

FIELD OF THE INVENTION

This application relates generally to spinal implants, and in particular, expandable intervertebral spacers and fusion cages.

BACKGROUND OF THE INVENTION

Back pain can be caused by a variety of factors including but not limited to the rupture or degeneration of one or more intervertebral discs due to degenerative disc disease, spondylolisthesis, deformative disorders, trauma, tumors and the like. In such cases, pain typically results from compression or irritation of spinal nerve roots arising from reduced spacing between adjacent vertebrae, a damaged disc and or misalignment of the spine resulting from the injury or degeneration.

Common forms of treating such pain include various types of surgical procedures in which a damaged disc may be partially or totally excised. After the disc space is prepared, one or more implants are inserted between the adjacent vertebrae in an effort to restore the natural spacing and alignment between the vertebrae, so as to relieve the compression, irritation or pressure on the spinal nerve or nerves and, thereby, eliminate or significantly reduce the pain that the patient is experiencing. Typically, one or more implants are used together with substances that encourage bone ingrowth to facilitate fusion between adjacent vertebrae and achieve immobilization of adjacent bones. Surgeons insert these intervertebral devices to adjunctively facilitate bone fusion in between and into the contiguous involved vertebrae. This fusion creates a new solid bone mass and provides weight bearing support between adjacent vertebral bodies which acts to hold the spinal segment at an appropriate biomechanically restored height as well as to stop motion in a segment of the spine and alleviate pain.

In a posterior lumbar interbody fusion (PLIF) surgery, spinal fusion is achieved in the lower back by inserting an implant such as a cage and typically graft material to encourage bone ingrowth directly into the disc space between adjacent vertebrae. The surgical approach for PLIF is from the back of the patient, posterior to the spinal column. An anterior lumbar interbody fusion (ALIF) surgical procedure is similar to the PLIF procedure except that in the ALIF procedure, the disc space is fused by approaching the spine through the abdomen from an anterior approach instead of from a posterior approach. Another fusion procedure is called a transforaminal lumbar interbody fusion (TLIF) which involves a posterior and lateral approach to the disc space. To gain access to the disc space, the facet joint may be removed whereby access is gained via the nerve foramen. In an extreme lateral interbody fusion (XLIF), the disc space is accessed from small incisions on the patient's side.

In the typical procedures described above, the adjacent vertebrae must be distracted apart by a substantial amount in order to allow the surgeon to advance the implant with relatively little resistance along the delivery path. Also, the surgeon must typically release the implant at least once as the implant is being delivered along the delivery path and align and position the implant at the target position of implantation, typically in the anterior aspect of the disc space. If static spacers having a fixed height are employed, the right-sized spacer is selected from a plurality of spacers. Sometimes the selected static spacer must be interchanged for one of a different height during the procedure. Expandable spacers provide several advantages over static spacers. For example, expandable spacers may be more easily inserted in their low-profile configuration and then mechanically expanded into their high-profile configuration when in the right position. Another advantage of some expandable spacers is that the degree of expansion easily can be adjusted in-situ according to the specific anatomy of the patient. Generally, expandable spacers avoid the need to stock multiple sizes, and to remove and replace spacers during the procedure.

One disadvantage of expandable spacers is that they typically increase in length or other lateral dimension when expanded into their high-profile configuration. This increase in length creates a larger footprint or axial projection for the spacer which may require removal of more of the existing disc. Furthermore, the spacer may have to be repositioned to accommodate the increased length in order to achieve proper positioning and avoid neural impingement. Therefore, there is a need to provide a new and improved expandable interbody spacer that is easy to position, deploy from a low-profile to a high-profile configuration, withstand high anatomical forces and that does not increase in length when moved into its high-profile configuration. This invention, as described in the detailed description, sets forth an improved interbody spacer that meets these needs.

SUMMARY OF THE INVENTION

According to one aspect of the invention, an expandable interbody spacer for the spine is provided. The expandable interbody spacer includes a housing having two sides interconnected by a distal endwall and a proximal endwall. The housing defines a hollow interior. The proximal endwall has a rear opening. The spacer includes a top endplate and a bottom endplate each having a bone-engaging surface and an interior surface opposite to the bone-engaging surface. The interior surface has at least one mating surface. The spacer includes an actuator located within the interior of the housing and between the interior surfaces of the top endplate and bottom endplate. The actuator has a top wall and a bottom wall interconnected by a distal wall and a proximal wall and a first sidewall and a second sidewall. The actuator has at least one driving surface formed in the first sidewall and at least one driving surface formed in the second sidewall sized and configured to engage the mating surfaces of the top and bottom endplates. The actuator includes a threaded opening formed in the proximal wall that is aligned with the rear opening of the housing. A locking screw is provided that is threadingly connected to the threaded opening of the actuator. The locking screw is also connected to the housing such that the locking screw does not translate longitudinally relative to the housing. The locking screw is configured such that rotation of the locking screw in a first direction translates the actuator in a proximal direction relative to the housing and moves the top endplate and the bottom endplate outwardly from a low-profile configuration into a high-profile configuration wherein the distance between the top endplate and bottom endplate is greater in the high-profile configuration.

According to another aspect of the invention, an expandable interbody spacer for the spine is provided. The expandable interbody spacer includes a housing having a first longitudinal sidewall oppositely disposed from a second longitudinal sidewall interconnected by a distal endwall and a proximal endwall defining a hollow interior. The proximal endwall has a rear opening. The housing includes at least one pivot pin aperture formed in the first longitudinal sidewall and extending longitudinally adjacent to a top end and at least one pivot pin aperture formed in the first longitudinal sidewall and extending longitudinally adjacent to a bottom end. A top endplate and a bottom endplate are provided. Each endplate has a bone-engaging surface and an interior surface opposite to the bone-engaging surface. The interior surface has at least two eyelets adjacent a first longitudinal side and at least two protrusions adjacent a second longitudinal side. Each eyelet defines a pivot pin opening that is sized and configured to receive a pivot pin. The top endplate is pivotably connected to the housing by at least one pivot pin located in the pivot pin openings of the top endplate and the at least one pivot pin aperture adjacent to the top end of the housing. The bottom endplate is pivotably connected to the housing by at least one pivot pin located in the pivot pin openings of the bottom endplate and in the at least one pivot pin aperture adjacent to the bottom end of the housing. The expandable spacer includes an actuator located within the interior of the housing and between the interior surfaces of the top endplate and bottom endplate. The actuator has a proximal end and a distal end and a top wall and a bottom wall interconnected by a distal wall and a proximal wall and a first longitudinal sidewall and a second longitudinal sidewall. The top wall of the actuator has at least two driving surfaces along the second longitudinal sidewall sized and configured to engage the at least two protrusions of the top endplate. The bottom wall of the actuator has at least two driving surfaces along the second longitudinal sidewall sized and configured to engage the at least two protrusions of the bottom endplate. The actuator has a threaded opening formed in the proximal wall that is aligned with the rear opening of the housing. A locking screw is threadingly connected to the threaded opening of the actuator and also connected to the housing such that the locking screw does not translate longitudinally relative to the housing when rotated. Rotation of the locking screw in a first direction translates the actuator in a proximal direction relative to the housing and angulates the top and bottom endplates about the pivot pins from a low-profile configuration to a high-profile configuration wherein the distance between the upper and lower endplates adjacent the second sidewall is greater than the distance between the upper and lower endplates adjacent the first sidewall when the spacer is in the high-profile configuration.

According to another aspect of the invention, an expandable interbody spacer for the spine is provided. The expandable interbody spacer includes a housing having a first longitudinal sidewall and a second longitudinal sidewall interconnected by a distal endwall and a proximal endwall defining a hollow interior. The proximal endwall has a rear opening. The expandable spacer includes a top endplate and a bottom endplate each having a bone-engaging surface and an interior surface opposite to the bone-engaging surface. The interior surface has at least one mating surface extending from the interior surface. The expandable interbody spacer includes an actuator located within the interior of the housing and between the interior surfaces of the top endplate and bottom endplate. The actuator has a proximal end and a distal end, a top wall and a bottom wall interconnected by a front wall and a back wall and a first longitudinal sidewall and a second longitudinal sidewall. The actuator has at least one driving surface dimensioned to engage the mating surface of top endplate and at least one driving surface dimensioned to engage the mating surface of the bottom endplate. The actuator has a threaded opening formed in the back wall and aligned with the rear opening of the housing. The top and bottom endplates are connected to either one of the actuator or housing such that the top and bottom endplates are movable between a low-profile configuration and a high-profile wherein the distance between the endplates is greater in the high-profile configuration relative to the low-profile configuration. The spacer includes a locking screw threadingly engaged within the threaded opening of the actuator. Rotation of the locking screw moves the endplates between the low-profile configuration and the high-profile configuration. The locking screw does not translate with respect to housing when the locking screw is rotated.

BRIEF DESCRIPTION OF THE DRAWINGS

FIG. 23 is a top perspective rear view of a locking screw of an expandable interbody spacer according to the present invention.

FIG. 24 is a top perspective view of a locking ring of an expandable interbody spacer according to the present invention.

FIG. 25 is a top perspective view of an alignment pin of an expandable interbody spacer according to the present invention.

FIG. 72 is a rear top perspective view of a housing of the expandable interbody spacer of FIG. 60.

FIG. 73 is a front top perspective view of the housing of FIG. 72.

DETAILED DESCRIPTION OF THE INVENTION

Figure 1:
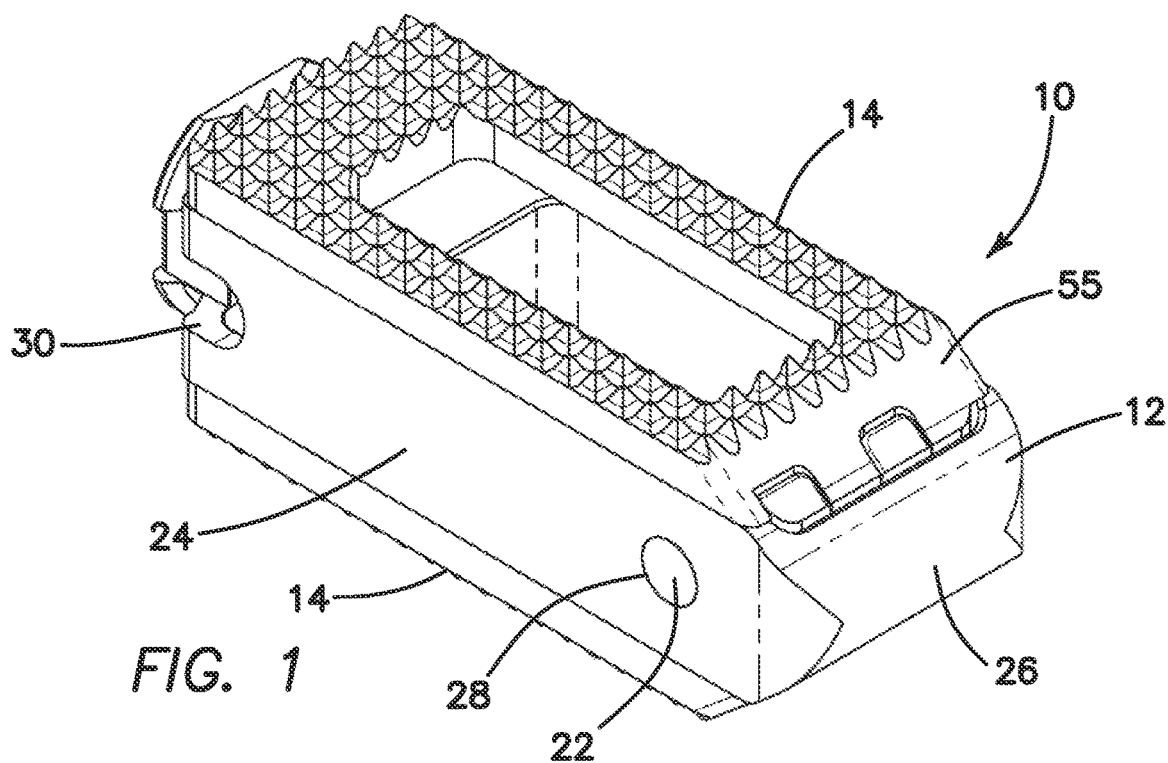
FIG. 1 is a front top perspective view of an expandable interbody spacer in its low-profile configuration according to the present invention.
Figure 2:
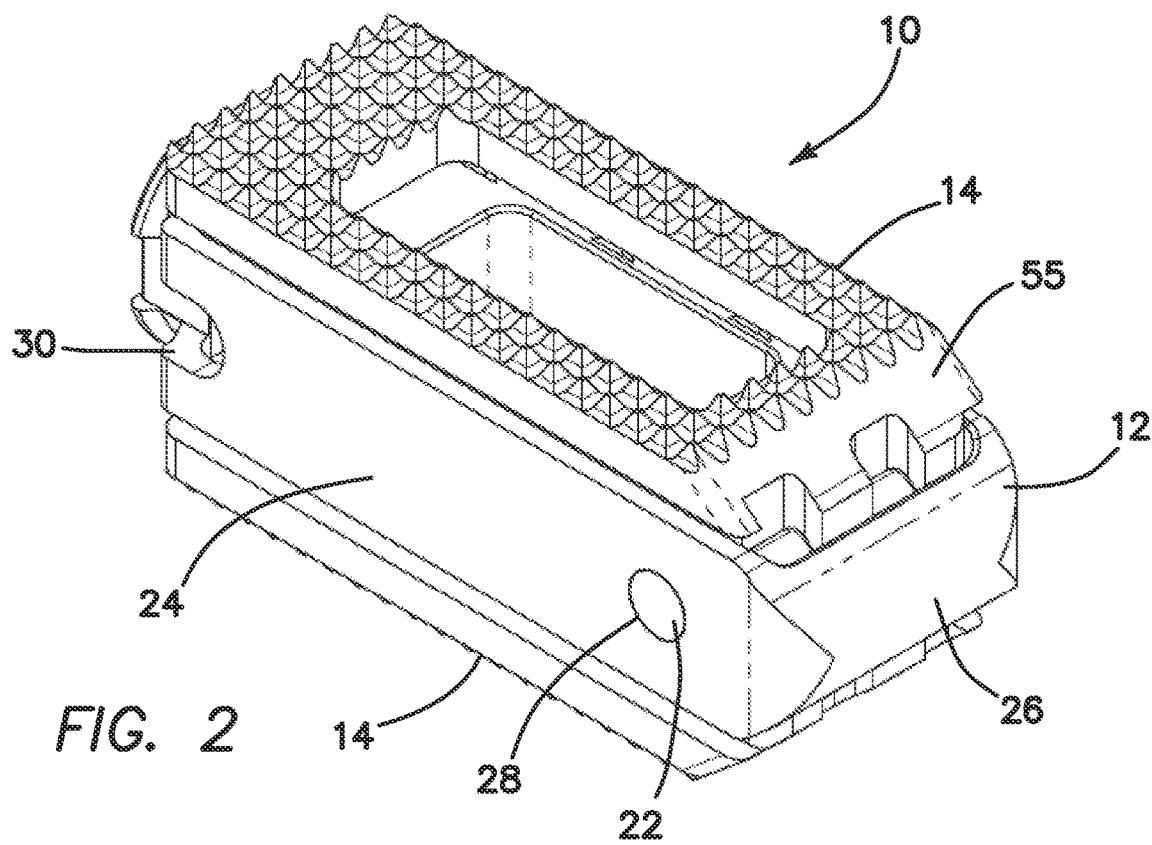
FIG. 2 is a front top perspective view of the expandable interbody spacer of FIG. 1 in its high-profile configuration.
Figure 3:
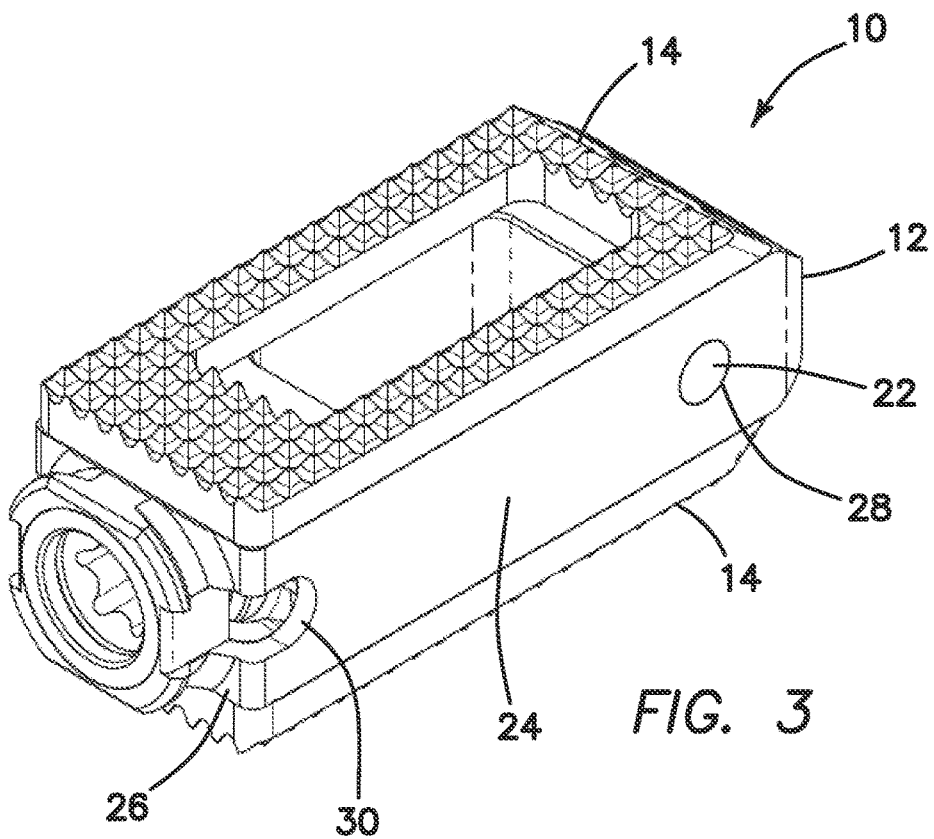
FIG. 3 is a rear top perspective view of the expandable interbody spacer of FIG. 1.
Figure 4:
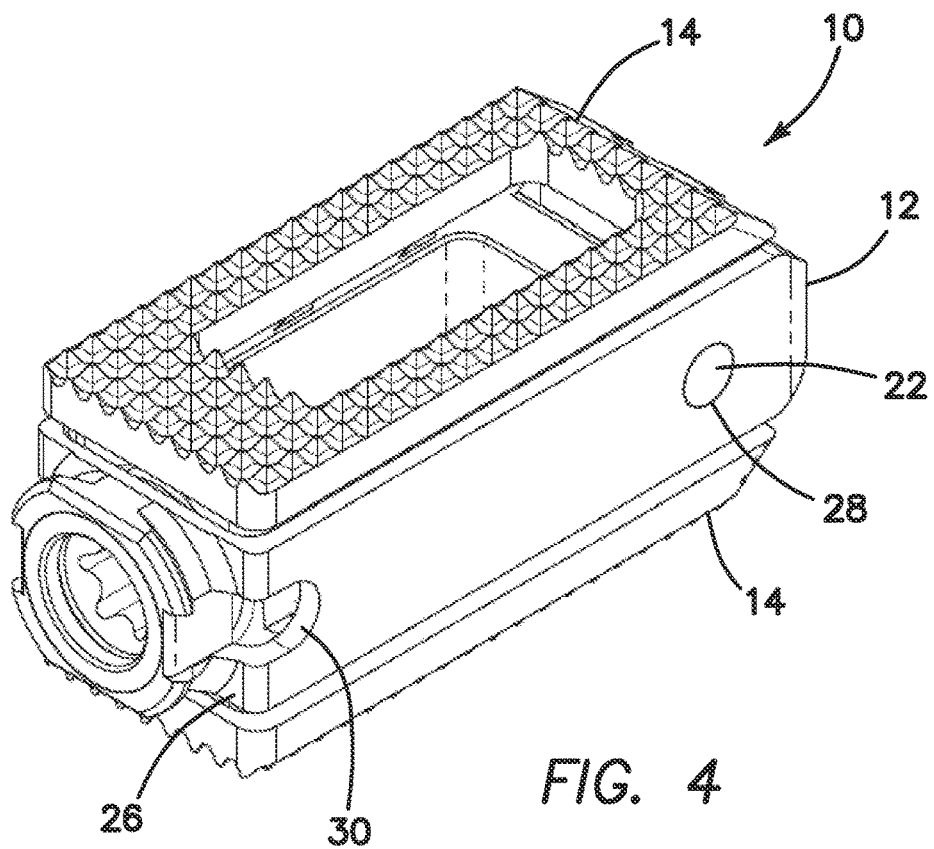
FIG. 4 is a rear top perspective view of the expandable interbody spacer of FIG. 2.
Figure 5:
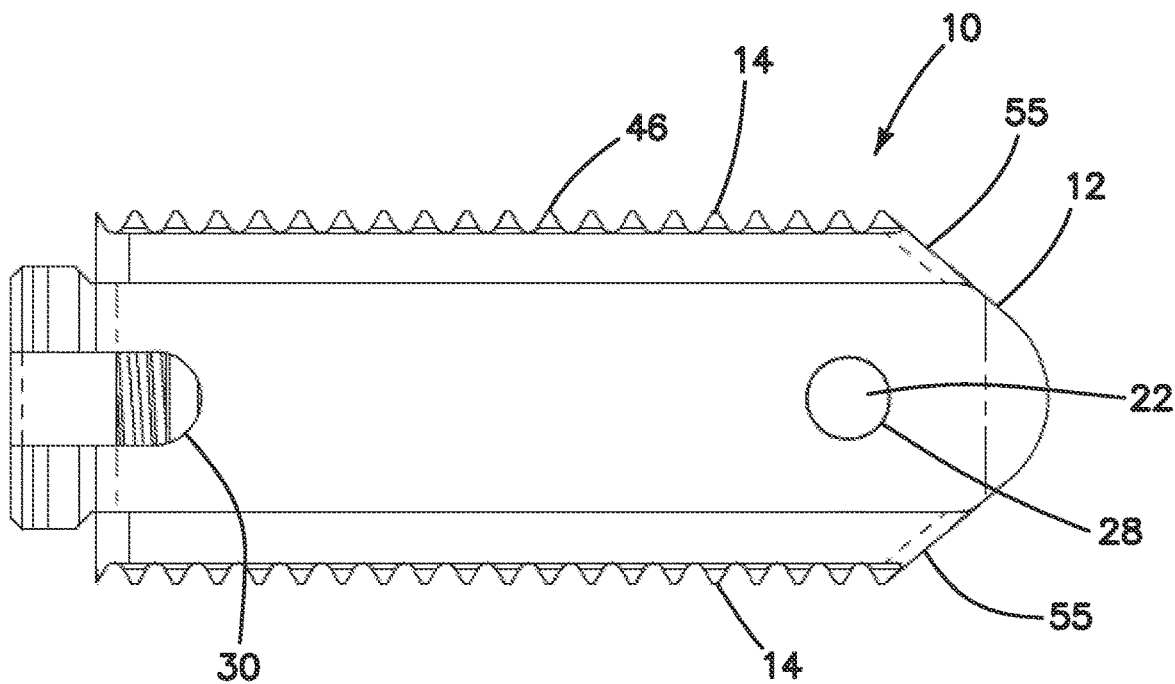
FIG. 5 is a side elevational view of the expandable interbody spacer of FIG. 1.

Variations of expandable interbody spacers are described below. FIGS. 1-25 depict one variation of an expandable interbody spacer 10 typically used to stabilize or fuse vertebral bodies in the lumbar or other region of the spine. The expandable interbody spacer 10 comprises a housing 12, upper and lower endplates 14, an actuator 16 located inside the housing 12 and between the upper and lower endplates 14, a locking screw 18 connected to the housing 12 by a locking ring 20 and configured to move the actuator 16, and an alignment pin 22 connected to the housing 12 to guide the actuator 16 and keep it aligned. The expandable interbody spacer 10 is insertable into the disc space between two adjacent vertebral bodies from a posterior approach while in an unexpanded state illustrated in FIGS. 1, 3, 5, 7, 9, 11 and 13. Once inserted and properly positioned inside the disc space, both upper and lower endplates 14 are expanded uniformly in height in a parallel fashion on both sides of the implant. Expansion is effected by rotating the locking screw 18 with an instrument by the surgeon. Rotation of the locking screw 18 moves the actuator which in turn moves the endplates 14 simultaneously into the expanded state illustrated in FIGS. 2, 4, 6, 8, 10, 12 and 14. The expandable interbody spacer 10 is advantageously easier to implant and does not require a stock of multiple implants of different sizes.

Figure 15:
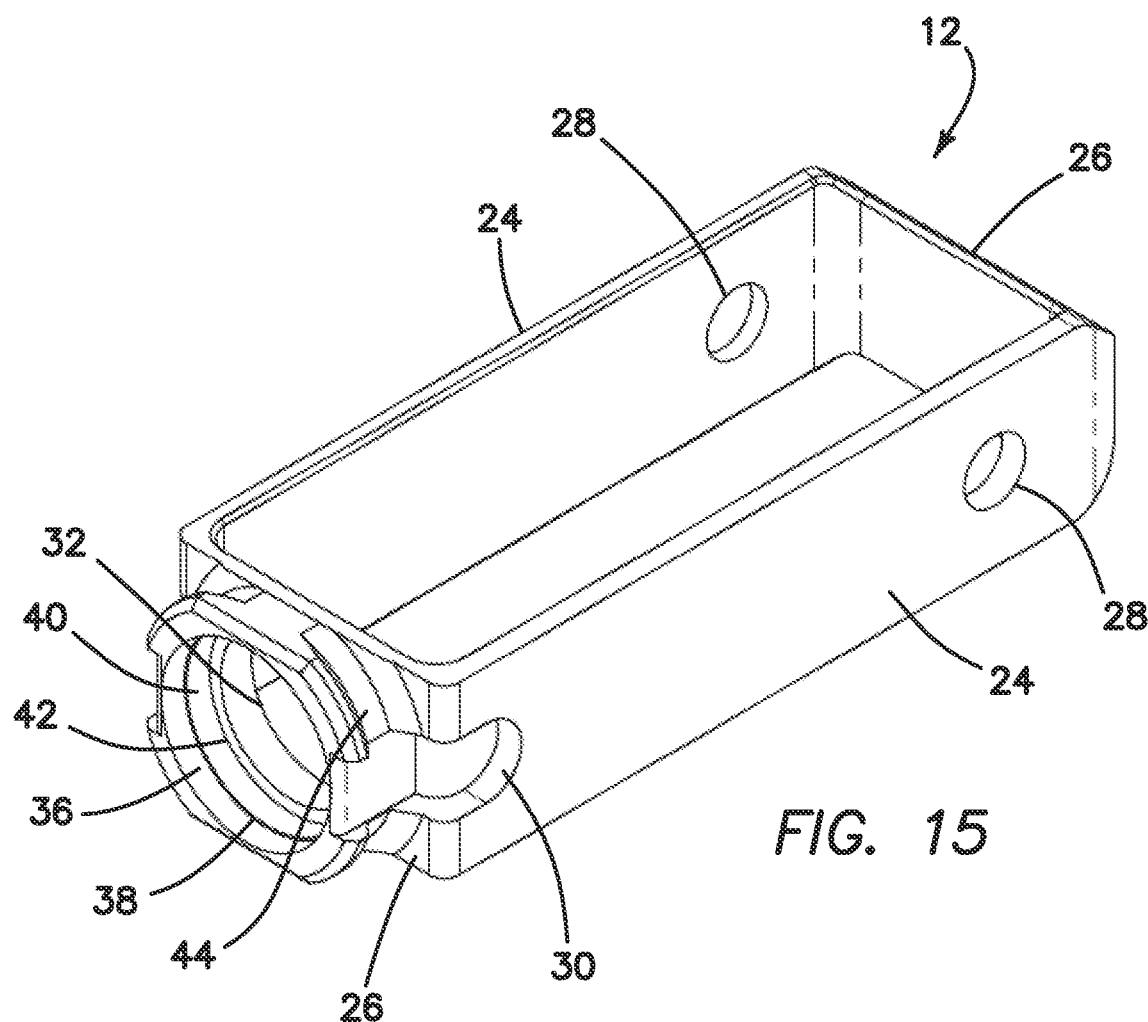
FIG. 15 is a top perspective view of a housing of an expandable interbody spacer according to the present invention.
Figure 16:
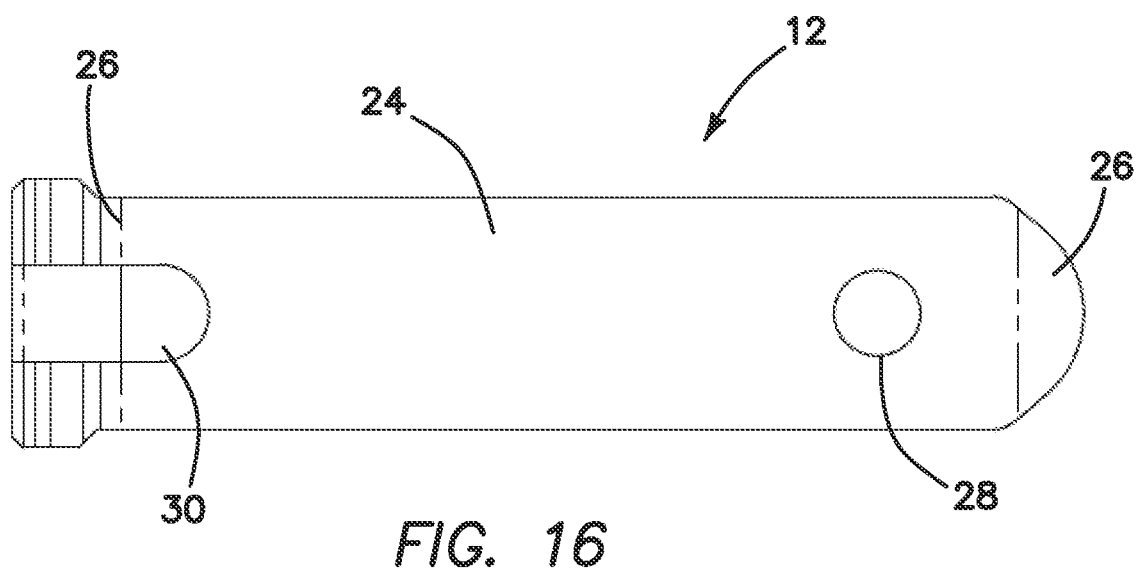
FIG. 16 is a side elevational view of the housing of FIG. 15.

Turning now to the FIGS. 15-16, the housing 12 will now be described in greater detail. The housing 12 includes two opposite sidewalls 24 interconnected by two opposite endwalls 26 that together define an interior of the housing 12. Each of the two sidewalls 24 include an aperture 28 oppositely disposed from each other and near the distal end of the housing 12 and sized and configured for receiving the alignment pin 22 of FIG. 25. At the proximal end of the housing 12, the sidewalls 24 include oppositely disposed instrument notches 30 which serve as openings sized and configured to receive oppositely disposed distal prongs of an insertion instrument used for delivering, implanting, deploying and removing the interbody spacer 10. As shown in FIGS. 15-16, the sidewalls 24 are parallel to each other and of equal length. Also, the endwalls 26 are parallel to each other and of equal length. Both the sidewalls and endwalls 26 define a rectangular shaped housing 12 having an open top end and open bottom end. The top end and the bottom end are parallel to each other and the housing 12 has a constant height. The front distal endwall 26 is curved, tapered, angled or peaked to define a leading ramp-like surface for easily penetrating into the disc space. The rear endwall 26 includes a cylindrical-like collar 34 extending proximally and defining a rear opening 32 that opens to the interior of the housing 12. The rear opening 32 is configured for accessing the proximal end of the locking screw 18 of FIG. 23 that is connected to the housing 12 in the location of the collar 34. The proximal end of the locking screw 18 is provided with an instrument-engaging socket 45. With particular reference to FIG. 15, the inner surface of the collar 34 defines a first recess 36 for receiving the locking ring 20 of FIG. 24. The first recess 36 may include a first ledge 38 to provide a stop for the locking ring 20 when connected to the collar 34. The inner surface of the collar 34 also includes a second recess 40. The second recess 40 is sized and configured to receive the proximal end of the locking screw 18. The second recess 40 may include a second ledge 42 such that the proximal end of the locking screw 18 is retained in the second recess 40 between the second ledge 42 at the distal end and first ledge 38 and the locking ring 20 at the proximal end such that the locking screw 18 is permitted to rotate with respect to the housing 12 without translating with respect to the housing 12 or falling out of the housing 12. Furthermore, the outer surface of the collar 34 includes oppositely disposed lateral flats for providing easy and direct access for an insertion instrument for connected to the adjacent instrument notches 30. Top and bottom flats are also provided to give the collar 34 a low-profile height equal to the height of the housing 12. The outer surface of the collar 34 includes a ring-shaped outer recess 44.

Figure 17:
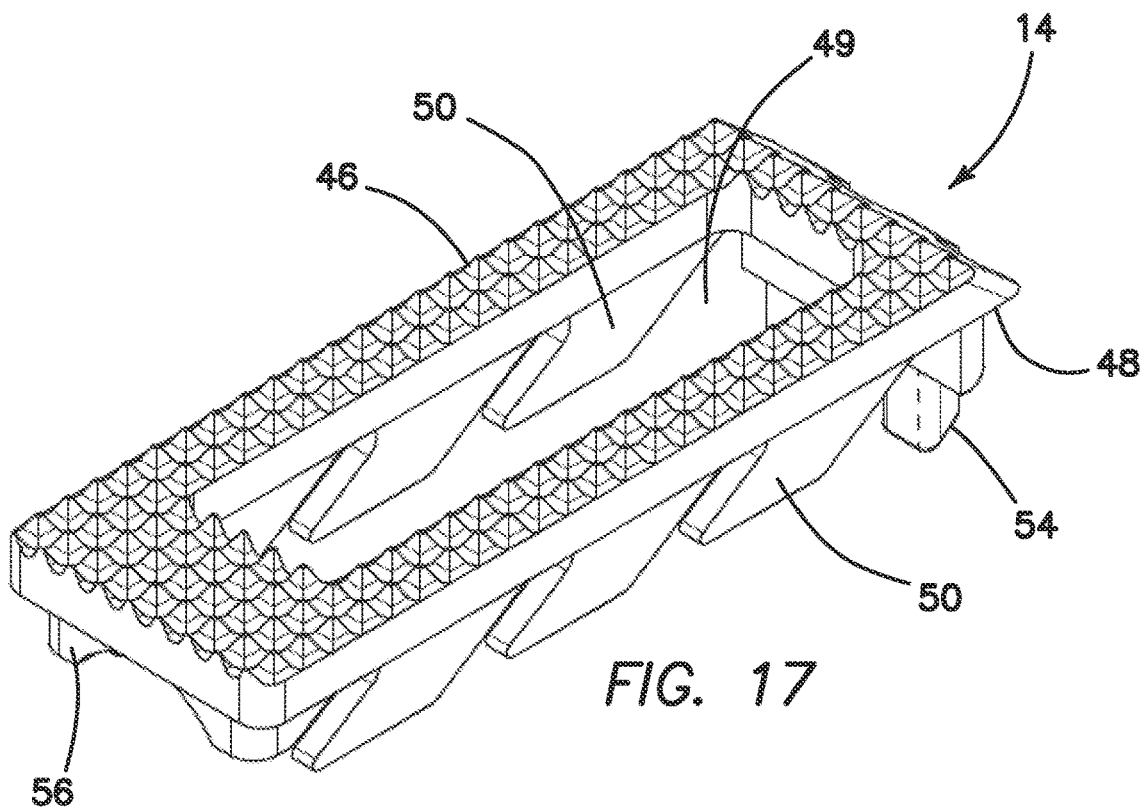
FIG. 17 is a rear top perspective view of an endplate of an expandable interbody spacer according to the present invention.
Figure 18:
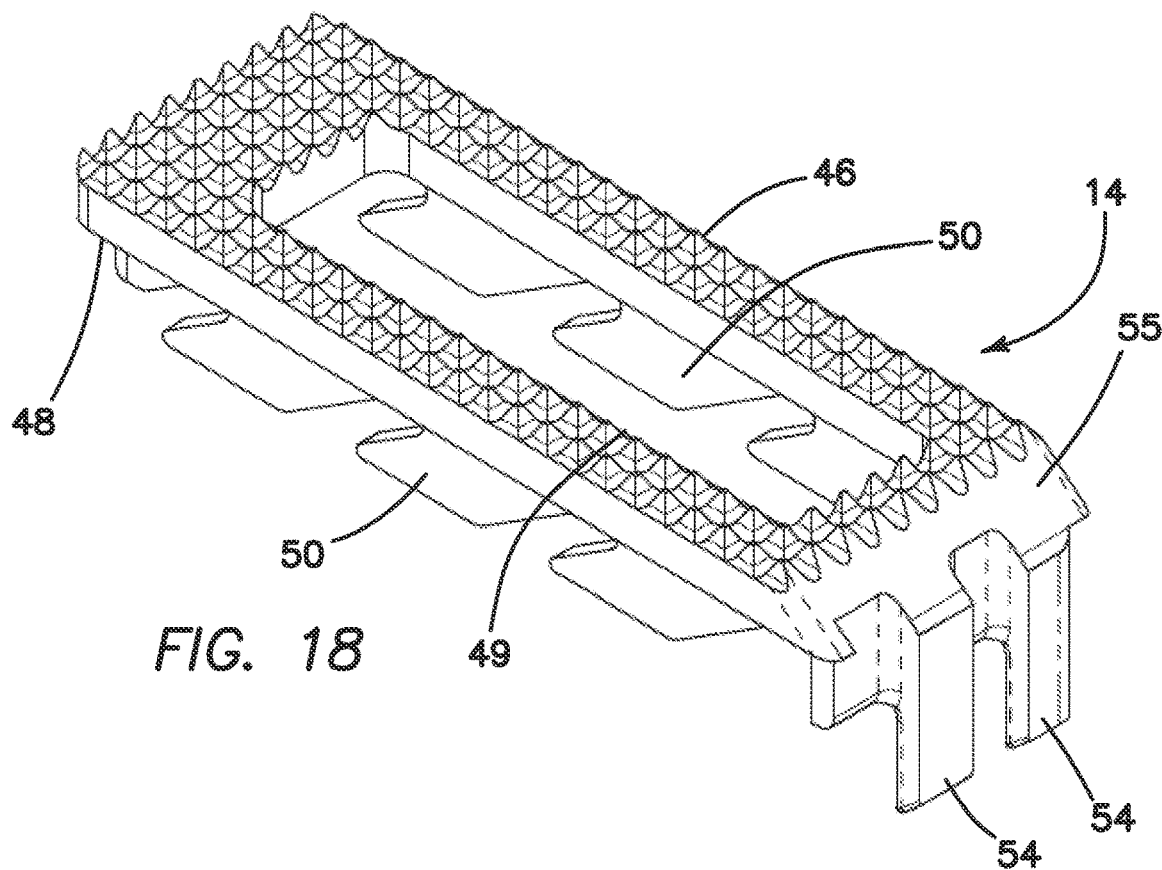
FIG. 18 is a front top perspective view of the endplate of FIG. 17.
Figure 19:
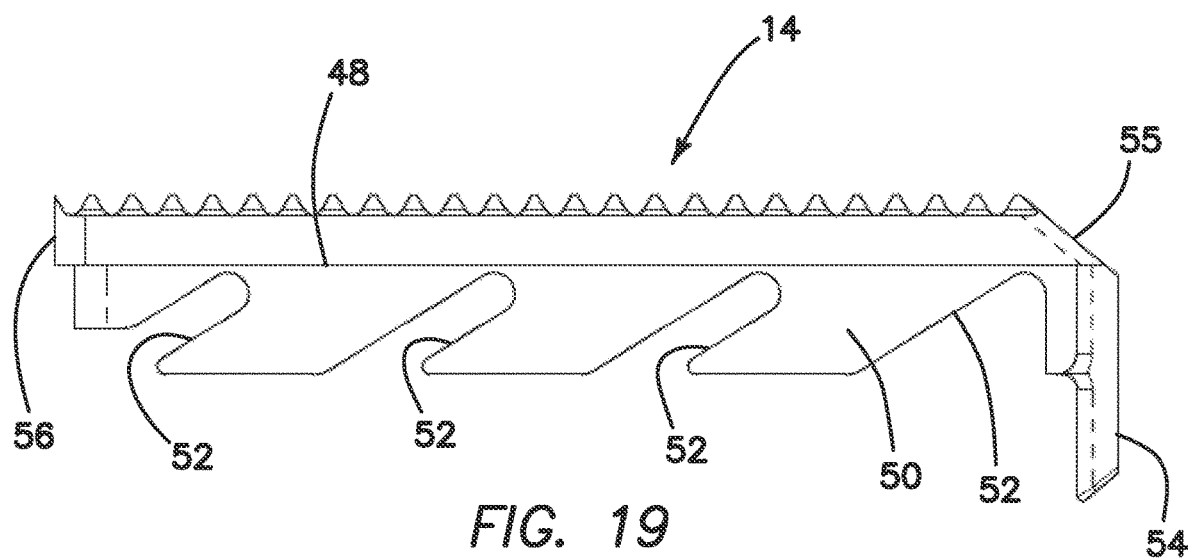
FIG. 19 is a side elevational view of the endplate of FIG. 17.
Figure 20:
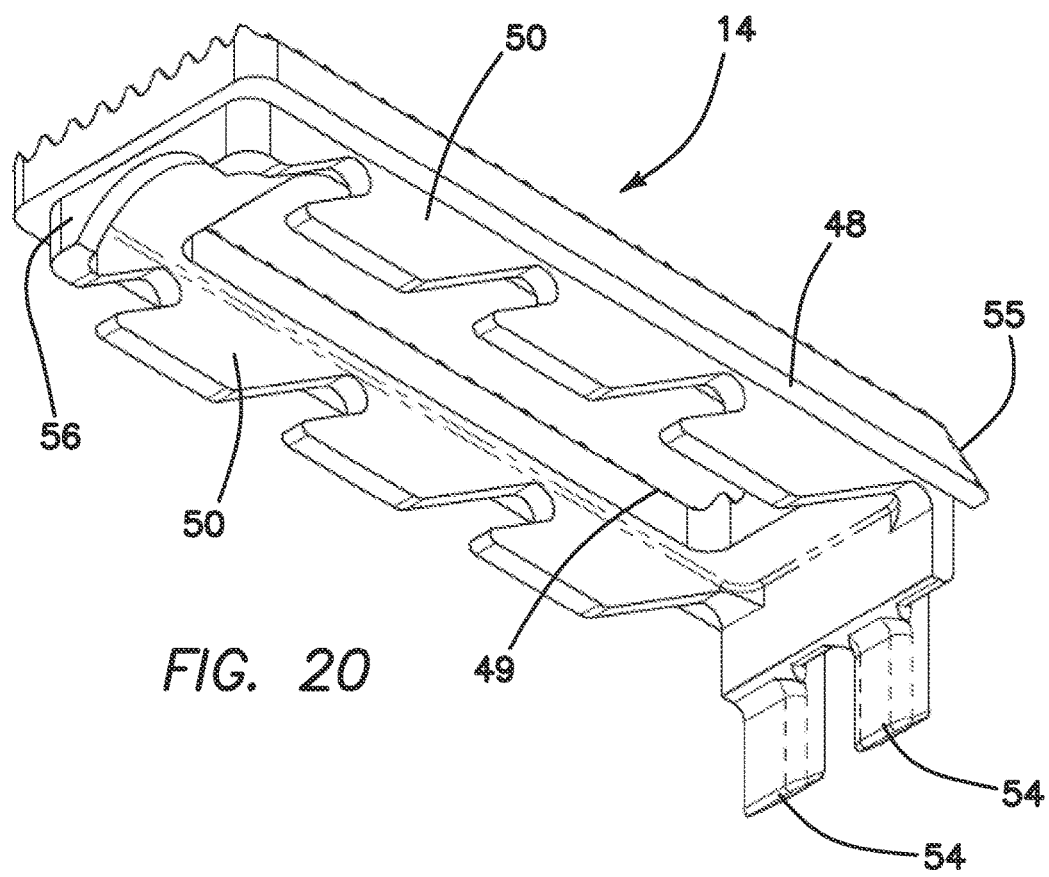
FIG. 20 is a bottom perspective view of the endplate of FIG. 17.

Turning now to FIGS. 17-20, the top and bottom endplates 14 will now be described. The top and bottom endplates 14 are identical and are connected to the housing 12 via the actuator 16. Each endplate 14 has a bone-engaging surface 46 and an interior surface 48. The bone-engaging surface 46 includes a plurality of tooth-like ridges. The ridges have pointed peaks to engage and increase the purchase on the adjacent vertebra between which the implant is located. The ridges may further be angled to help hold and prevent migration of the spacer 10 relative to the adjacent vertebrae when implanted within the intervertebral space. The endplate 14 further includes a leading surface 55 that does not have tooth-like projections like the bone-engaging surface 46. The leading surface 55 serves as an extension of the leading ramp-like surface at the distal end of the housing 12 for easily penetrating and distracting the disc space as the spacer 10 is inserted. The angle between the leading surface 55 and the bone-engaging surface 46 is equal to or greater than 90 degrees. Each endplate 14 includes at least one endplate opening 49 extending between the bone-engaging surface 46 and the interior surface 48. The endplate opening 49 reduces the weight of the spacer 10 and permits bone ingrowth to take place into the endplate 14. A family of bone graft materials, such as autograft, bone morphogenic protein (BMP), bone marrow aspirate, concentrate, stem cells and the like, may be placed inside the endplate openings 49 and into the interior of the housing 12 to promote bone growth into the spacer 10. The endplates 14 have a width that is equal to the overall width of the spacer 10 and equal to the width of the housing 12. The interior surface of the endplates 14 includes two oppositely-disposed and parallel side rails 50. The side rails 50 include oppositely disposed and parallel ramped notches 52 along the length of the side rails 50. Four ramped notches 52 are shown in FIGS. 17-18. All of the ramped notches 52 have the same angle with respect to the interior surface 48 and are configured for receiving and engaging correspondingly sized and shaped ramps of the actuator 16 having the same angle. The interior surface 48 includes two projections 54 at the distal end and a proximal endwall 56 that is curved to accommodate the proximal end of the actuator 16. The two projections 54 of the top endplate 14 interdigitate with the two projections 54 of the bottom endplate 14 as can be best seen in FIGS. 9-10 wherein the channel-like spaces between the projections 54 of the top endplate 14 are sized and configured to receive the projections 54 of the bottom endplate 14 and vice versa.

Figure 21:
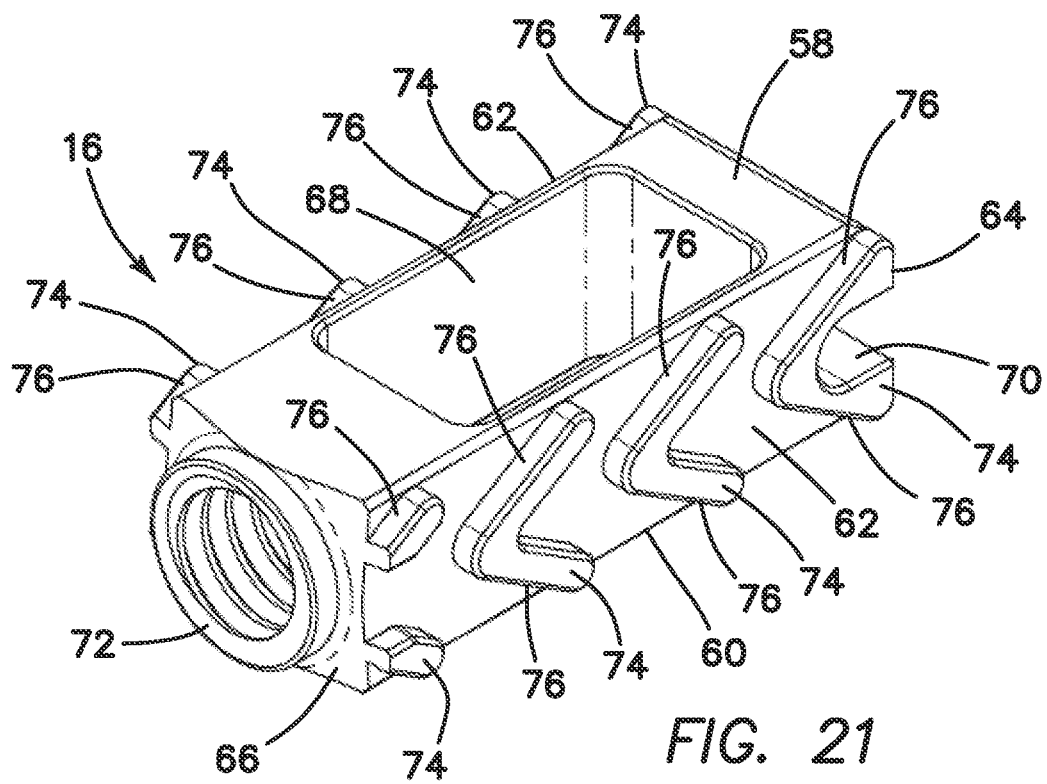
FIG. 21 is a rear top perspective view of an actuator of an expandable interbody spacer according to the present invention.
Figure 22:
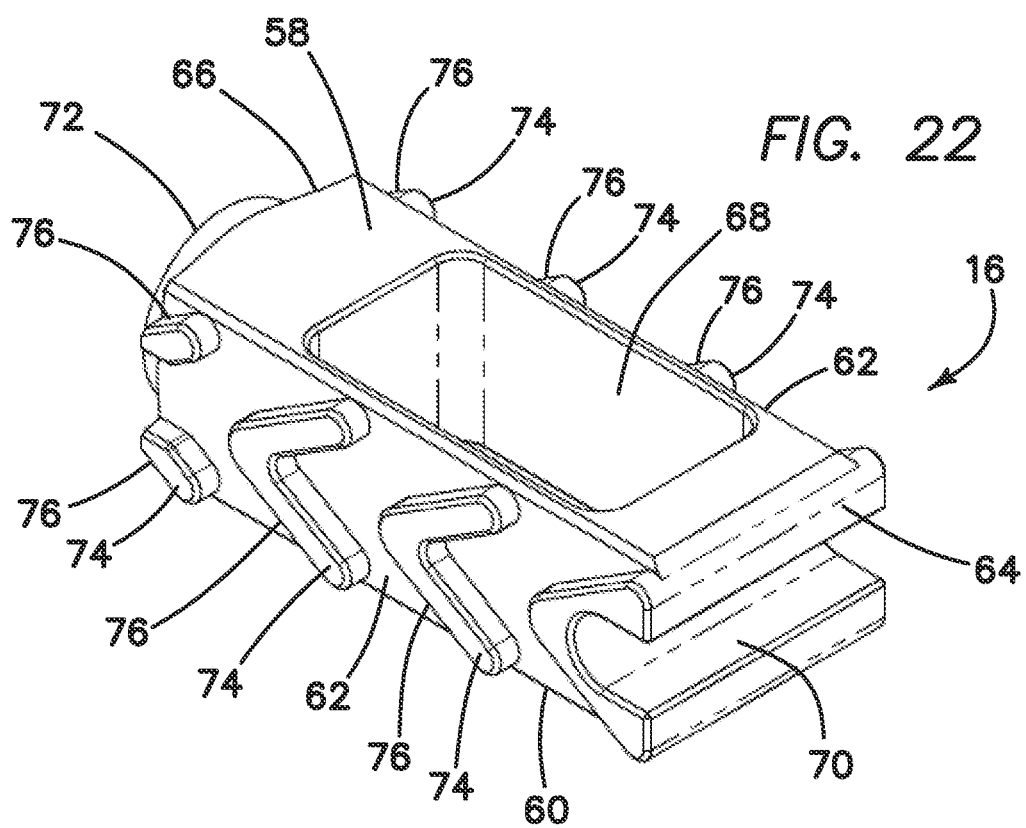
FIG. 22 is a front top perspective view of the actuator of FIG. 21.

Turning now to FIGS. 21-22, the actuator 16 will now be described. The actuator 16 is located between the two endplates 14 and inside the interior of the housing 12. The actuator 16 includes two sidewalls 62 interconnected by a top wall 58, bottom wall 60, a front wall 64 and a back wall 66. The actuator 16 is rectangular-like in shape and conforms to the rectangular-like shape of the interior of the housing 12. The actuator 16 includes an actuator opening 68 extending between the top wall 58 and bottom wall 60. The actuator opening 68 reduces the weight of the spacer 10 and permits bone ingrowth to take place in through the endplate openings 49 and into the actuator opening 68. A family of bone graft materials, such as autograft, bone morphogenic protein (BMP), bone marrow aspirate, concentrate, stem cells and the like, may be placed inside the actuator opening 68 to promote bone growth into the spacer 10. The front wall 64 of the actuator 16 includes an alignment channel 70 sized and configured to receive the alignment pin 22. The alignment channel 70 extends along the front wall 64 and between the two sidewalls 62. The back wall 66 includes a threaded opening 72 sized and configured for threaded engagement with the locking screw 18. Each sidewall 62 includes a plurality of ramps 74 extending laterally outwardly from the sidewall 62. The plurality of ramps 74 on each sidewall 62 are configured to engage the ramped notches 52 of the top endplate 14 and ramped notches 52 of the bottom endplate 14. The ramps 74 are substantially V-like in shape such that one leg of the V-like shape is configured to engage the top endplate 14 and the other leg of the V-like shape is configured to engage the bottom endplate 14. The distal-most ramp 74 includes the alignment channel 70 located between the two legs of the V-shape. The proximal-most ramp 74 does not include the apex of a V-shape and constitutes two shorter legs extending to the back wall 66. Each ramp 74 includes an angled outer driving surface 76 extending laterally outwardly from the sidewall 62. The angled outer surface 76 is perpendicular to the sidewall 62. The angle of the ramps 62 correspond to the angle of the ramped notches 52 in the endplates 14. Also, the ramps 62 are sized and configured to be received inside and engage against the ramped notches 52 in the endplates 14.

Figure 26:
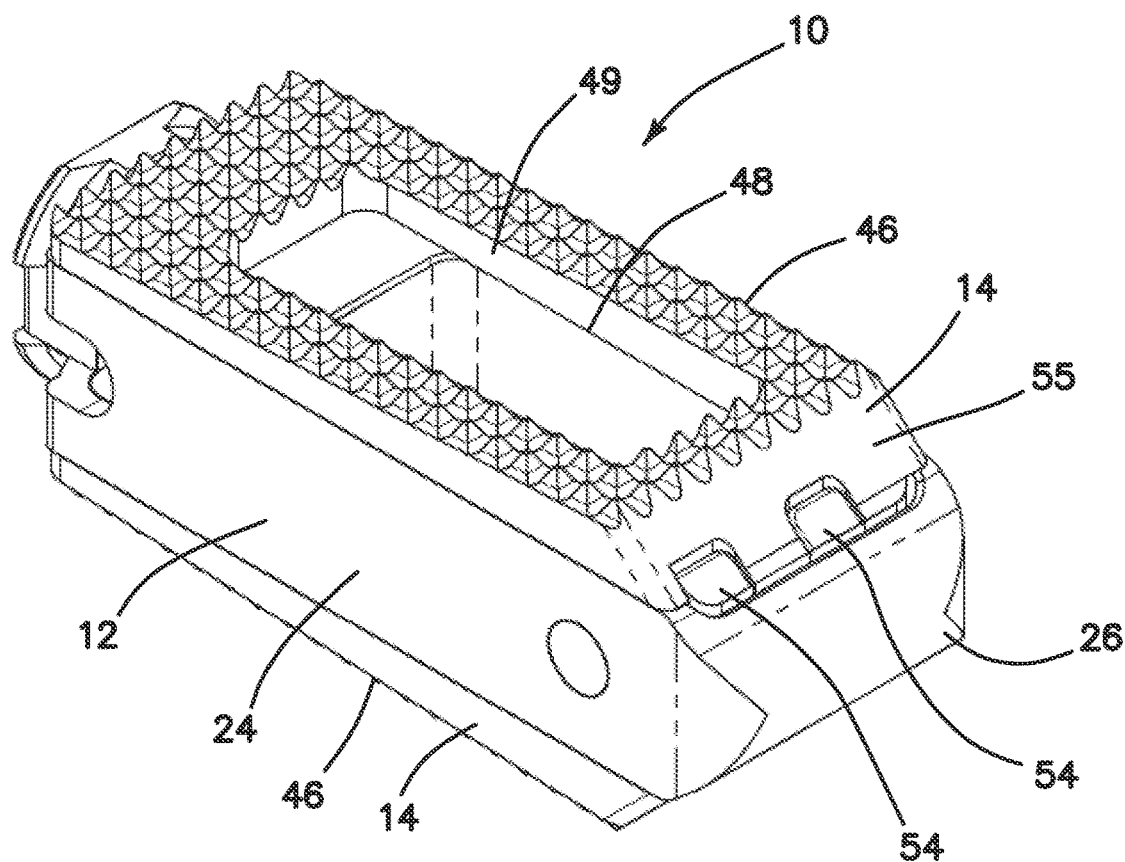
FIG. 26 is a front top perspective view of an expandable interbody spacer with angled endplates according to the present invention.
Figure 27:
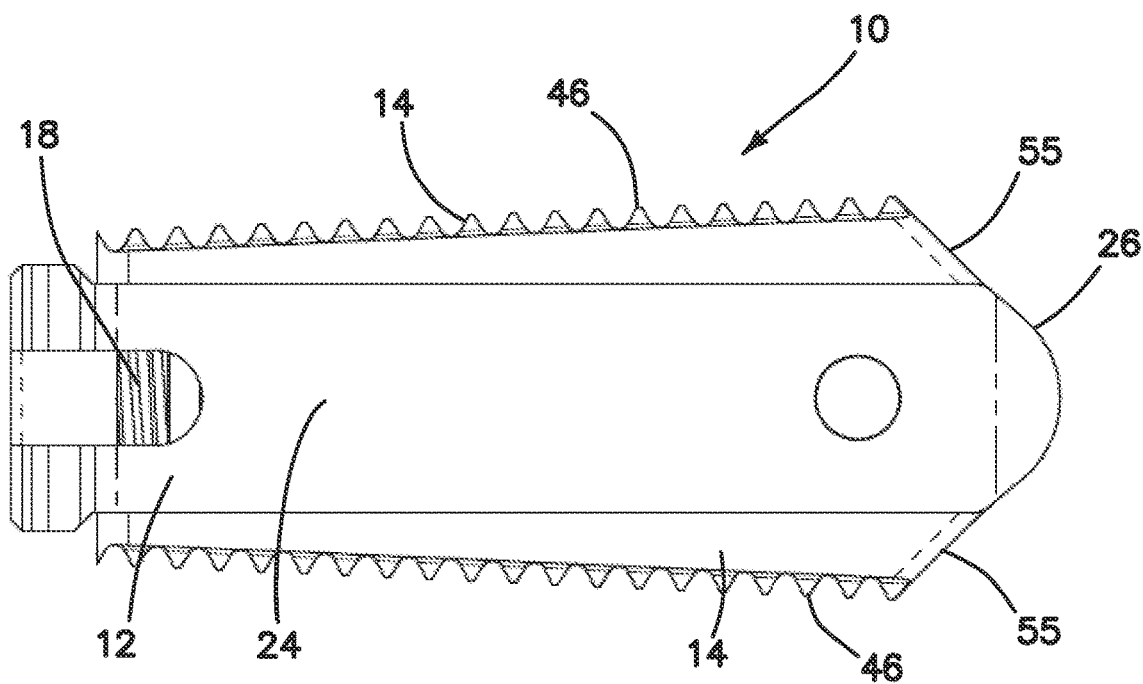
FIG. 27 is a side elevational view of the expandable interbody spacer FIG. 26.

With reference to FIGS. 26-27, there is shown another variation of the expandable interbody spacer 10 according to the present invention. The implant of FIGS. 26-27 includes a variation in endplates 14 wherein the rest of the components are the same as described herein. In FIGS. 26-27, each endplate 14 includes a bone-engaging surface 46 that is angled with respect to the interior surface 48 of the endplate 14. Hence, the expandable interbody spacer 10 has an angled, ramped profile while in the unexpanded configuration and in the expanded configuration. The angled profile is such that the height of the spacer 10 endplate 14 is greater at the distal end of the spacer 10 relative to the height of the spacer 10 endplate 14 at the proximal end of the spacer 10. The endplates 14 have an angle with respect to the horizontal between zero and approximately 30 degrees. The top end and bottom end of the housing 12 are parallel to each other as are the interior surfaces 48 of the top and bottom endplates 14 in the expanded and unexpanded configurations. The thickness of the endplates 14 is greater at the distal end and tapers toward the proximal end to form the angle. In another variation, the spacer 10 may have the angle reversed wherein the height/thickness of the spacer 10 endplate 14 is greater at the proximal end relative to the height of the spacer 10 endplate 14 at the distal end. Such a configuration may be suitable for ALIF procedures in restoring the natural lordotic curvature of the spine segment. The top and bottom endplates 14 are identical and configured for parallel expansion with respect to the housing 12 such that the angle remains the same in the expanded and unexpanded configurations. The endplate 14 of FIGS. 26-27 further includes a leading surface 55 that does not have tooth-like projections like the bone-engaging surface 46. The leading surface 55 serves as an extension of the leading ramp-like surface at the distal end of the housing 12 for easily penetrating and distracting the disc space as the spacer 10 is inserted. The angle between the leading surface 55 and the bone-engaging surface 46 is equal to or greater than 90 degrees.

Figure 28:
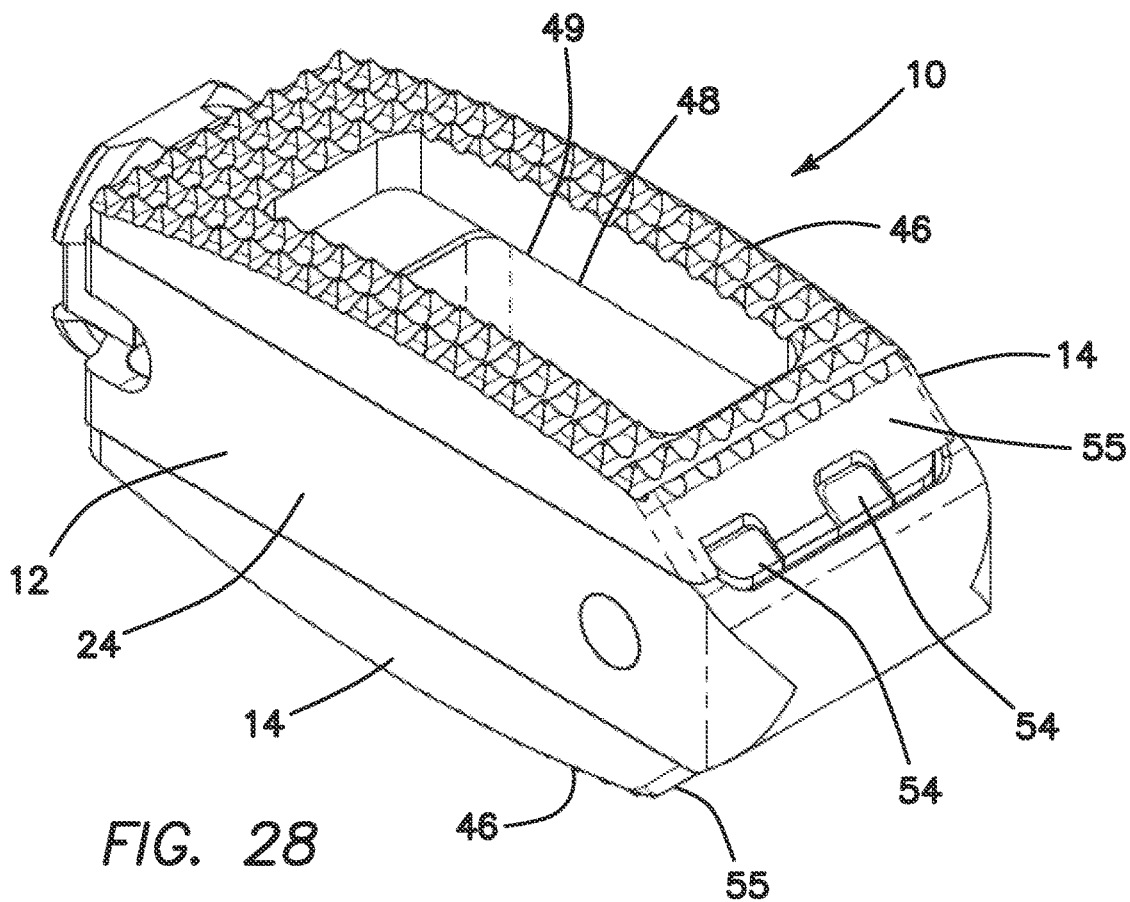
FIG. 28 is a front top perspective view of an expandable interbody spacer with curved endplates according to the present invention.
Figure 29:
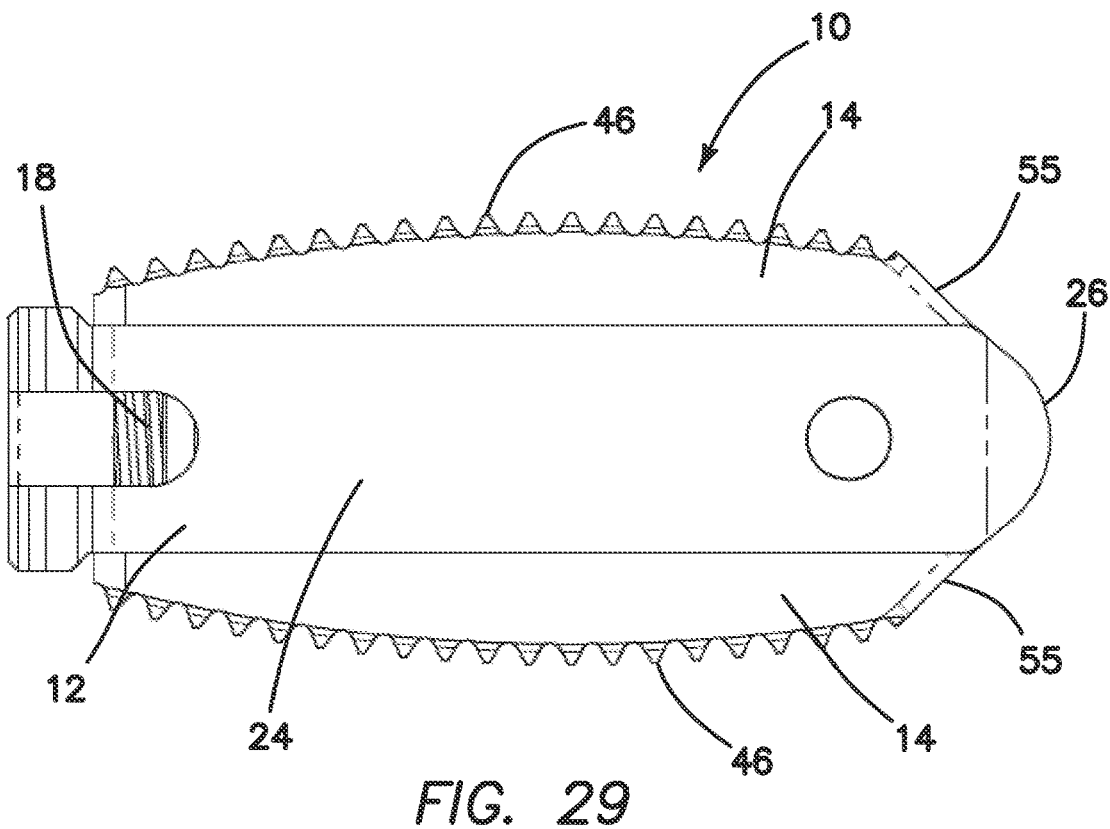
FIG. 29 is a side elevational view of the expandable interbody space of FIG. 28.
Figure 30:
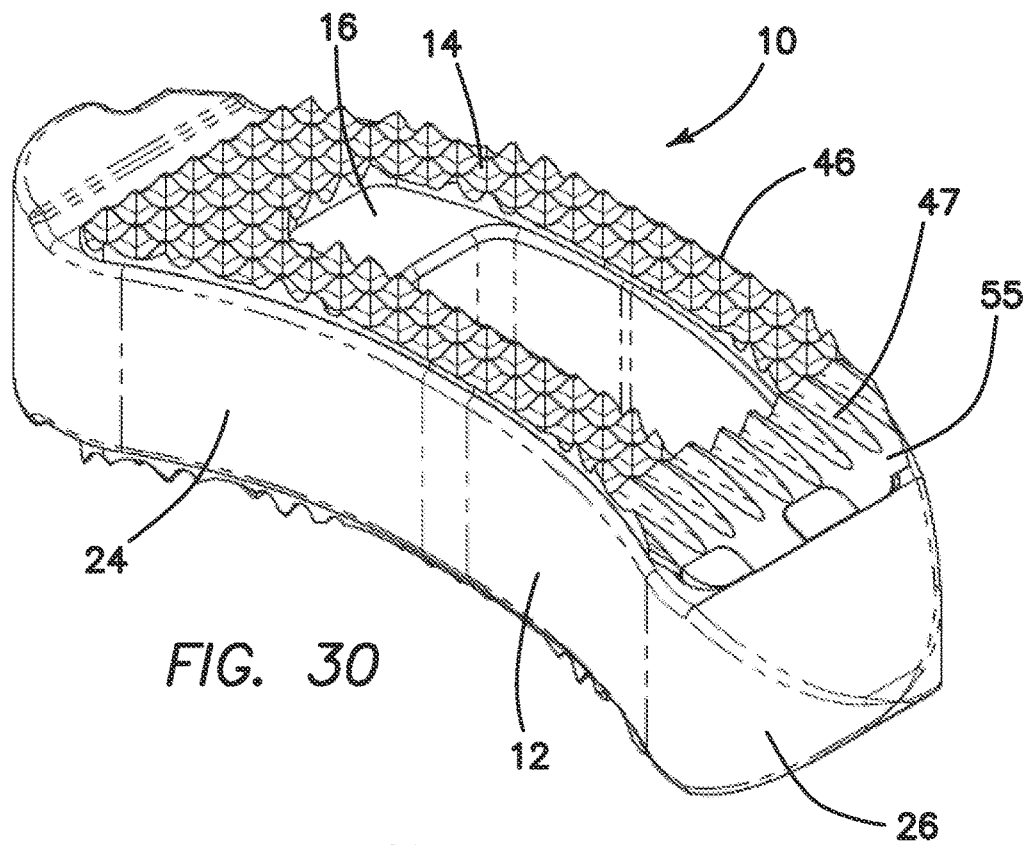
FIG. 30 is a front top perspective view of a banana-shaped expandable interbody spacer in its low-profile configuration according to the present invention.
Figure 31:
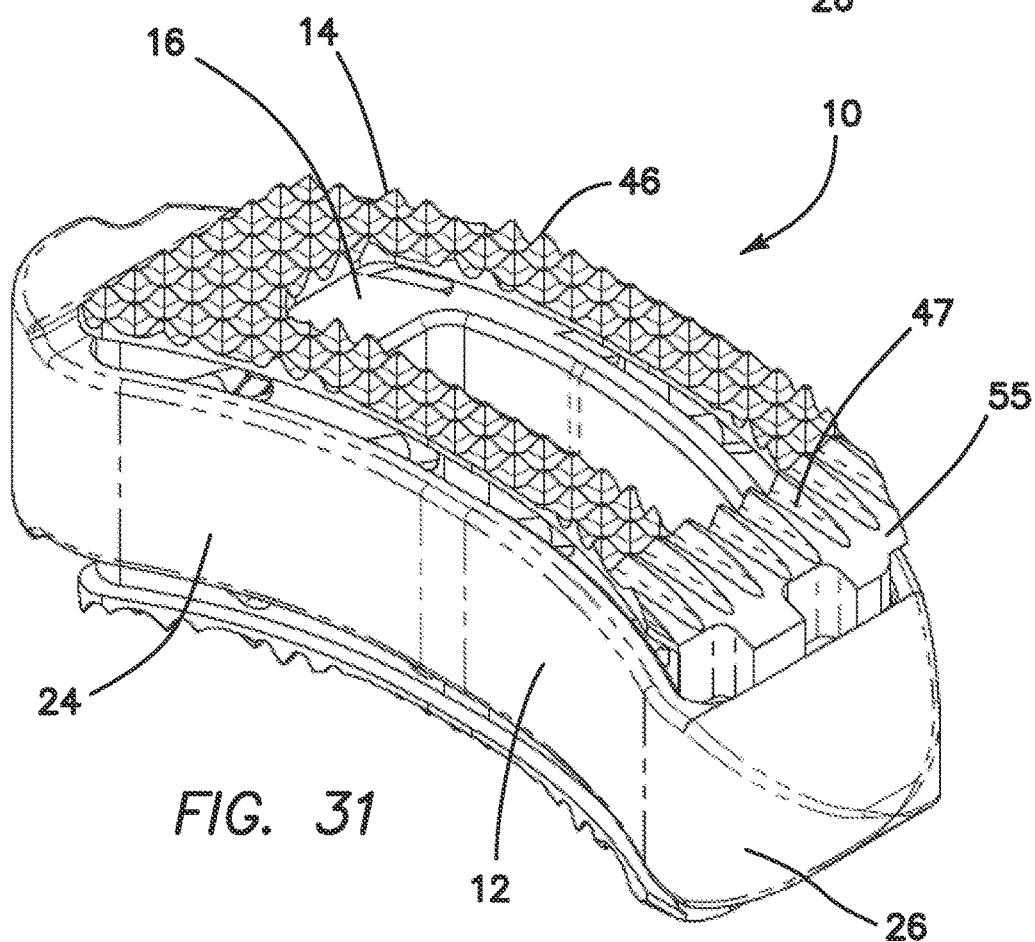
FIG. 31 is a front top perspective view of the expandable interbody spacer of FIG. 30 in its high-profile configuration.
Figure 32:
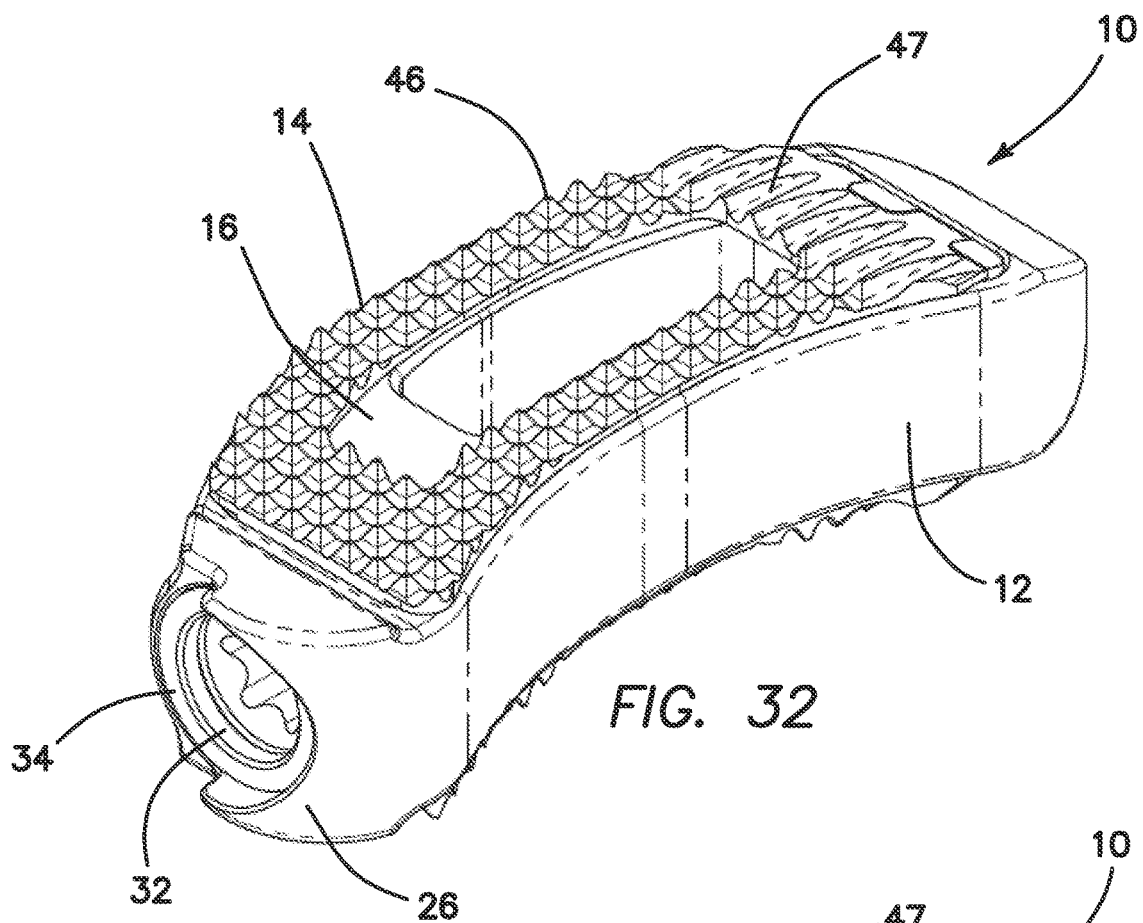
FIG. 32 is a rear top perspective view of the expandable interbody spacer of FIG. 30.
Figure 33:
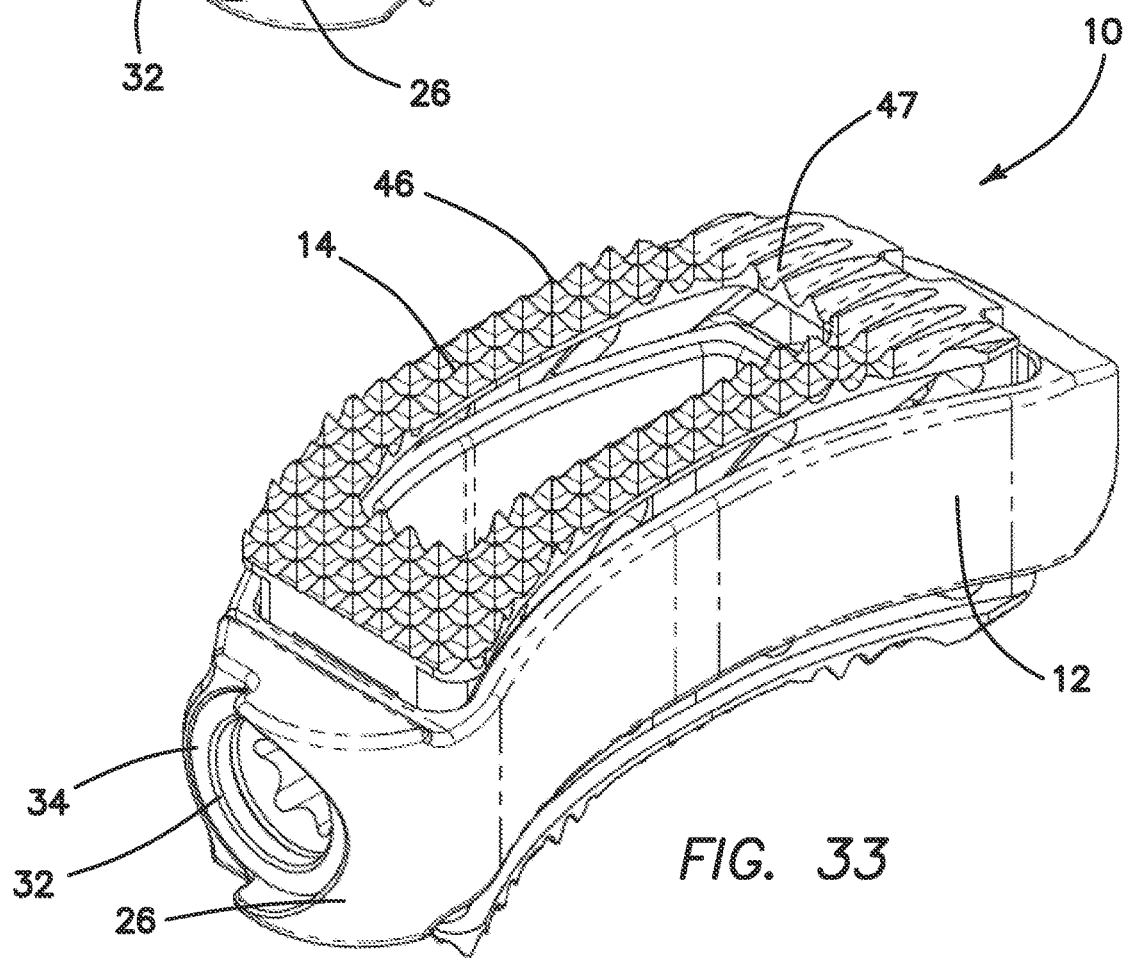
FIG. 33 is a rear top perspective view of the expandable interbody spacer of FIG. 31.
Figure 34:
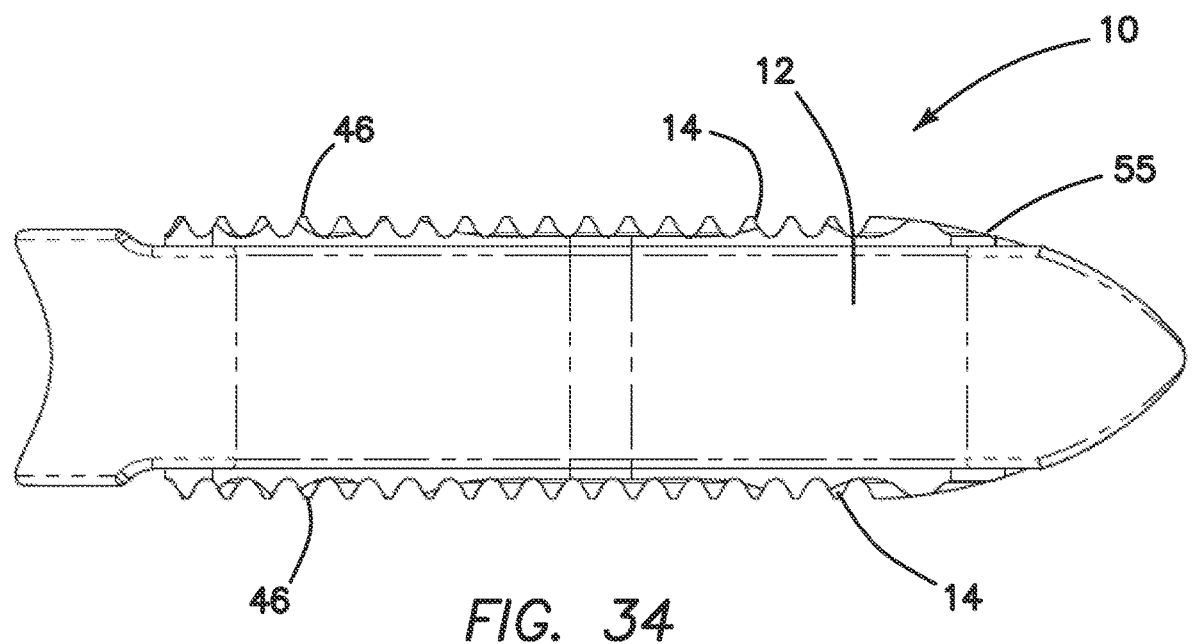
FIG. 34 is a side elevational view of the expandable interbody spacer of FIG. 30.
Figure 35:
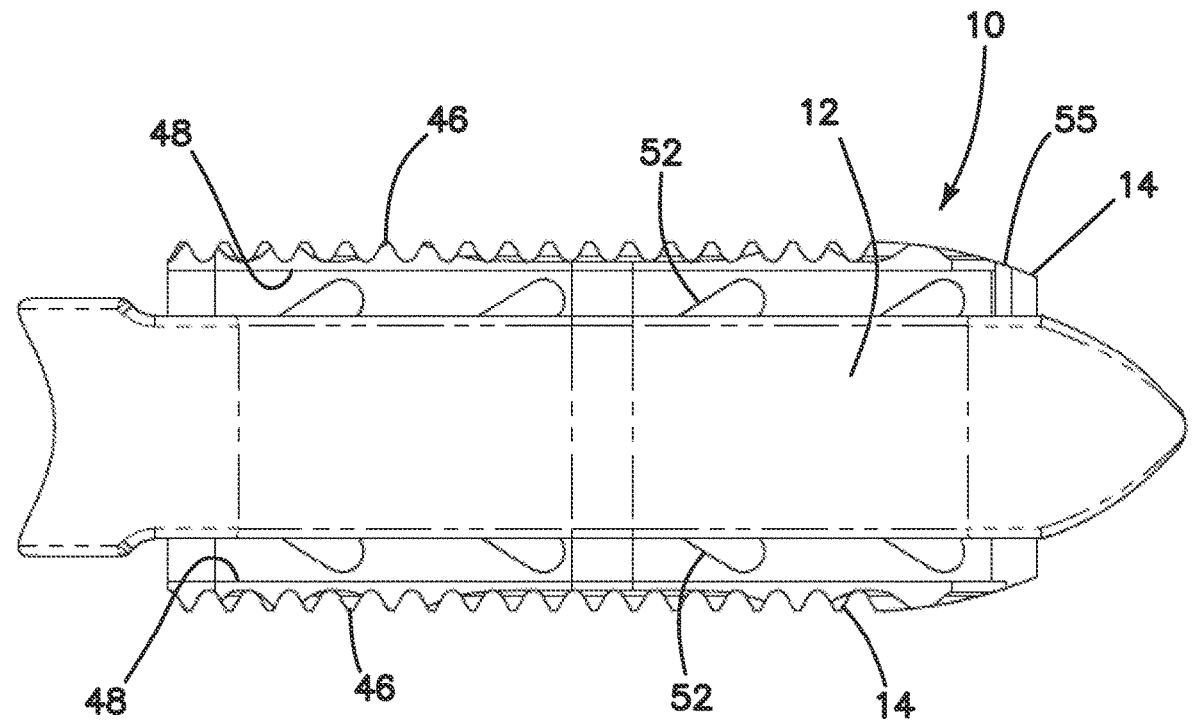
FIG. 35 is a side elevational view of the expandable interbody spacer of FIG. 31.
Figure 36:
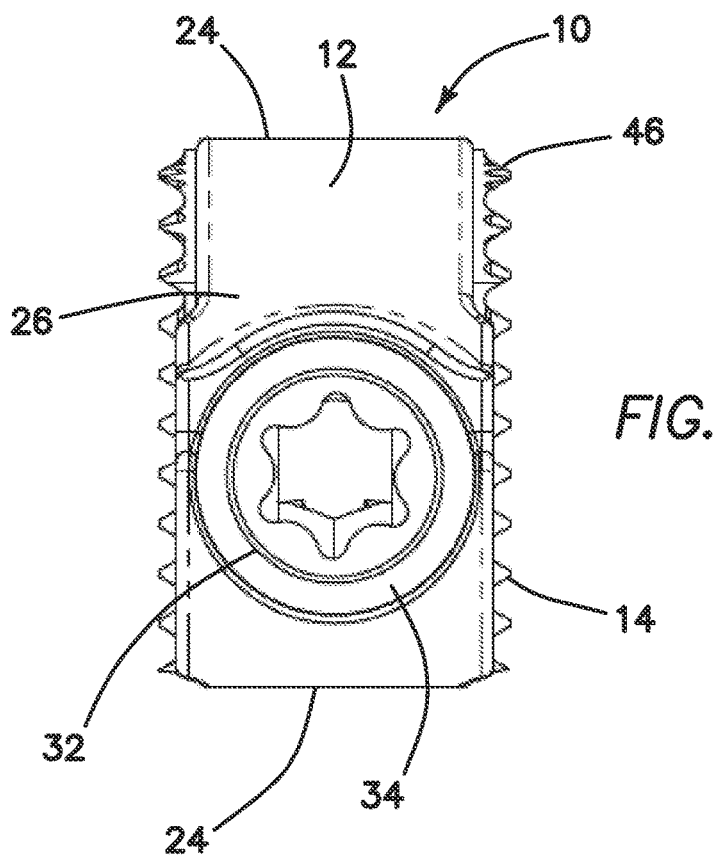
FIG. 36 is a rear elevational view of the expandable interbody spacer of FIG. 30.
Figure 37:
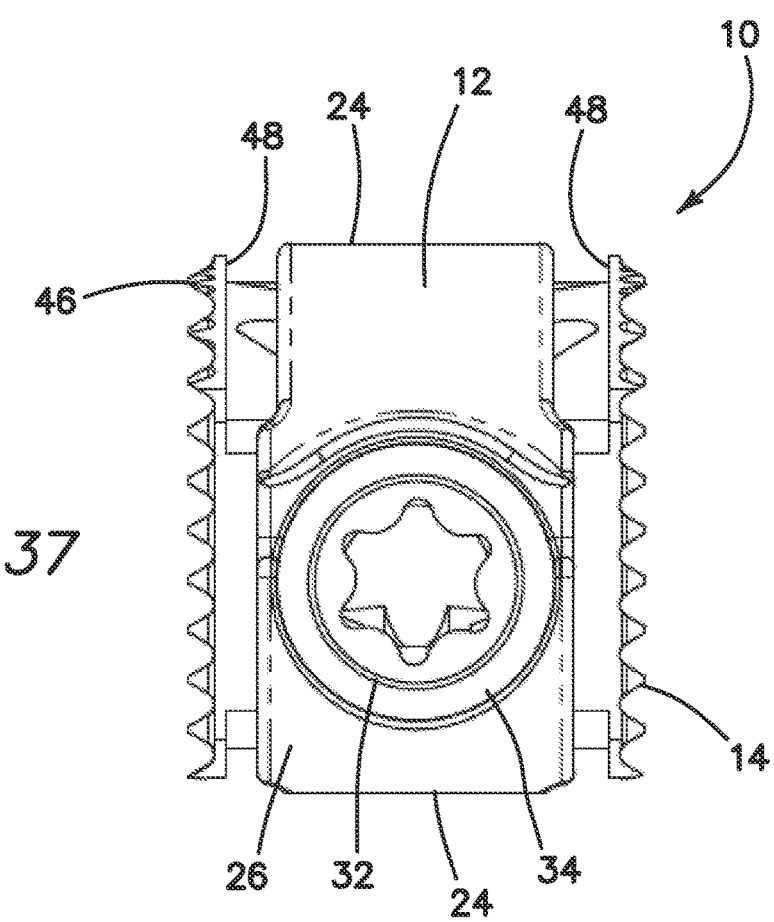
FIG. 37 is a rear elevational view of the expandable interbody spacer of FIG. 31.

With reference to FIGS. 28-29, there is shown another variation of the expandable interbody spacer 10 according to the present invention. The implant of FIGS. 28-29 includes a variation in endplates 14 wherein the rest of the components are the same as described herein. In FIGS. 28-29, each endplate 14 includes a bone-engaging surface 46 that is curved outwardly with respect to the interior surface 48 of the endplate 14. Hence, the expandable interbody spacer 10 has convex bone-engaging surface 46 on both sides in the expanded and unexpanded configurations. The top and bottom endplates 14 are identical and configured for parallel expansion with respect to the housing 12 such that the profile of the spacer 10 remains the same in the expanded and unexpanded configurations. The endplate 14 of FIGS. 28-29 further includes a leading surface 55 that does not have tooth-like projections like the bone-engaging surface 46. The leading surface 55 serves as an extension of the leading ramp-like surface at the distal end of the housing 12 for easily penetrating and distracting the disc space as the spacer 10 is inserted.

With particular reference to FIGS. 30-37, there is shown another variation of the expandable interbody spacer 10 according to the present invention wherein like numbers are used to describe like parts. The spacer 10 of FIGS. 30-37 has a curvilinear geometry between the distal end and the proximal end that may be described as having a kidney bean-like, banana-like, crescent, curved, slightly curved, arcuate, c-like shape that facilitates contact with the cortical bone and is typical of implants used in a TLIF procedure. The shape is defined by the housing 12, endplates 14 and actuator 16. The housing 12 is substantially the same as described with respect to FIGS. 15-16 except that the sidewalls 24 of the housing are bowed in a parallel fashion with one sidewall 24 having a concave outer surface and the opposite sidewall 24 having a convex outer surface interconnected by generally curved endwalls 26. The distal endwall 26 is curved outwardly and defines a peak-like tip, forming a ramp-like surface with the top and bottom surfaces of the distal endwall 26. The proximal endwall 26 is also curved and includes a recess where the collar 34 and rear opening 32 are located. The housing 12 defines a curved interior for receiving a similarly-curved actuator 16 through the open top or bottom of the housing 12. The top and bottom endplates 14 are also substantially the same as described with respect to FIGS. 17-20, except that the sides and the side rails 50 are curved giving the endplates 14 a crescent shape that corresponds to the curved shape of the housing 12. One side of each endplate 14 is concave and the opposite side is convex and substantially parallel to each other. The ends are generally straight and parallel to each other. The endplates 14 include a leading surface 55 that is slightly angled to serve as an extension of the leading ramp-like surface at the distal end of the housing 12. To facilitate penetration into and distraction of the disc space, the leading surface 55 includes a plurality of parallel cutting flutes 47. The cutting flutes 47 are narrow at the distal end and widen toward the proximal end. The curved side rails 50 of the endplate 14 include four ramped notches 52 configured to engage the ramps 74 of the actuator 16 as described above. Aside from the banana-like shape, the assembly and operation of the spacer 10 is the same.

The expandable interbody spacer 10 is assembled by first connecting the endplates 14 to the actuator 16. The ramps 74 of the actuator 16 are inserted into the ramped notches 52 of the both the top and bottom endplates 14. This subassembly is inserted into the interior of the housing 12 and the alignment pin 22 is inserted through the alignment pin apertures 28 of the housing 12. The locking screw 18 is inserted through the rear opening 32 of the housing 12 and into the threaded opening 72 of the actuator 16. The locking ring 20 is inserted in through the rear opening 32 and into the collar 34 of the housing 12 and welded thereto where it prevents the locking screw 28 from backing out of the housing 12.

In use, the present expandable interbody spacer 10 is inserted into the disc space between adjacent vertebral bodies. The spacers 10 of FIGS. 1-29 are generally configured for use as a PLIF cage in spinal surgical procedures and the spacer 10 of FIGS. 30-37 is generally configured for use as a TLIF cage. It is understood that novel features of the present invention can find application in different types of spacers including but not limited to interbody spacers for PLIF, TLIF, XLIF surgical procedures as well as other types of orthopedic implants.

Implanting the interbody spacer 10 involves removal, in whole or in part, of the disc material from the intervertebral space at the target vertebral level where the interbody spacer 10 will be implanted. The patient is oriented to provide some distraction of the disc space and to provide access to the spine. Additional distraction of the disc space and surrounding tissues may be needed to decompress the nerve roots, realign the anatomical axis of the spine, and restore disc space height at the particular target level. After disc material is removed, a clean space is achieved in which to place the device. The vertebral endplates may be further prepared using burrs, curettes and the like to abrade and clean the endplates to encourage bone regeneration.

A surgeon will then select an appropriate spacer 10 for the target space and connect it to an insertion instrument (not shown). The insertion instrument is connected at the proximal end of the spacer 10 such that it is secured to the collar 34, for example, by engaging the insertion instrument around the outer recess 44. The insertion instrument includes a drive mechanism that is configured to engage the socket 45 of the locking screw 18. The surgeon uses the insertion instrument to grasp the spacer 10 and place it at the mouth of the intervertebral space in its low-profile configuration. The spacer 10 is moved and orientated into its proper position within the intervertebral space. Bone graft or other material may be placed inside the interior of the spacer 10 through the endplate and actuator openings 49, 68. The bone graft material promotes ingrowth and improves blood supply in order to grow active and live bone from the adjacent spinal vertebrae to inter-knit with the spacer 10 and, thereby, eventually immobilize and fuse the adjunct spinal vertebrae.

As the spacer 10 is moved within the vertebral space, the distal endwall 26, which is ramped, facilitates insertion and distraction of the vertebral bodies. Also, the leading surface 55 of the endplate 14 further facilitates wedging the spacer 10 into position. The cutting flutes 47 further help to embed the spacer 10. The spacer 10 is placed such that the top endplate 14 contacts the lower endplate of the upper vertebral body and the bottom endplate 14 of the spacer 10 contacts the upper endplate of the lower vertebral body on either side of the target intervertebral space. The geometry of the teeth on the bone-engaging surface 46 provide resistance to migration of the spacer 10 while inside the target space. Other coatings and surface textures may also be provided on the spacer 10. When the spacer 10 is in position, the insertion instrument is used to deploy the spacer into its expanded or high-profile configuration. The insertion instrument is configured to rotate the locking screw 18 in one of a first clockwise or counter-clockwise direction. Rotation of the locking screw 18 in a first direction results in translation of the actuator 16 in a proximal direction relative to the housing 12. Other than rotation about its longitudinal axis, the locking screw 18 remains stationary with respect to the housing 12. As the actuator 16 moves proximally relative to the housing 12, the ramps 74 slide against the ramped notches 52 moving both the top and bottom endplates 14 up along the ramps 74 and outwardly into parallel expansion that is proportional to the degree of rotation of the locking screw 18. The surgeon can adjust the distance/height of expansion by rotating the locking screw 18 clockwise or counter-clockwise as needed according to surgeon preference and patient anatomy. With rotation of the locking screw 18 in one of a second clockwise or counter-clockwise direction opposite to the first direction, the distance of expansion of the endplates 14 is reduced in direct proportion to degree of rotation in the second direction. Hence, the surgeon can increase or reduce the height of the spacer 10 as needed to not only facilitate placement of the spacer 10 but also to obtain optimum and customized distraction of the vertebral space for the patient. Advantageously, the locking screw 18 floats and does not translate in a proximal or distal direction when rotated in a clockwise or counter-clockwise direction. As a result, the longitudinal length of the spacer 10 remains the same before expansion and after expansion and, therefore, does not result in the locking screw 18 protruding outwardly beyond the perimetrical footprint in the longitudinal direction of the spacer 10 and potentially impinging on surrounding tissue or interfering spatially with bone ingrowth around the spacer 10. Advantageously, the locking screw 18 also does not protrude laterally. After the spacer 10 is properly positioned, the insertion instrument is detached and removed from the operating field. Further advantageously, the top and bottom endplates 14 do not translate proximally or distally along the longitudinal direction when going from the low-profile configuration to the high-profile configuration and vice versa. Therefore, the endplates 14 advantageously do not protrude distally or proximally beyond the perimetrical footprint in the longitudinal direction of the spacer and, therefore, spacer 10 prevents impingement of the surrounding tissue and nerves. Because the spacer 10 does not change in length in going between the low-profile and high-profile configurations, implantation of the spacer 10 is facilitated for the surgeon who does not have to compensate for an increase in length or location of contact with the vertebral bodies when positioning the spacer 10. Also, advantageously, the spacer 10 of the present invention expands uniformly, simultaneously and bilaterally along the latitudinal direction which is transverse to the longitudinal axis of the spacer 10 which extends along the length of the spacer, thereby, providing greater stability to the spinal column. Further advantageously, the surface area of the bone-engaging surface 46 of both endplates 14 does not change when going between the low-profile and high-profile configurations as is the case for implants not in accordance with the present invention. For example, certain implants have a larger surface area that is in contact with vertebral bone when in the low-profile configuration and a smaller bone-engaging surface when in the high-profile configuration creating a less stable distraction and lost bone-toimplant contact area that is initially prepped by surgeon creating unnecessary damage to the bone and longer implantation time. Some spacers, not in accordance with the present invention, increase or decrease in length as one or more of the endplates moves distally or proximally along the longitudinal direction in going between the low-profile and high-profile configuration. This longitudinal movement of the endplates causes a sliding lateral traction between two vertebral bodies which is advantageously avoided in the present invention. Additional instrumentation such as rods or screws may also be used to further stabilize the spine across the target level. If needed, to remove the spacer 10, the insertion instrument is attached to the proximal end of the spacer 10 and engaged with the socket 45 of the locking screw 18. Then, the insertion instrument is employed to rotate the locking screw 18 in a second direction to reduce the height of expansion. As the locking screw 18 is rotated, it remains stationary with respect to the housing 16 other than rotation around its longitudinal axis. Rotation of the locking screw 18 in the second direction moves the actuator 16 distally relative to the housing 12. As a result, the ramped notches 52 slide down the ramps 74 of the actuator 16 such that both the top and bottom endplates 14 move inwardly and the distance between the two endplates 14 and height of the spacer 10 is reduced configuring the spacer 10 in its low-profile configuration. In the low-profile configuration, the spacer 10 is easily removed from the disc space or relocated and re-expanded.

The expandable interbody spacer 10 is made of any suitable biocompatible material. The expandable interbody spacer 10 may be made from any one or combination of one or more metal such as titanium, ceramic, polymer such as polyether ether ketone (PEEK), carbon fiber reinforced polymer, biomaterial including but not limited to any of a number of biocompatible implantable polymers including PEKK, PEKEK, polyetheretherketone (PEEK) being preferred, titanium ceramic, bone or other material etc. The present invention can be employed and is suitable for use anywhere along the spine including but not limited to cervical, thoracic, lumbar or sacral or between other bony structures outside of the spinal region. Embodiments of the present invention are standalone interbody devices which may be designed in the general style of a TLIF device, PLIF device, ALIF or other device. In addition, the size and/or shape of the basic embodiments disclosed herein may be adapted by one skilled in the art for use in various levels of the spine, namely the cervical spine, thoracic spine and the lumbar spine. Thus, while various embodiments herein may be described by way of example with respect to the lumbar spine such disclosures apply with equal weight to the other levels of the spine.

Turning to FIGS. 38-59, another variation of an expandable interbody spacer 10 will be described wherein like reference numbers are used to describe like parts. The expandable interbody spacer 10 comprises a housing 12, upper and lower endplates 14, an actuator 16 located inside the housing 12 and between the upper and lower endplates 14, a locking screw 18 connected to the housing 12 by a locking ring 20 and configured to move the actuator 16, an alignment pin 22 connected to the housing 12 to align and guide the actuator 16, and a pivot pin 23 connected to the housing 12 about which the endplates 14 pivot. The expandable interbody spacer 10 is insertable into the disc space between two adjacent vertebral bodies from a posterior approach while in an unexpanded state. The unexpanded state is illustrated in FIGS. 1, 38, 40, 42, 44, 46, 48 and 50. Once inserted and properly positioned inside the disc space, both upper and lower endplates 14 are expanded angularly with respect to the housing 12 such that the height at the distal end of the expandable spacer 10 increases relative to the proximal end on both sides of the implant. Expansion is effected by rotating the locking screw 18 with an instrument by the surgeon. Rotation of the locking screw 18 moves the actuator 16 which in turn moves the endplates 14 simultaneously into angular expanded state illustrated in FIGS. 39, 41, 43, 45, 47, 49 and 51. The expandable interbody spacer 10 is advantageously easier to implant, does not require a stock of multiple implants of different sizes and helps create a lordotic angle in the spine in which the anterior height of the disc space is greater than the posterior height thereby restoring a more natural lordotic curvature of the particular segment of the spine.

Figure 38:
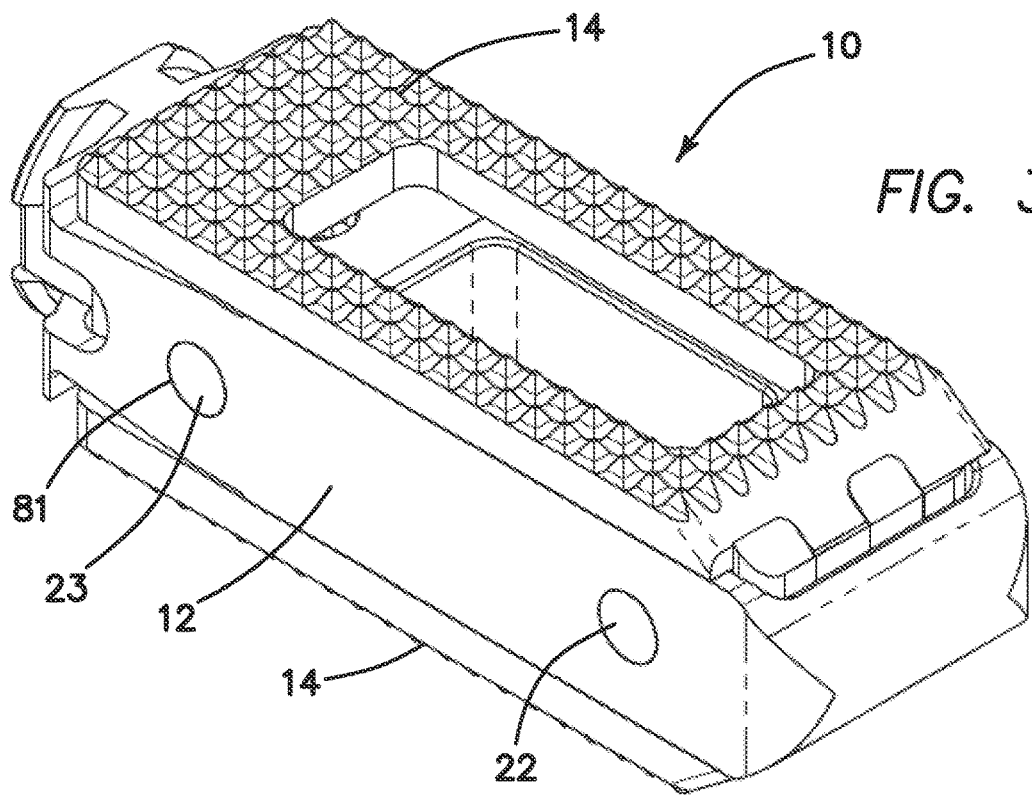
FIG. 38 is a front top perspective view of an angularly expandable interbody spacer in its low-profile configuration according to the present invention.
Figure 39:
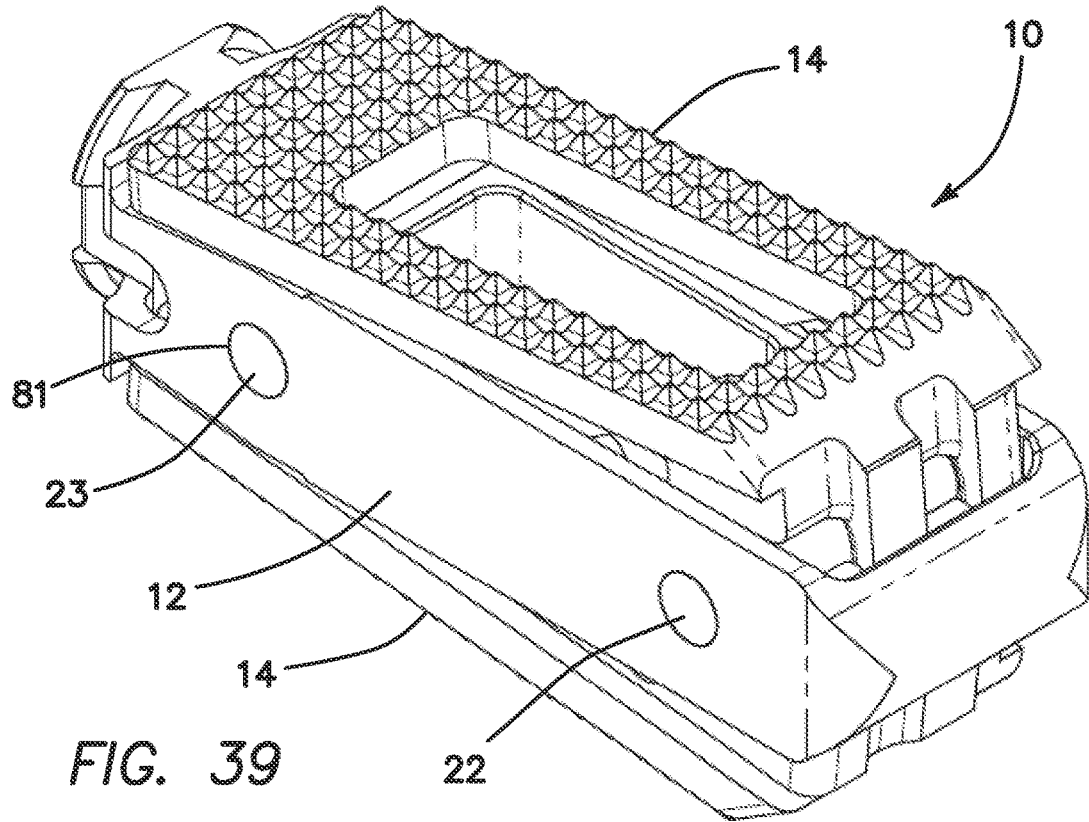
FIG. 39 is a front top perspective view of the angularly expandable interbody spacer in its expanded configuration.
Figure 40:
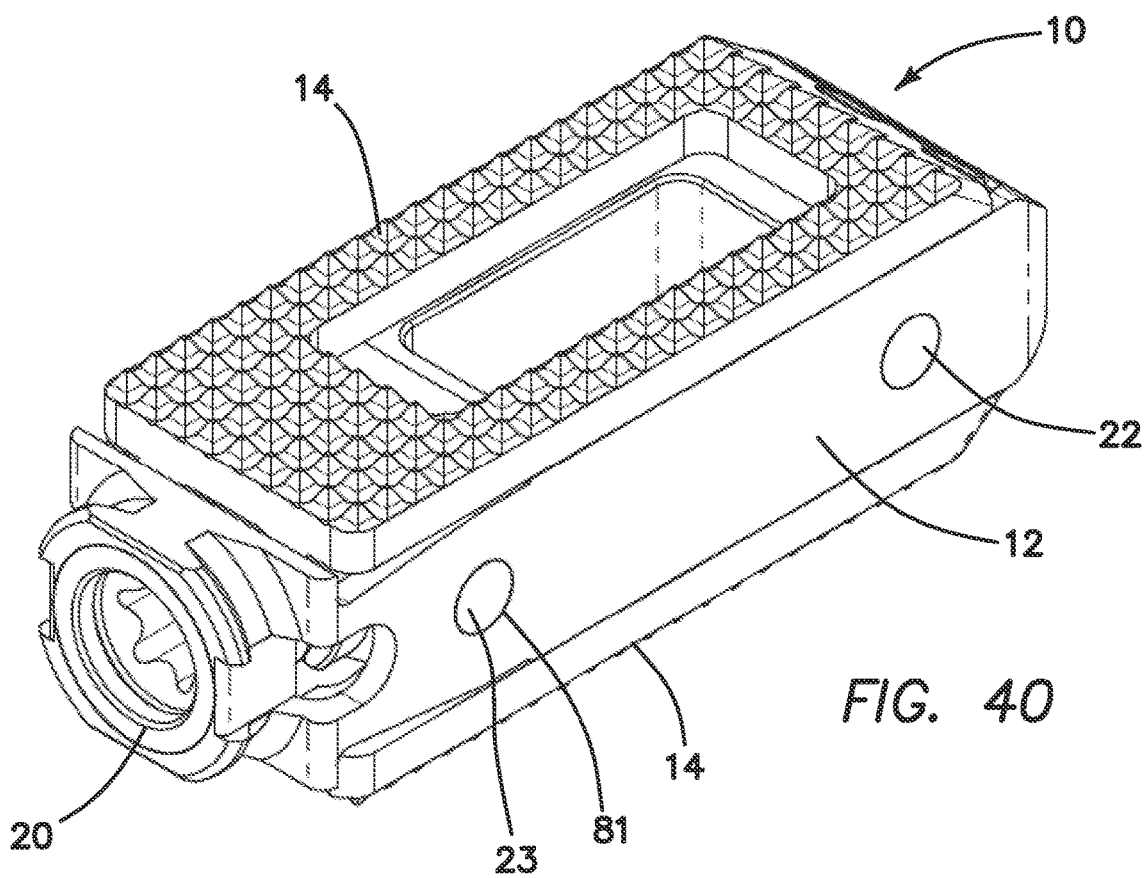
FIG. 40 is a rear top perspective view of the angularly expandable interbody spacer of FIG. 38.
Figure 41:
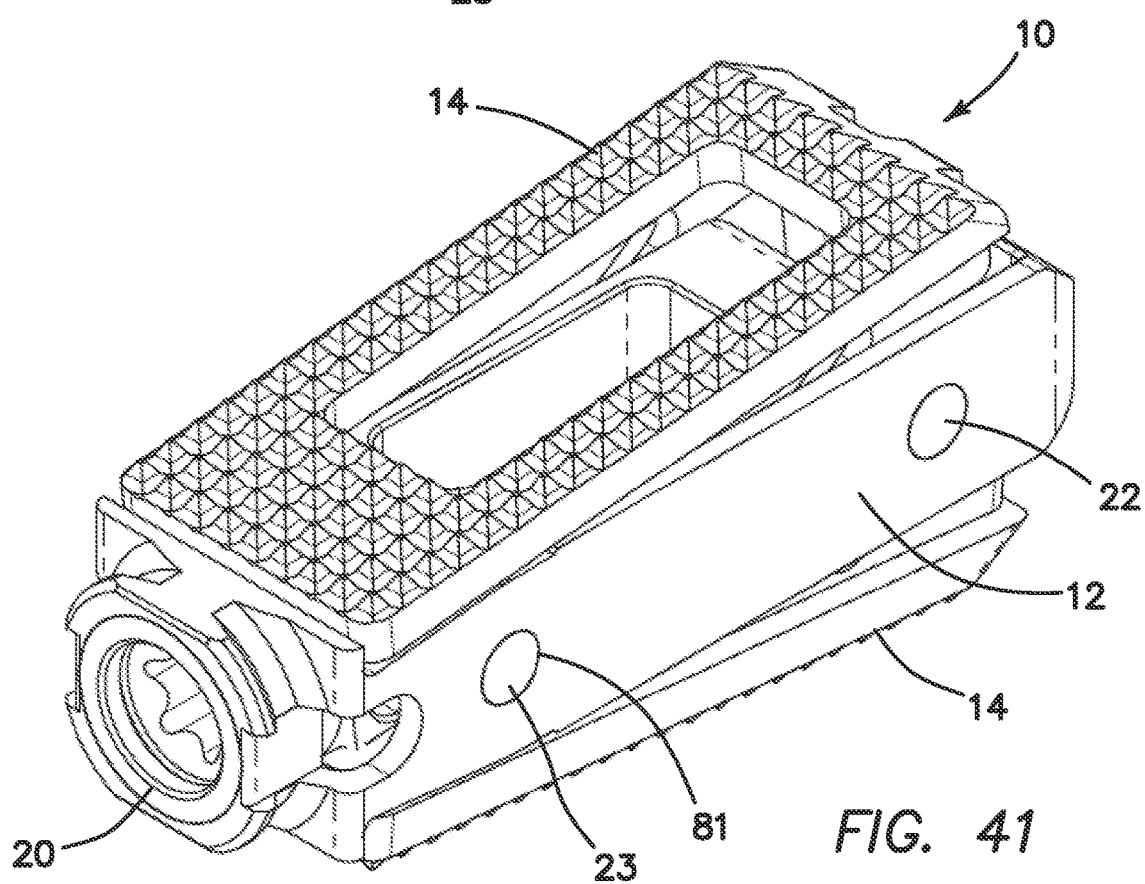
FIG. 41 is a rear top perspective view of the angularly expandable interbody spacer of FIG. 39.
Figure 42:
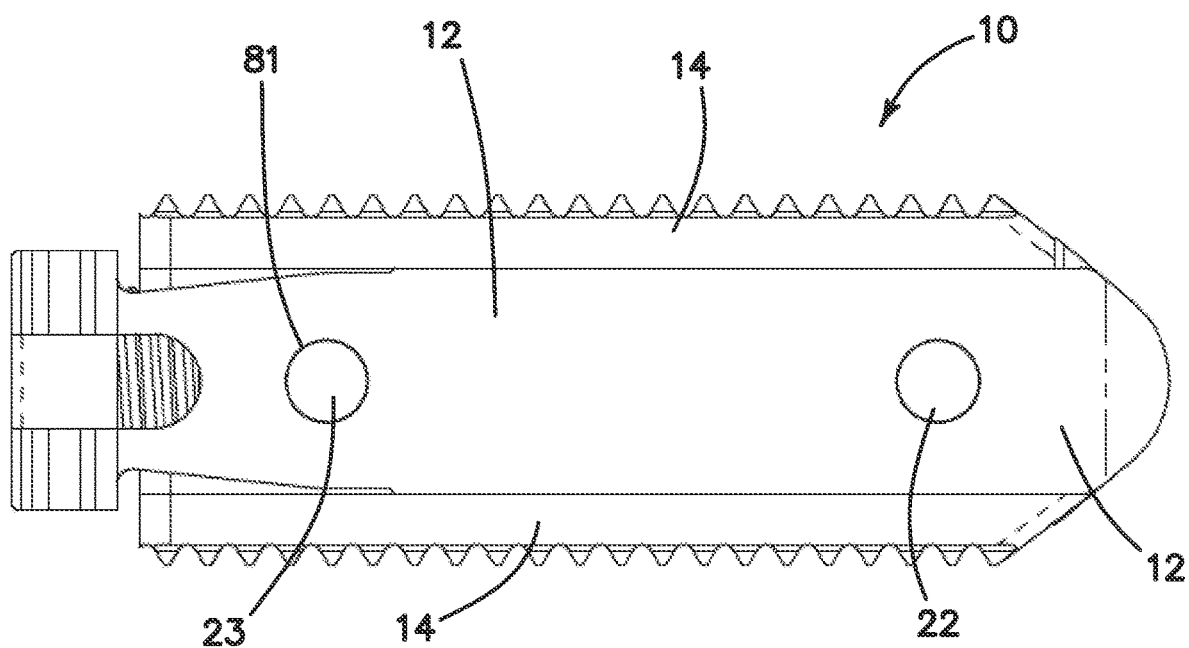
FIG. 42 is a side elevational view of the angularly expandable interbody spacer of FIG. 38.
Figure 43:
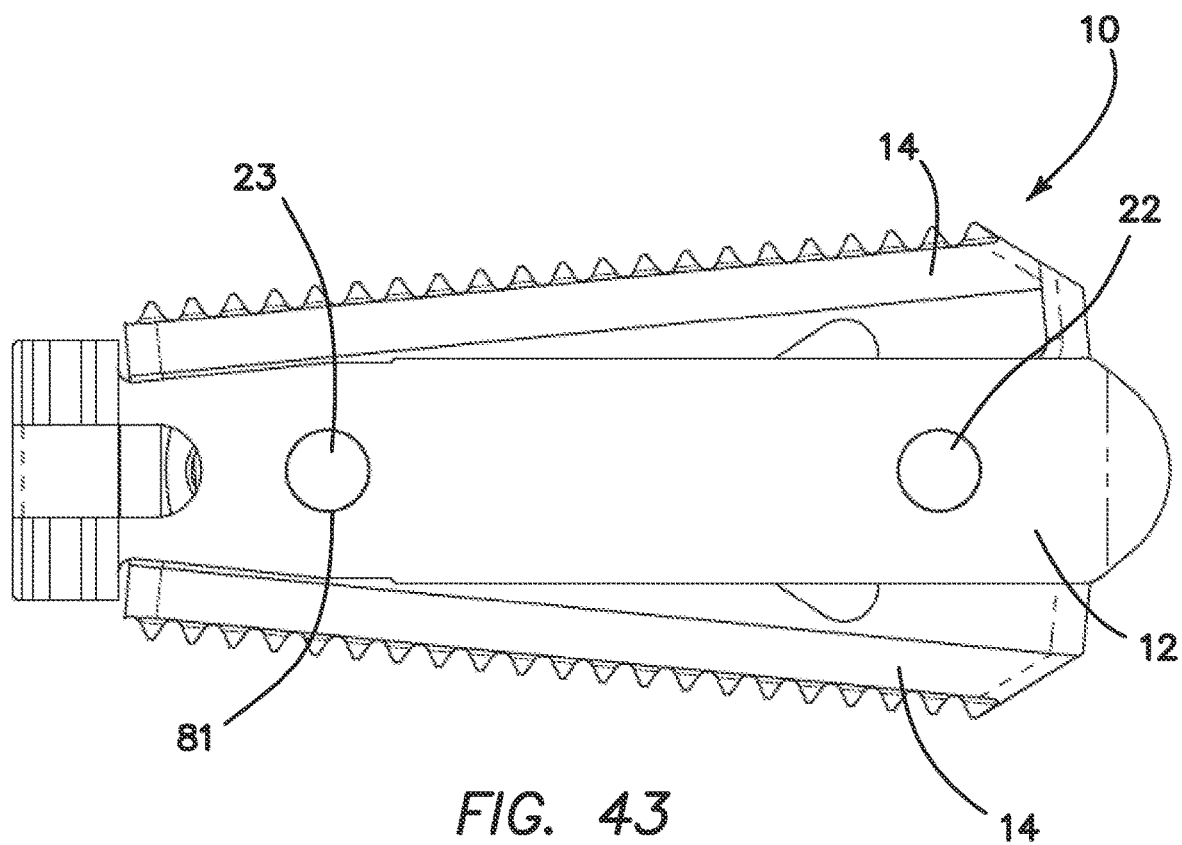
FIG. 43 is a side elevational view of the angularly expandable interbody spacer of FIG. 39.
Figure 44:
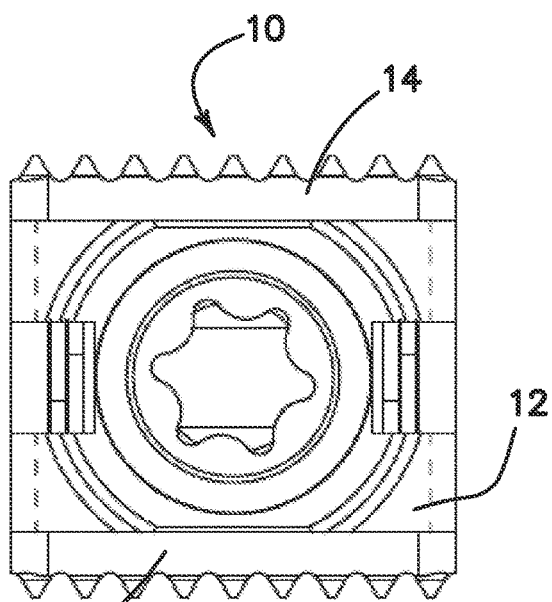
FIG. 44 is a rear elevational view of the angularly expandable interbody spacer of FIG. 38.
Figure 45:
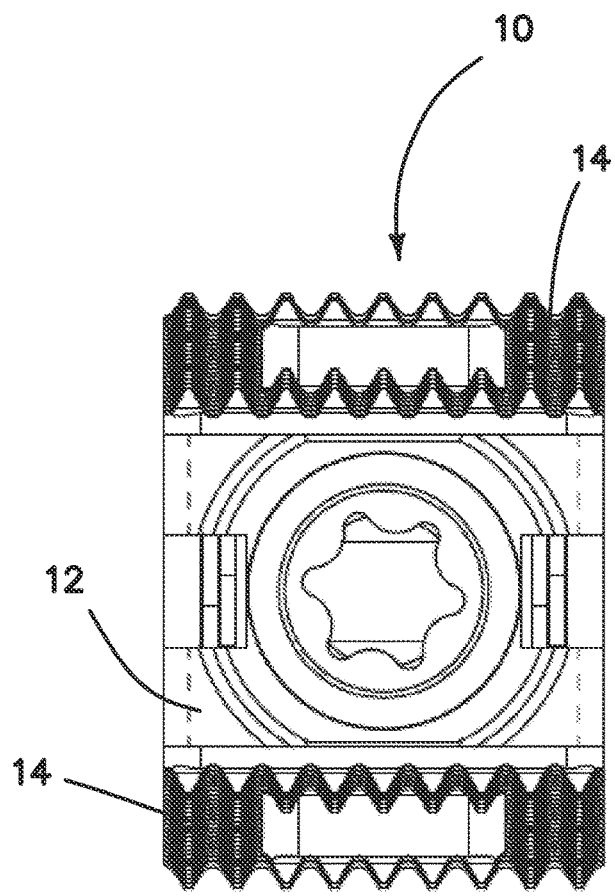
FIG. 45 is a rear elevational view of the angularly expandable interbody spacer of FIG. 39.
Figure 46:
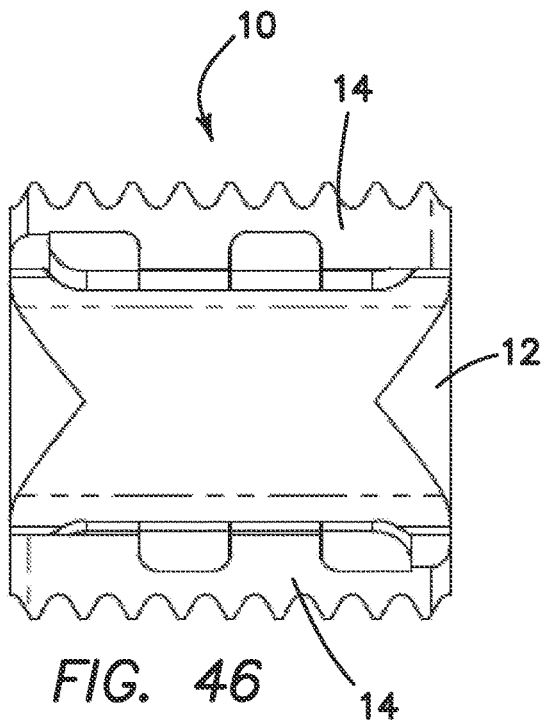
FIG. 46 is a front elevational view of the angularly expandable interbody spacer of FIG. 38.
Figure 47:
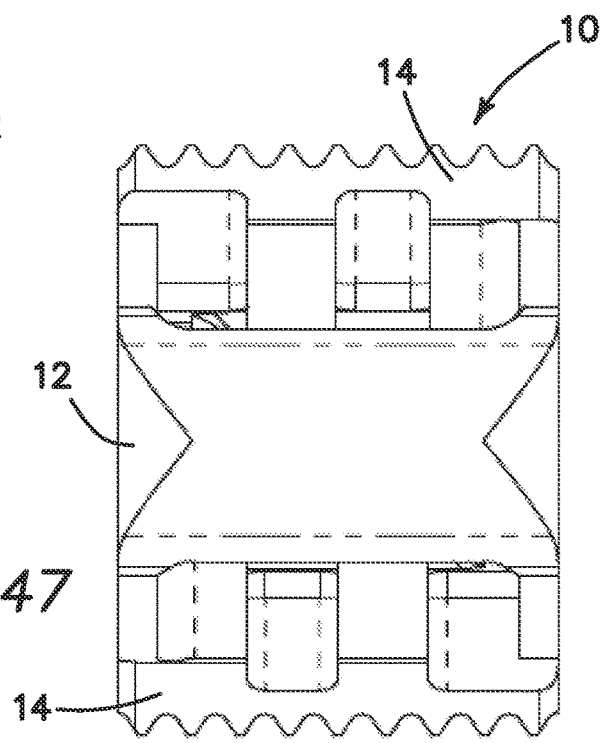
FIG. 47 is a front elevational view of the angularly expandable interbody spacer of FIG. 39.
Figure 48:
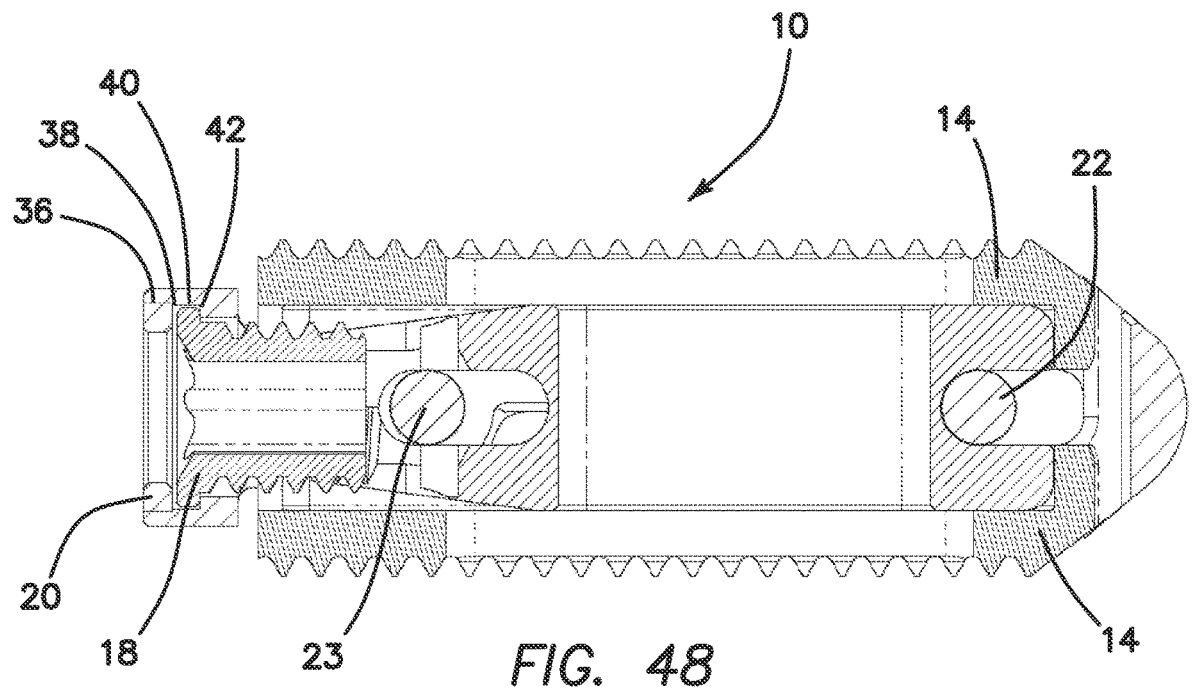
FIG. 48 is a cross-sectional view of the angularly expandable interbody spacer of FIG. 38.
Figure 49:
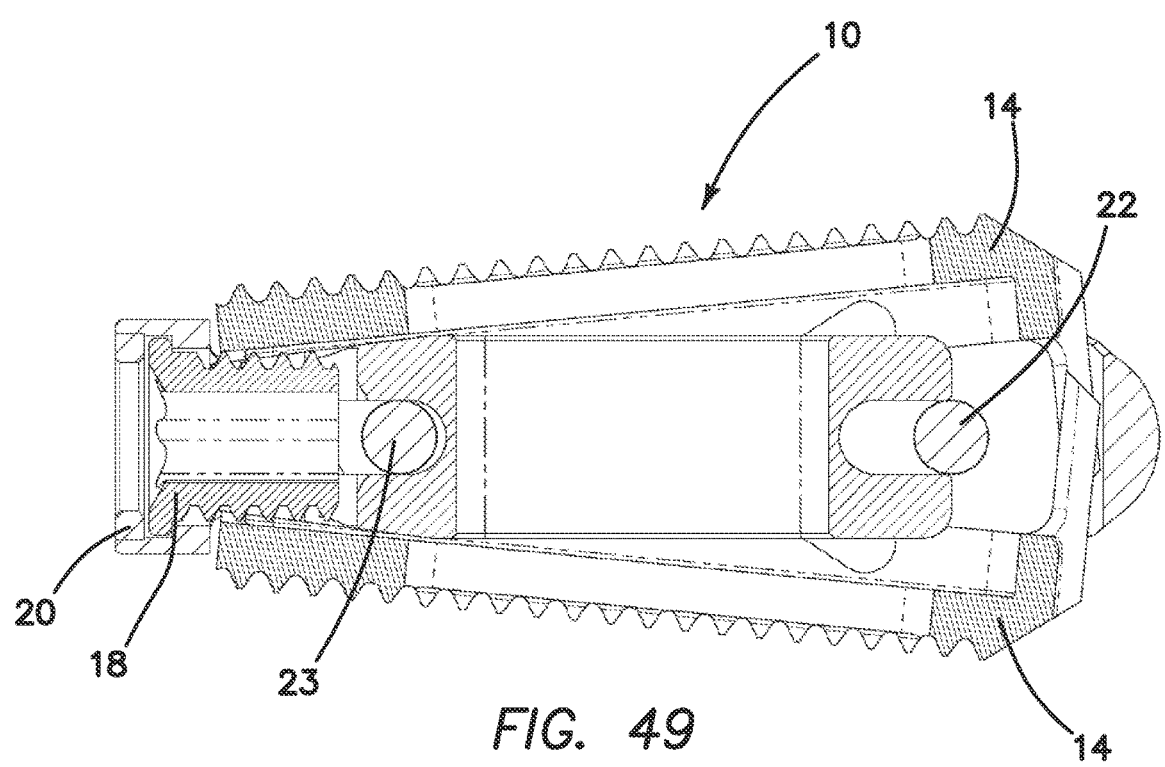
FIG. 49 is a cross-sectional view of the angularly expandable interbody spacer of FIG. 39.
Figure 52:
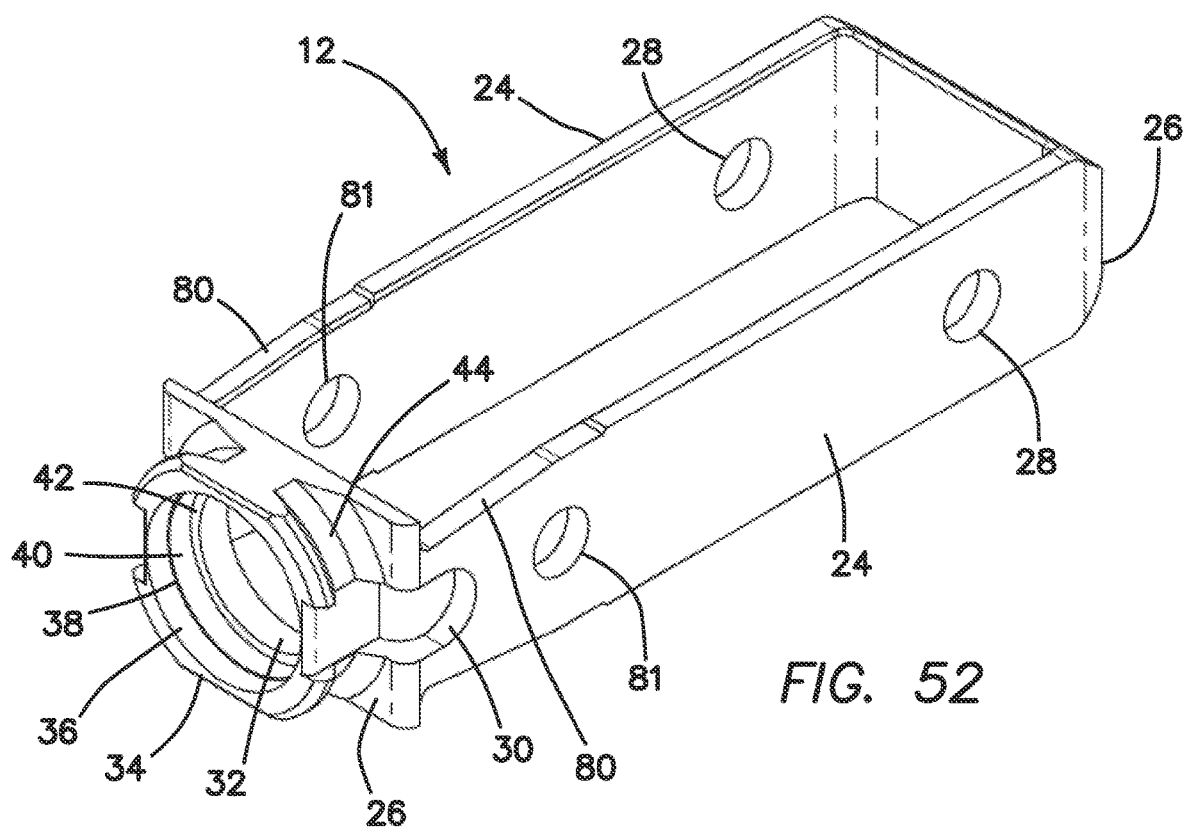
FIG. 52 is a top perspective view of a housing of an angularly expandable interbody spacer according to the present invention.
Figure 53:
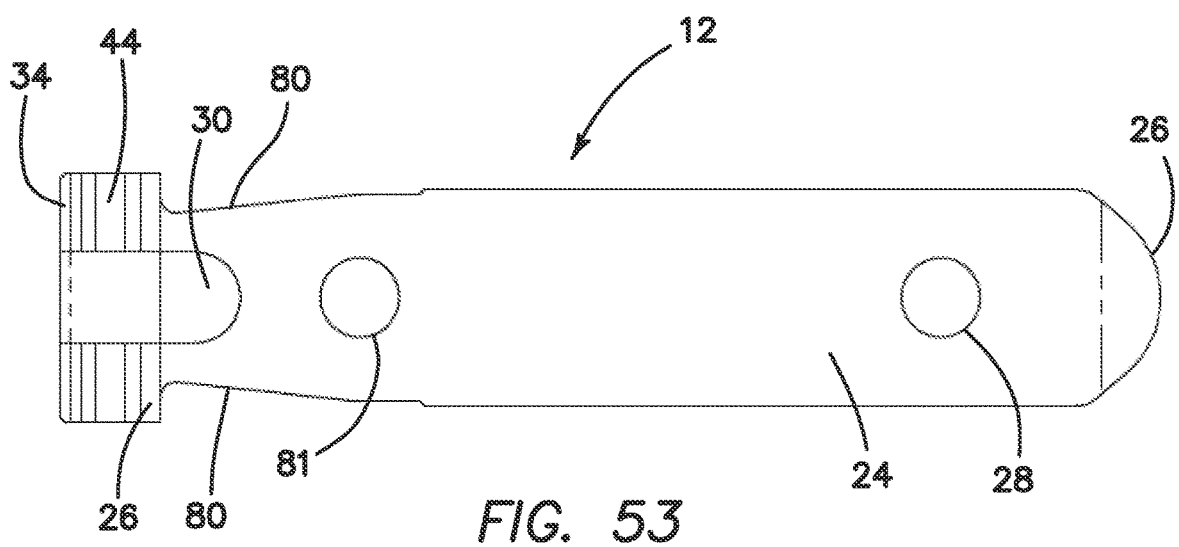
FIG. 53 is a side elevational view of the housing of FIG. 52.

Turning now to the FIGS. 52-53, the housing 12 will now be described in greater detail. The housing 12 includes two opposite sidewalls 24 interconnected by two opposite endwalls 26 that together define an interior of the housing 12. Each of the two sidewalls 24 include two pairs of apertures 28 oppositely disposed from each other. A first pair of apertures 28 is near the distal end of the housing 12 and sized and configured for receiving the alignment pin 22 of FIG. 25. A second pair of apertures 28 is near the proximal end of the housing 12 and sized and configured for receiving a pivot pin 23 which is the same as the alignment pin 22 and shown in FIG. 25. At the proximal end of the housing 12, the sidewalls 24 include oppositely disposed instrument notches 30 which serve as openings sized and configured to receive oppositely disposed distal prongs of an insertion instrument used for grasping, delivering, implanting, deploying and removing the interbody spacer 10. The sidewalls 24 are parallel to each other and of equal length. Also, the endwalls 26 are parallel to each other and of equal length. Both the sidewalls and endwalls 26 define a rectangular shaped housing 12 having an open top end and open bottom end. The top end and the bottom end are parallel to each other near the distal end and the height of the sidewalls 24 is reduced near the proximal end of the housing 12 to form a taper 80 at the top and bottom of the sidewall 24 near the proximal end. The taper 80 provides space for and permits angulation of the endplates 14 about the pivot pin 23 as can be seen clearly in FIG. 43. The front distal endwall 26 is curved, tapered, angled or peaked to define a leading ramp-like surface for easily penetrating into the disc space. The rear endwall 26 includes a cylindrical-like collar 34 extending proximally and defining a rear opening 32 that opens to the interior of the housing 12. The rear opening 32 is configured for accessing the proximal end of the locking screw 18 of FIG. 23 that is connected to the housing 12 in the location of the collar 34. The proximal end of the locking screw 18 is provided with an instrument-engaging socket 45. With particular reference to FIG. 52, the inner surface of the collar 34 defines a first recess 36 for receiving the locking ring 20 of FIG. 24. The first recess 36 may include a first ledge 38 to provide a stop for the locking ring 20 when connected to the collar 34. The inner surface of the collar 34 also includes a second recess 40. The second recess 40 is sized and configured to receive the proximal end of the locking screw 18. The second recess 40 may include a second ledge 42 such that the proximal end of the locking screw 18 is retained in the second recess 40 between the second ledge 42 at the distal end and first ledge 38 and the locking ring 20 at the proximal end such that the locking screw 18 is permitted to rotate with respect to the housing 12 without translating with respect to the housing 12 or falling out of the housing 12. The recesses 36, 40 and ledges 38, 42 are also shown in FIG. 38.

Furthermore, the outer surface of the collar 34 includes oppositely disposed lateral flats for providing easy and direct access for an insertion instrument for connected to the adjacent instrument notches 30. Top and bottom flats are also provided to give the collar 34 a low-profile height. The outer surface of the collar 34 includes a ring-shaped outer recess 44.

Figure 50:
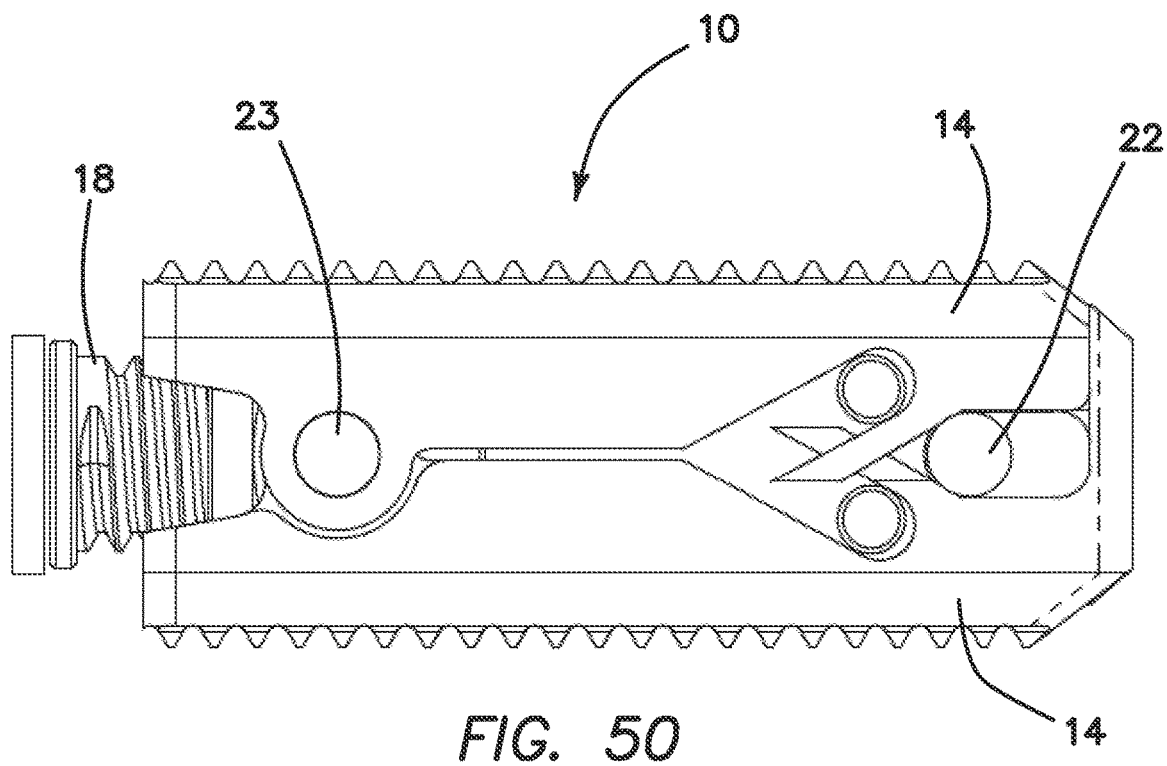
FIG. 50 is a side elevational view of the angularly expandable interbody spacer of FIG. 38 without a housing.
Figure 54:
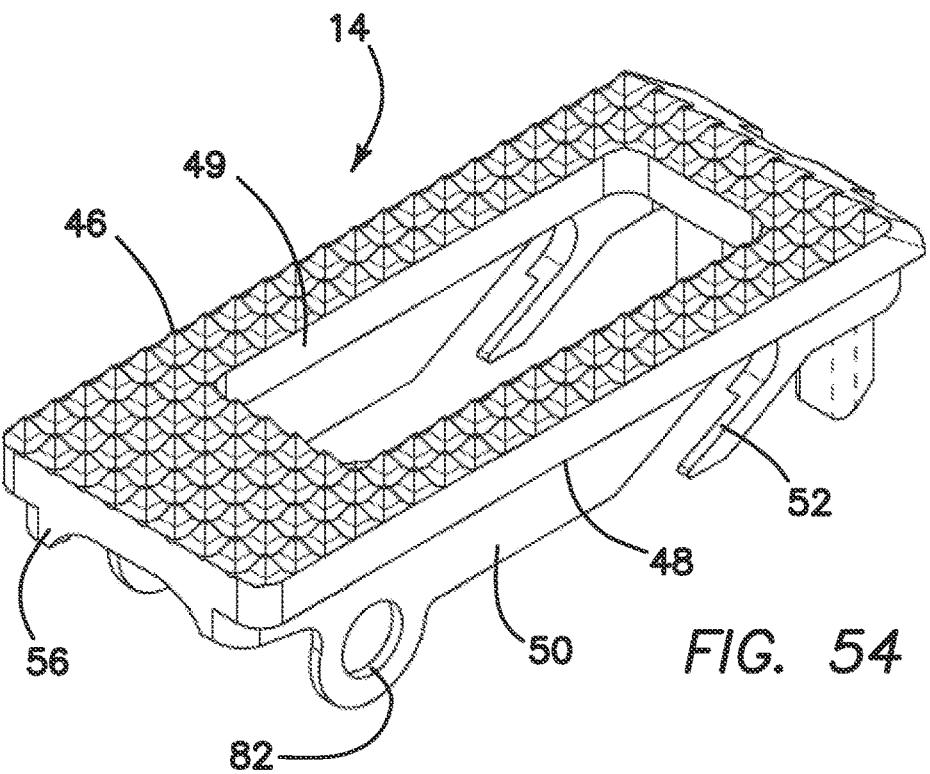
FIG. 54 is a rear top perspective view of an endplate of an angularly expandable interbody spacer according to the present invention.
Figure 55:
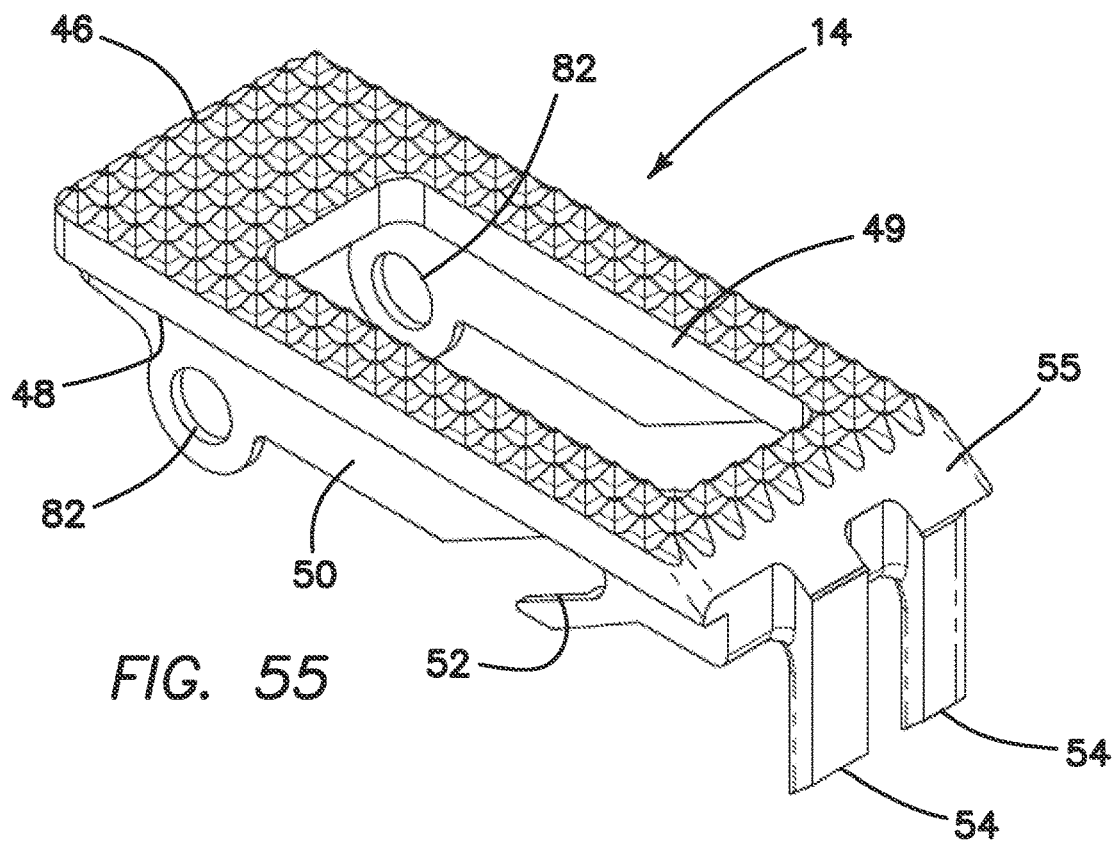
FIG. 55 is a front top perspective view of the endplate of FIG. 54.
Figure 56:
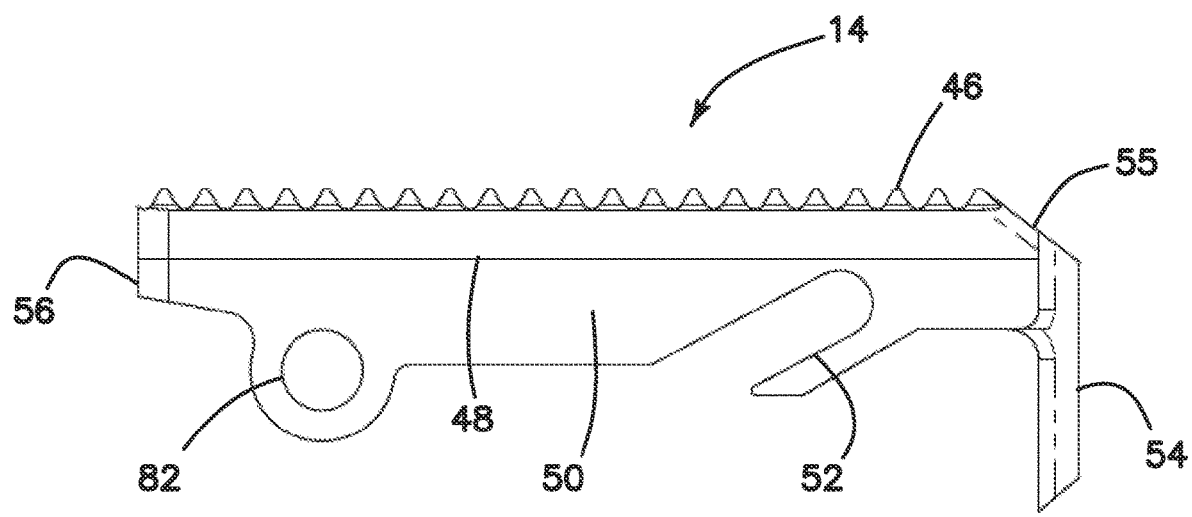
FIG. 56 is a side elevational view of the endplate of FIG. 54.
Figure 57:
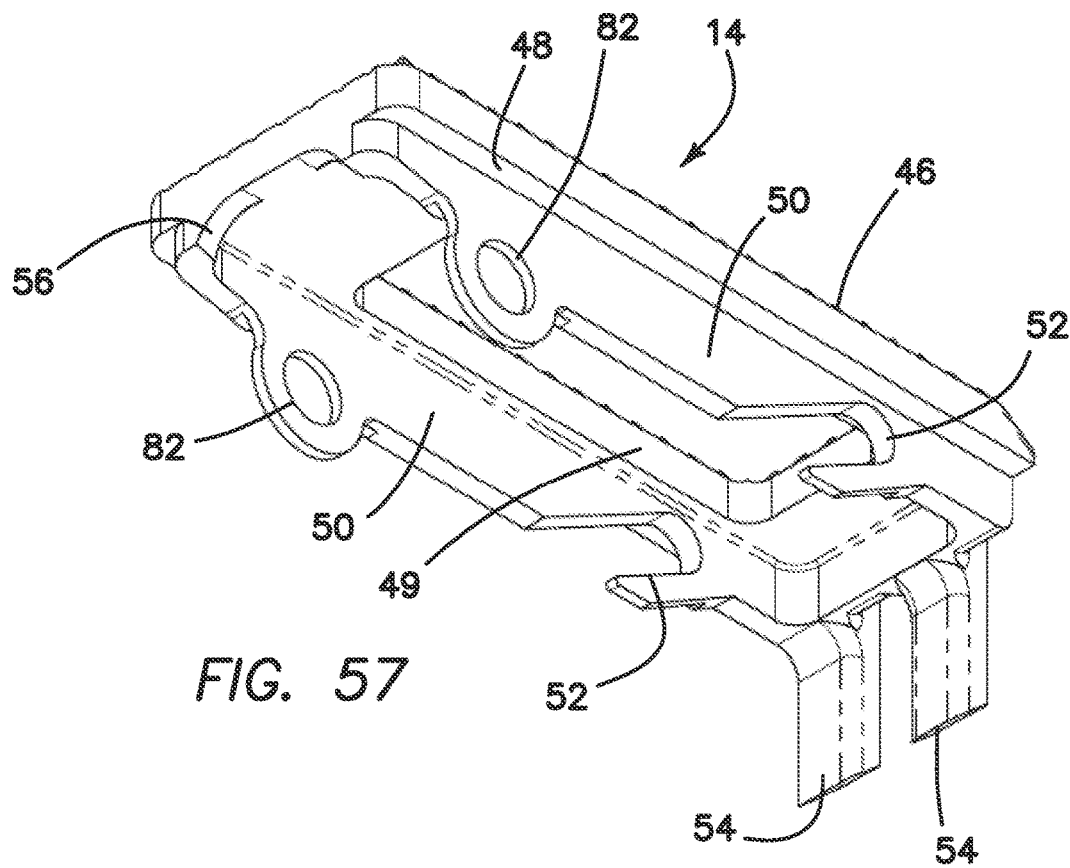
FIG. 57 is a bottom perspective view of the endplate of FIG. 54.

Turning now to FIGS. 54-57, the top and bottom endplates 14 will now be described. The top and bottom endplates 14 are identical and are connected to the housing 12 via the actuator 16. Each endplate 14 has a bone-engaging surface 46 and an interior surface 48. The bone-engaging surface 46 includes a plurality of tooth-like ridges. The ridges have pointed peaks to engage and increase the purchase on the adjacent vertebra between which the implant is located. The ridges may further be angled to help hold and prevent migration of the spacer 10 relative to the adjacent vertebrae when implanted within the intervertebral space. The endplate 14 further includes a leading surface 55 that does not have tooth-like projections like the bone-engaging surface 46. The leading surface 55 serves as an extension of the leading ramp-like surface at the distal end of the housing 12 for easily penetrating and distracting the disc space as the spacer 10 is inserted. The angle between the leading surface 55 and the bone-engaging surface 46 is equal to or greater than 90 degrees. Each endplate 14 includes at least one endplate opening 49 extending between the bone-engaging surface 46 and the interior surface 48. The endplate opening 49 reduces the weight of the spacer 10 and permits bone ingrowth to take place into the endplate 14. A family of bone graft materials, such as autograft, bone morphogenic protein (BMP), bone marrow aspirate, concentrate, stem cells and the like, may be placed inside the endplate openings 49 and into the interior of the housing 12 to promote bone growth into the spacer 10. The endplates 14 have a width that is equal to the overall width of the spacer 10 and equal to the width of the housing 12. The interior surface of the endplates 14 includes two oppositely-disposed and parallel side rails 50. The side rails 50 include oppositely disposed and parallel, angled ramped notches 52 along the length of the side rails 50. One ramped notch 52 is shown in FIGS. 54-57. All of the ramped notches 52 have the same angle with respect to the interior surface 48 and are configured for receiving and engaging correspondingly sized and shaped ramps of the actuator 16. As can be seen in FIG. 54, the ramped notches 52 are offset to one side such that when one is inverted with respect to the other they can overlap as shown in FIG. 50. The interior surface 48 includes two projections 54 at the distal end and a proximal endwall 56 that is curved to accommodate the proximal end of the actuator 16. The two projections 54 of the top endplate 14 interdigitate with the two projections 54 of the bottom endplate 14 as can be best seen in FIGS. 46-47 wherein the channel-like spaces between the projections 54 of the top endplate 14 are sized and configured to receive the projections 54 of the bottom endplate 14 and vice versa. The side rails 50 further include two oppositely disposed circular openings 82 sized and configured to receive the pivot pin 23 such that the endplates 14 are permitted to angulate about the pivot pin 23 when deployed from a low-profile configuration to a high-profile configuration. The circular openings 82 are also offset slightly to one side such that can overlap each other as shown in FIG. 50.

Figure 58:
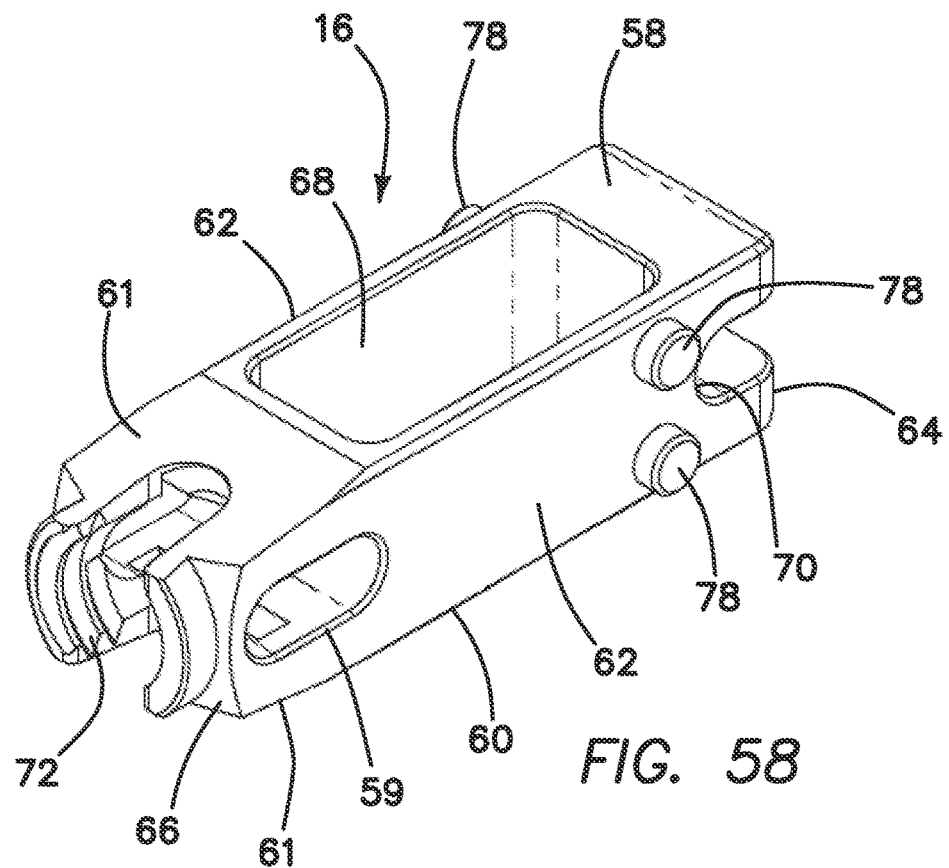
FIG. 58 is a rear top perspective view of an actuator of an expandable interbody spacer according to the present invention.
Figure 59:
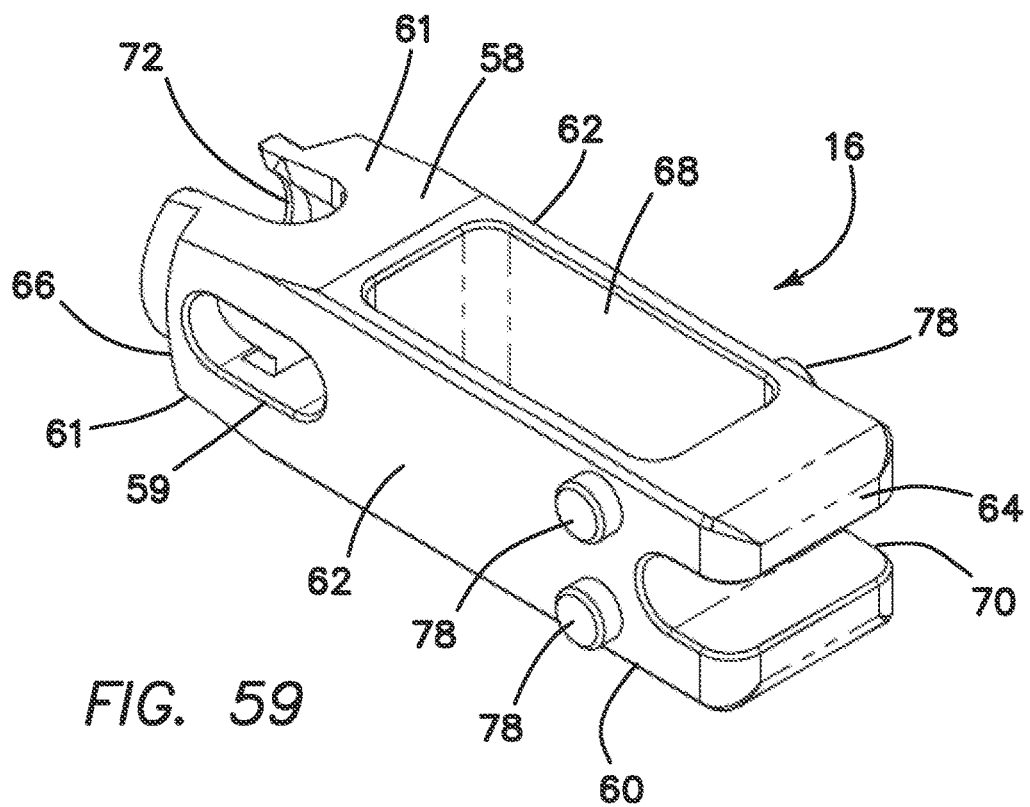
FIG. 59 is a front top perspective view of the actuator of FIG. 58.
Figure 60:
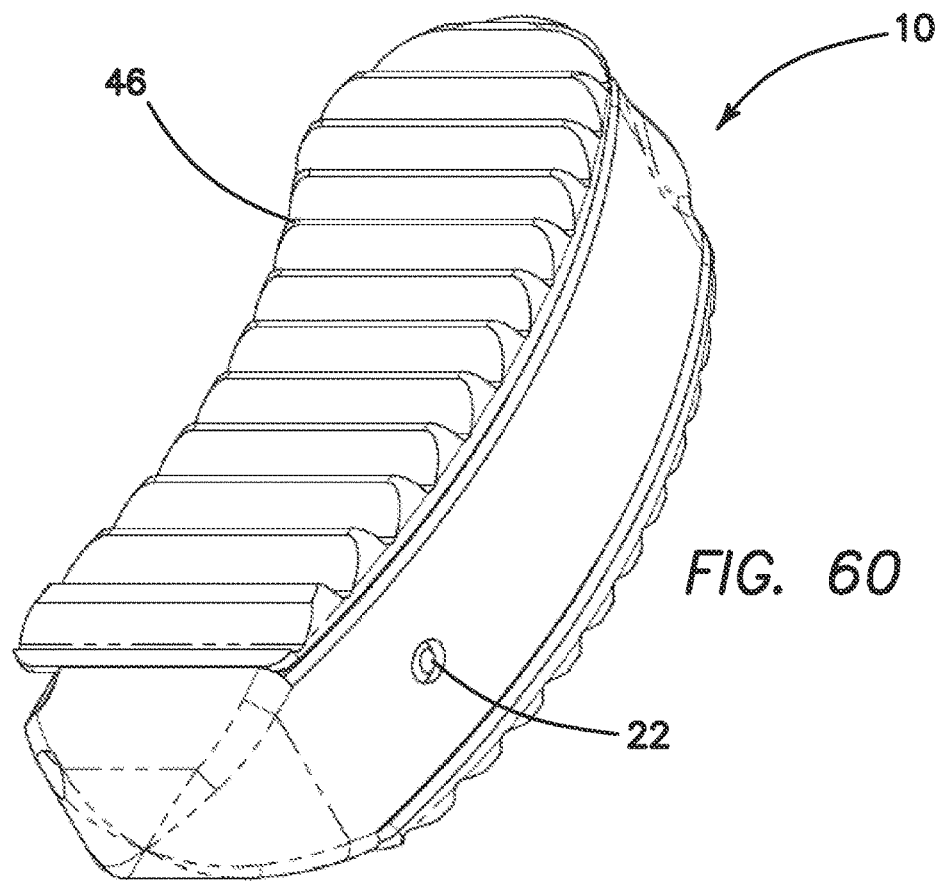
FIG. 60 is a front top perspective view of a banana-shaped expandable interbody spacer in its low-profile configuration according to the present invention.
Figure 61:
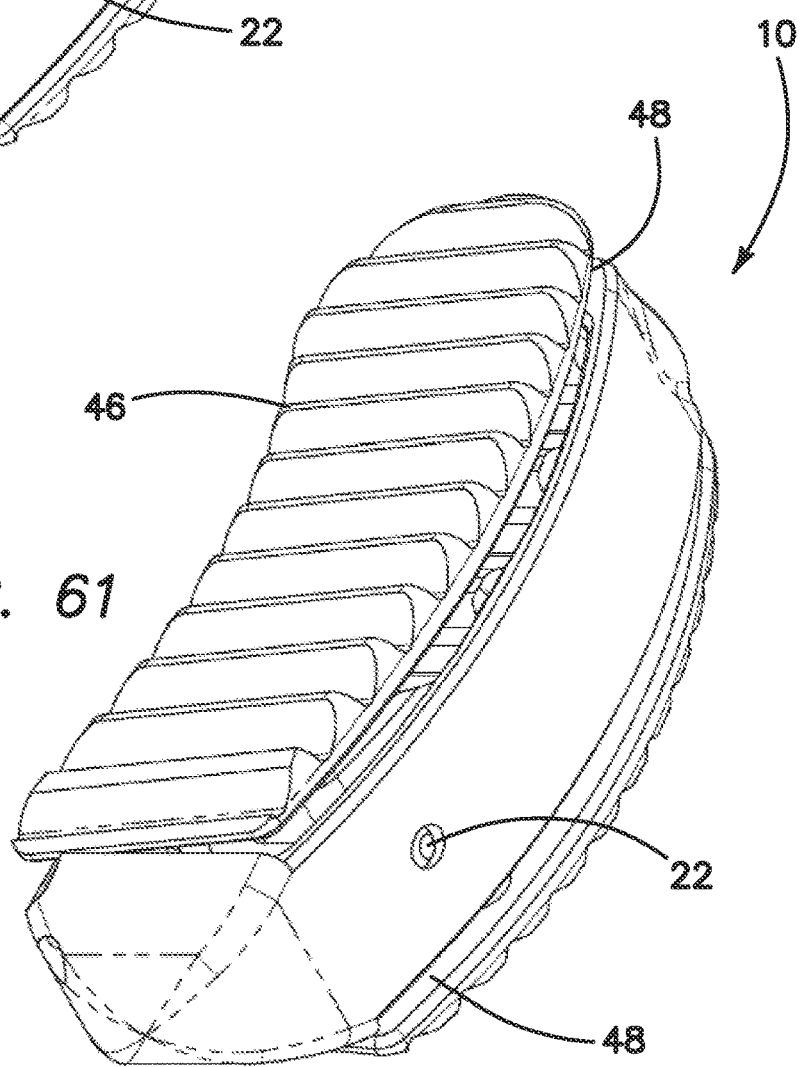
FIG. 61 is a front top perspective view of a banana-shaped expandable interbody spacer of FIG. 60 in its expanded configuration according to the present invention.
Figure 62:
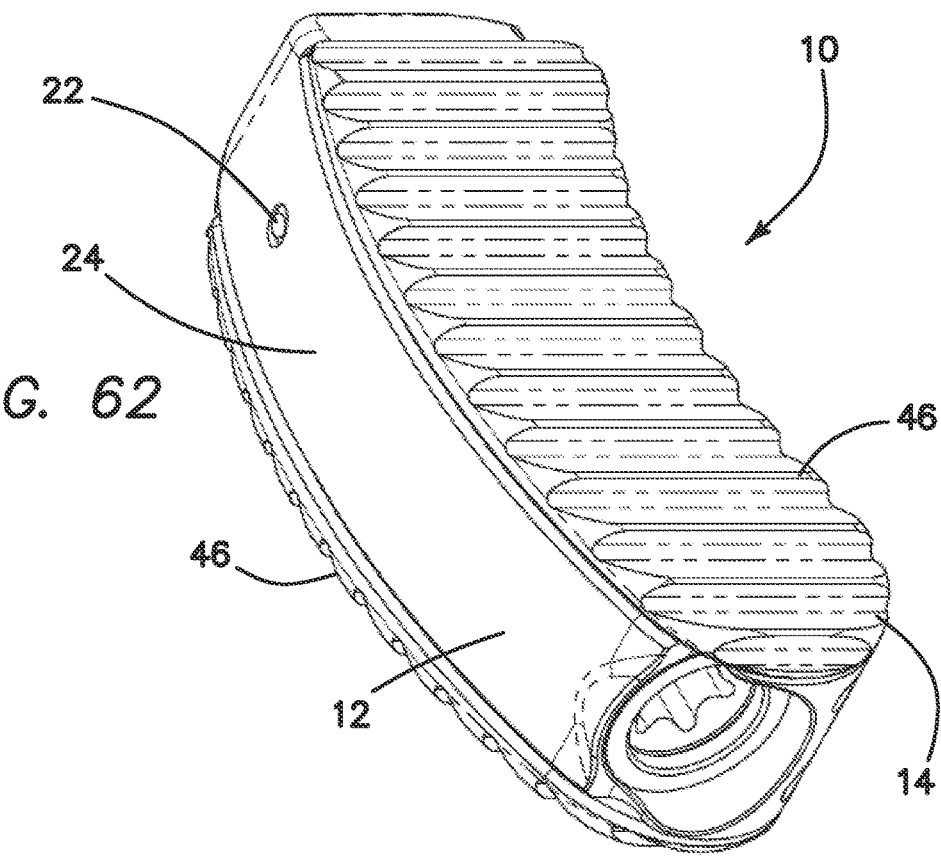
FIG. 62 is a rear top perspective view of the expandable interbody spacer of FIG. 60.
Figure 63:
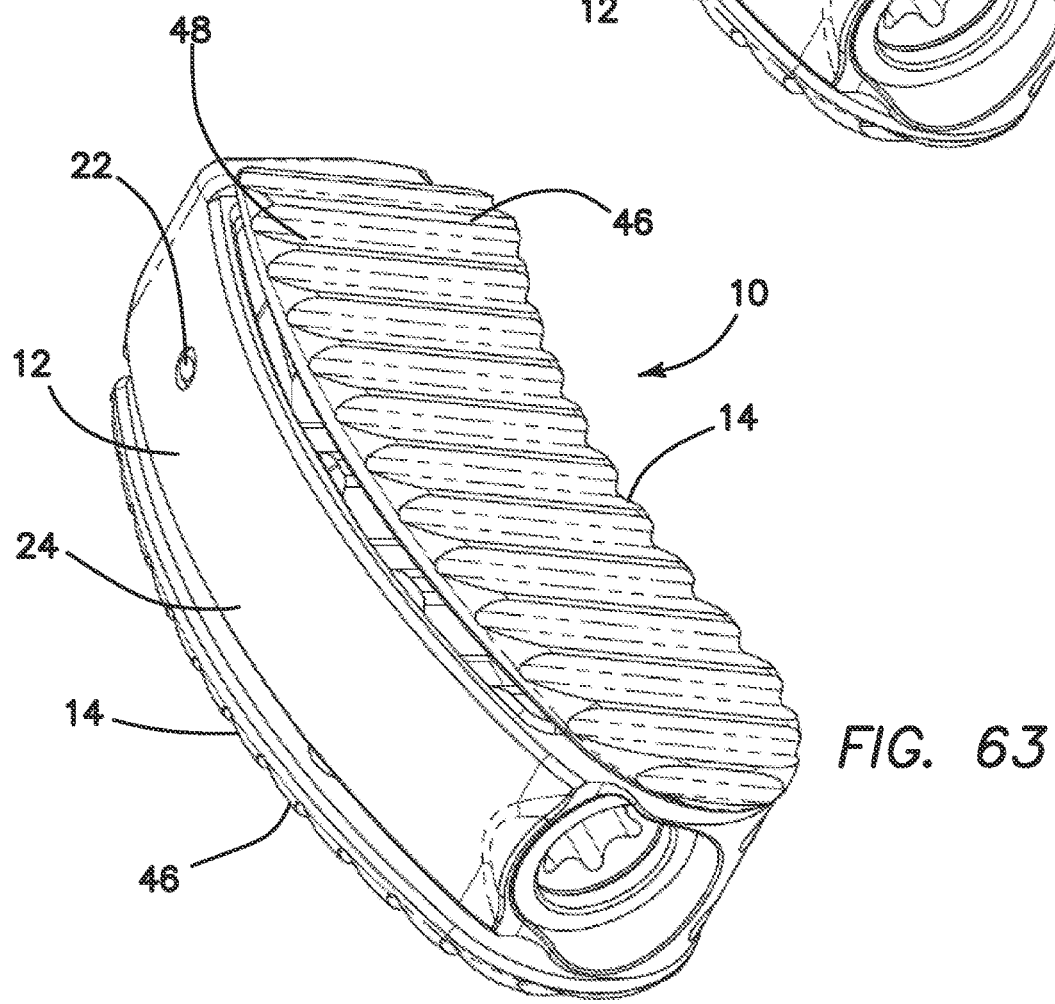
FIG. 63 is a rear top perspective view of the expandable interbody spacer of FIG. 61
Figure 64:
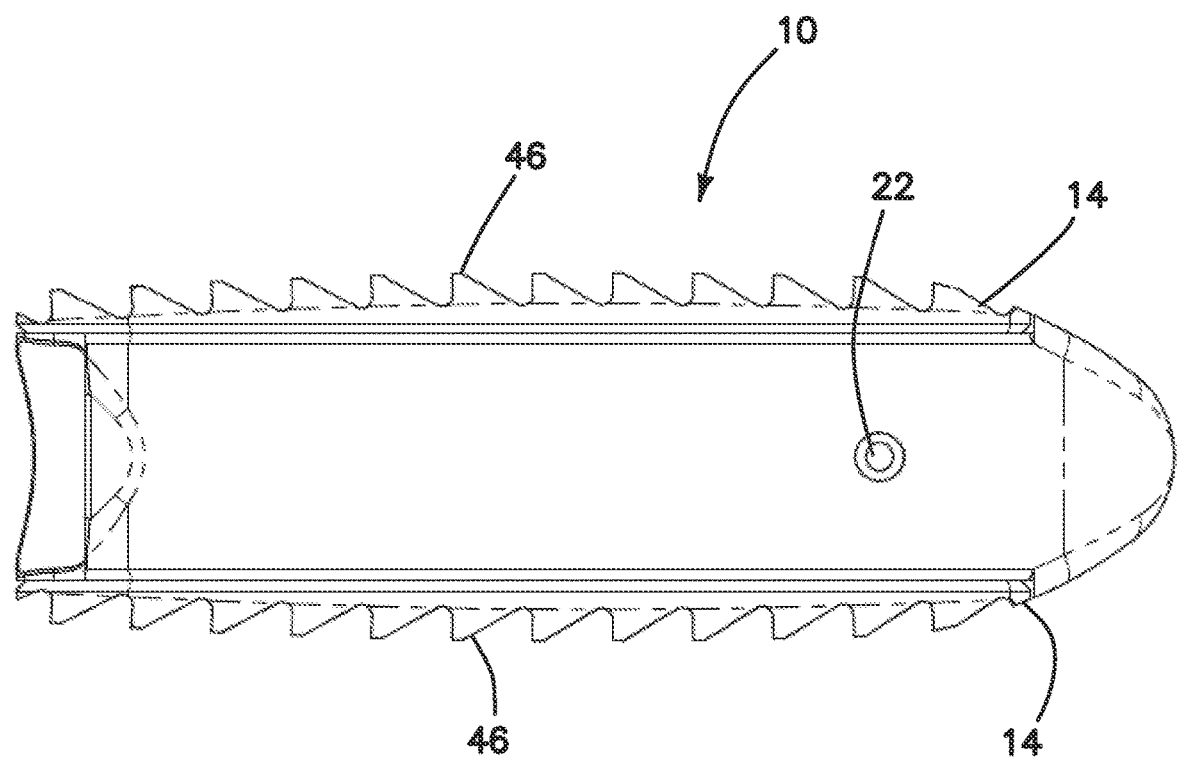
FIG. 64 is a side elevational view of the expandable interbody spacer of FIG. 60.
Figure 65:
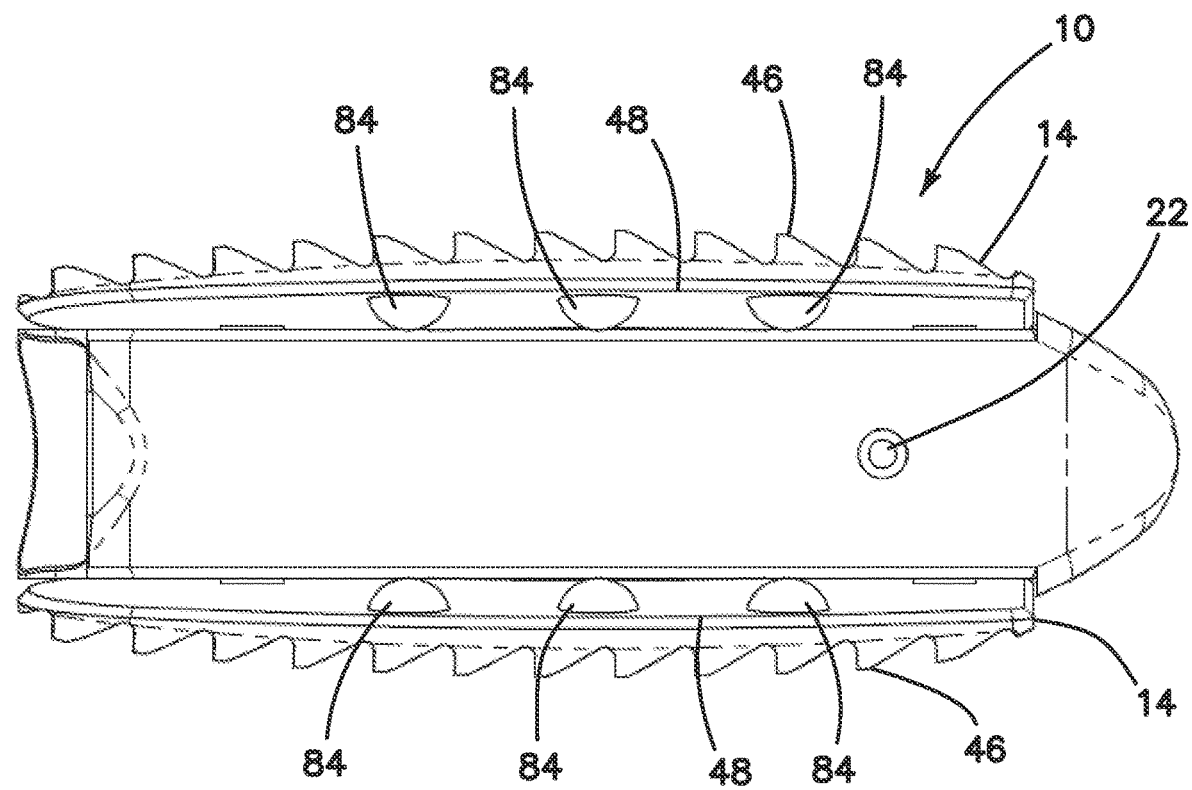
FIG. 65 is a side elevational view of the expandable interbody spacer of FIG. 61.
Figure 66:
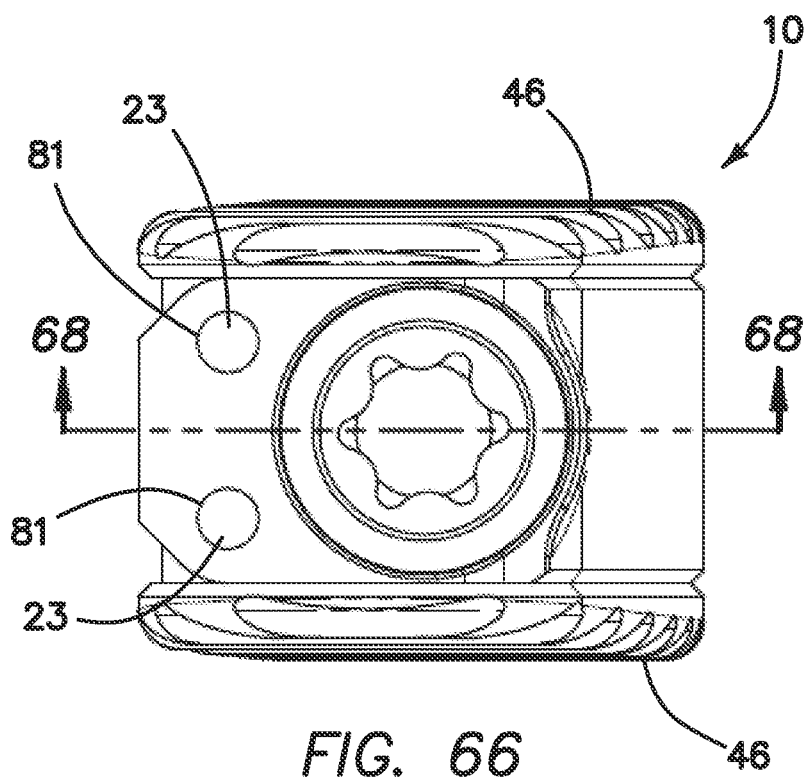
FIG. 66 is a rear elevational view of the expandable interbody spacer of FIG. 60.
Figure 67:
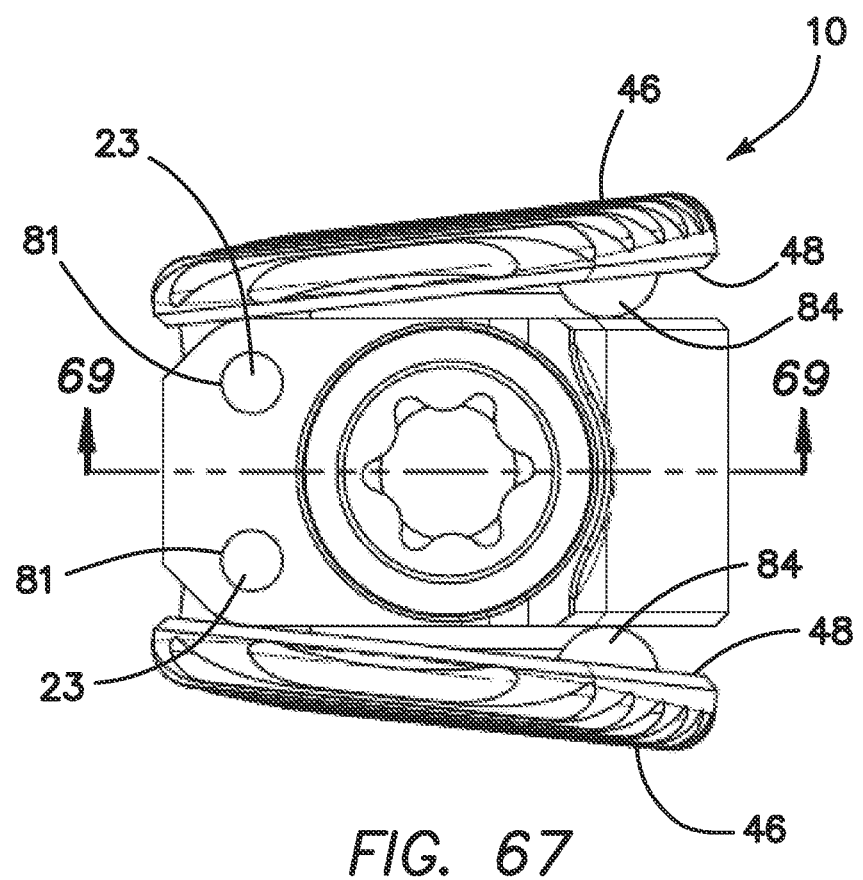
FIG. 67 is a rear elevational view of the expandable interbody spacer of FIG. 61.

Turning now to FIGS. 58-59, the actuator 16 will now be described. The actuator 16 is located between the two endplates 14 and inside the interior of the housing 12. The actuator 16 includes two sidewalls 62 interconnected by a top wall 58, bottom wall 60, a front wall 64 and a back wall 66. The actuator 16 is rectangular-like in shape and conforms to the rectangular-like shape of the interior of the housing 12. The actuator 16 includes an actuator opening 68 extending between the top wall 58 and bottom wall 60. The actuator opening 68 reduces the weight of the spacer 10 and permits bone ingrowth to take place in through the endplate openings 49 and into the actuator opening 68. A family of bone graft materials, such as autograft, bone morphogenic protein (BMP), bone marrow aspirate, concentrate, stem cells and the like, may be placed inside the actuator opening 68 to promote bone growth into the spacer 10. The front wall 64 of the actuator 16 includes an alignment channel 70 sized and configured to receive the alignment pin 22. The alignment channel 70 extends along the front wall 64 and between the two sidewalls 62. The back wall 66 includes a threaded opening 72 sized and configured for threaded engagement with the locking screw 18. The actuator 16 further includes an elongated pivot slot 59 that has a longitudinal axis that is aligned with the longitudinal axis of the actuator 16. The pivot slot 59 extends between the two sidewalls 62 and is sized and configured to receive the pivot pin 23. The pivot slot 59 is also aligned with apertures 28 of the housing 12 through which the pivot pin 23 extends. The proximal end of the top wall 58 and the bottom wall 60 includes a taper surface 61 giving the actuator 16 a gradually decreasing height towards the proximal end. The taper 61 matches the taper 80 of the housing 12 to accommodate the angulation of the endplates 14 in a high-profile configuration. Each sidewall 62 includes a pair of cylindrical projections 78 positioned vertically transverse to the longitudinal axis of the actuator 16 and near the distal end. The two projections 78 near the top wall 58 are sized and configured to engage and move within the ramped notches 52 of the top endplate 14. The two projections 78 near the bottom wall 60 are sized and configured to engage and move within the ramped notches 52 of the bottom endplate 14. The cylindrical projections 78 extend laterally outwardly from the sidewall 62. Even though the projections 78 are cylindrical any shaped driving surface capable of performing the same function is within the scope of the present invention.

The expandable interbody spacer 10 of FIGS. 38-59 is assembled by first connecting the endplates 14 to the actuator 16. The projections 78 of the actuator 16 are inserted into the ramped notches 52 of the both the top and bottom endplates 14. This subassembly is inserted into the interior of the housing 12 and the alignment pin 22 is inserted through the alignment pin apertures 28 of the housing 12 and the pivot pin 23 is inserted through the pivot slot 59. The locking screw 18 is inserted through the rear opening 32 of the housing 12 and into the threaded opening 72 of the actuator 16. The locking ring 20 is inserted in through the rear opening 32 and into the collar 34 of the housing 12 and welded thereto where it prevents the locking screw 28 from backing out of the housing 12.

Figure 51:
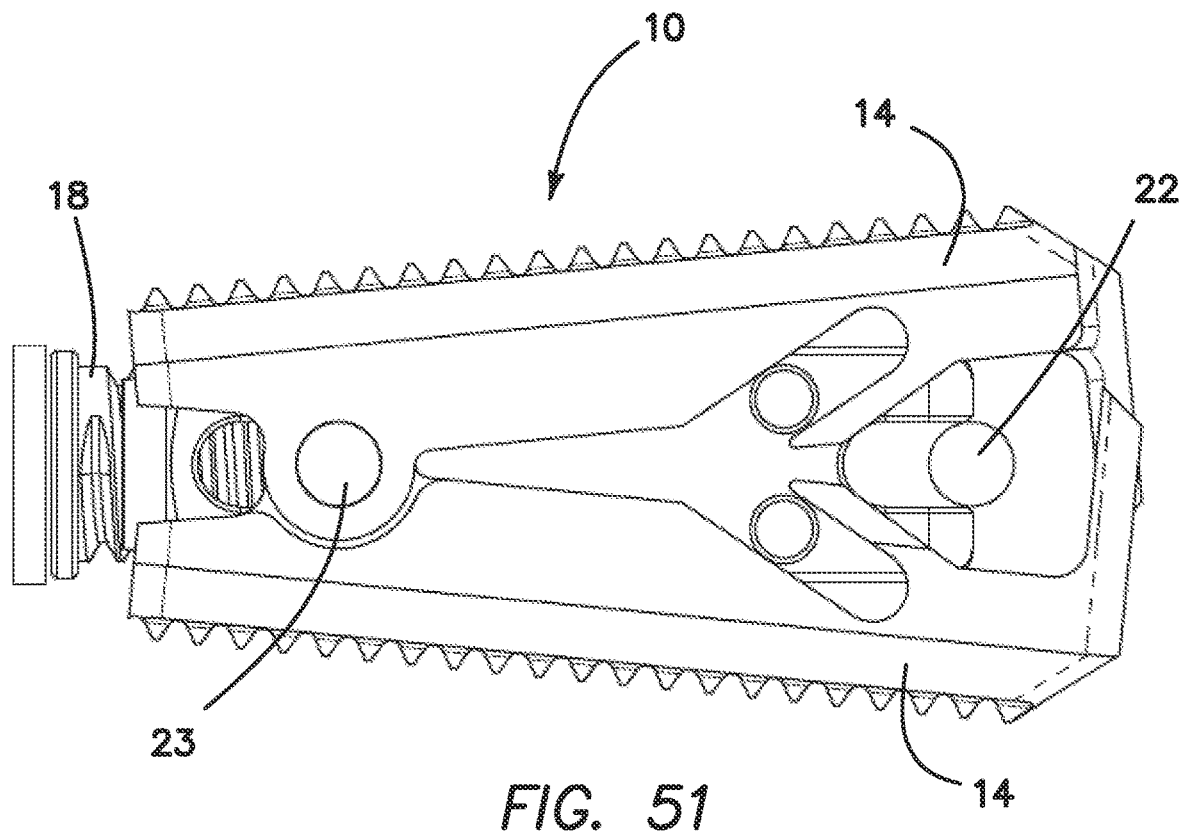
FIG. 51 is a side elevational view of the angularly expandable interbody spacer of FIG. 39 without a housing.

In use, the present expandable interbody spacer 10 is inserted into the disc space between adjacent vertebral bodies. The spacers 10 of FIGS. 38-59 are generally configured for use as a PLIF cage in spinal surgical procedures. Similarly to the expandable spacers 10 described with respect to FIGS. 1-38, an insertion instrument is connected at the proximal end of the spacer 10 such that it is secured to the collar 34, for example, by engaging the insertion instrument around the outer recess 44. The insertion instrument includes a drive mechanism that is configured to engage the socket 45 of the locking screw 18. The surgeon uses the insertion instrument to grasp the spacer 10 and place it at the mouth of the intervertebral space in its low-profile configuration. The spacer 10 is moved and orientated into its proper position within the intervertebral space. As the spacer 10 is moved within the vertebral space, the distal endwall 26, which is ramped, facilitates insertion and distraction of the vertebral bodies. Also, the leading surface 55 of the endplate 14 further facilitates wedging the spacer 10 into position. The spacer 10 is placed such that the top endplate 14 contacts the lower endplate of the upper vertebral body and the bottom endplate 14 of the spacer 10 contacts the upper endplate of the lower vertebral body on either side of the target intervertebral space. When the spacer 10 is in position, the insertion instrument is used to deploy the spacer 10 into its expanded or high-profile configuration. The insertion instrument is configured to rotate the locking screw 18 in one of a first clockwise or counter-clockwise direction. Rotation of the locking screw 18 in a first direction results in translation of the actuator 16 in a proximal direction relative to the housing 12 as can be seen in FIGS. 50-51. Other than rotation about its longitudinal axis, the locking screw 18 remains stationary with respect to the housing 12. As the actuator 16 moves proximally relative to the housing 12, the projections 78 slide against the ramped notches 52 of the endplates 14 moving both the top and bottom endplates 14 down along the ramps 74 and outwardly into angular expansion that is proportional to the degree of rotation of the locking screw 18. The surgeon can adjust the distance/height of expansion of the distal ends of the endplates 14 by rotating the locking screw 18 clockwise or counter-clockwise as needed according to surgeon preference and patient anatomy. Rotation of the locking screw 18 in one of a second clockwise or counter-clockwise direction opposite to the first direction, the distance of angular expansion of the endplates 14 is reduced in direct proportion to degree of rotation in the second direction. Hence, the surgeon can increase or reduce the height of the spacer 10 as needed to not only facilitate placement of the spacer 10 but also to obtain optimum and customized distraction of the vertebral space for the patient. Angular expansion is achieved because the proximal ends of the endplates 14 are pinned with the pivot pin 23 forcing angulation of the endplates 14 about the pivot pin 23. The degree of angulation in moving from a low-profile configuration to a high-profile configuration is approximately between zero and 30 degrees. The tapers 61, 80 spatially accommodate the angulation of the endplates 14 relative to the actuator 16 and housing 12 such that the distal end of the spacer 10 increases in height as the endplates 14 simultaneously angulate into the high-profile configuration. The angular expansion aids in restoring the natural lordotic curvature of the spine segment. Similar to the spacers 10 described above, the longitudinal length of the spacer 10 remains the same before expansion and after expansion and, therefore, does not result in the locking screw 18 protruding outwardly beyond the perimetrical footprint in the longitudinal direction of the spacer 10 and potentially impinging on surrounding tissue or interfering spatially with bone ingrowth around the spacer 10. After the spacer 10 is properly positioned, the insertion instrument is detached and removed from the operating field. Further advantageously, the top and bottom endplates 14 do not translate proximally or distally along the longitudinal direction when going from the low-profile configuration to the high-profile configuration and vice versa. Therefore, the endplates 14 advantageously do not protrude distally or proximally beyond the perimetrical footprint in the longitudinal direction of the spacer and, therefore, spacer 10 prevents impingement of the surrounding tissue and nerves. Because the spacer 10 does not change in length in going between the low-profile and high-profile configurations, implantation of the spacer 10 is facilitated for the surgeon who does not have to compensate for an increase in length or location of contact with the vertebral bodies when positioning the spacer 10. Also, advantageously, the spacer 10 of the present invention angulates uniformly, simultaneously and bilaterally along the latitudinal direction which is transverse to the longitudinal axis of the spacer 10, thereby, providing greater stability to the spinal column.

Figure 6:
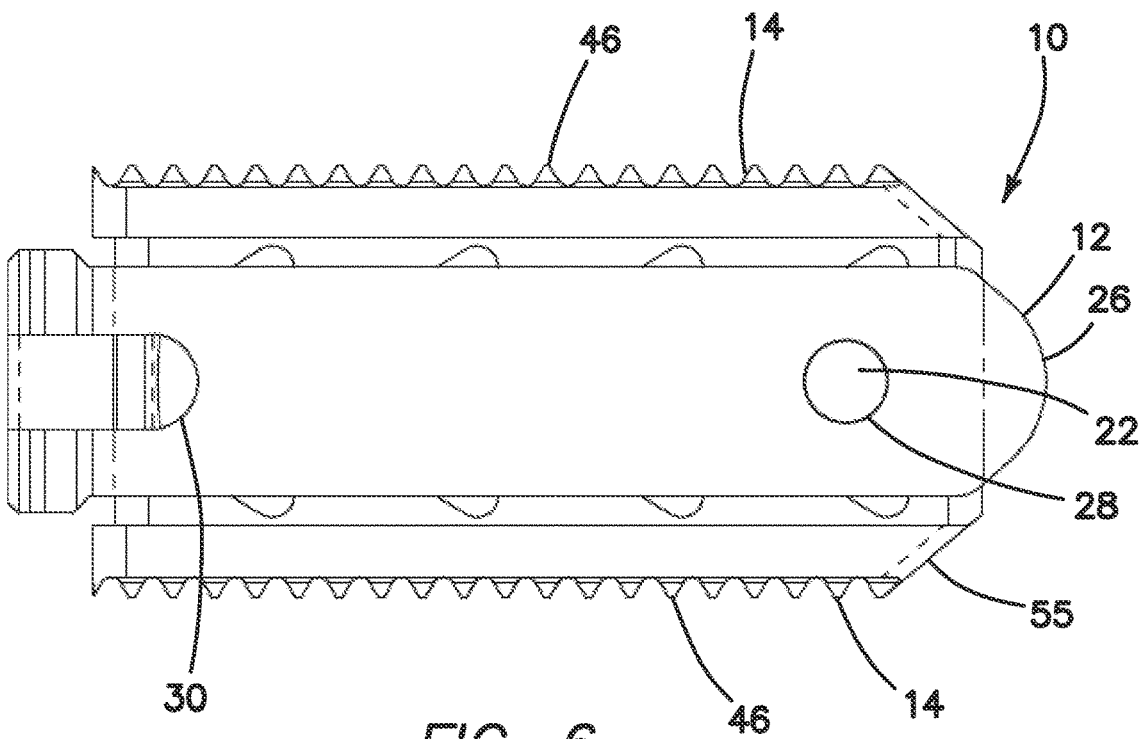
FIG. 6 is a side elevational view of the expandable interbody spacer of FIG. 2.
Figure 7:
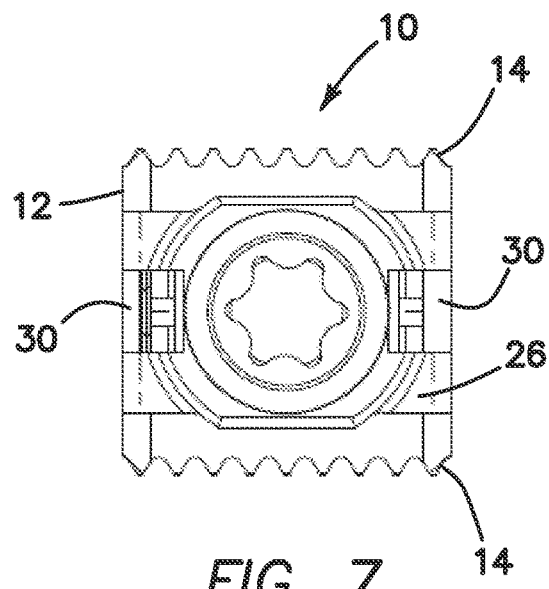
FIG. 7 is a rear elevational view of the expandable interbody spacer of FIG. 1.
Figure 8:
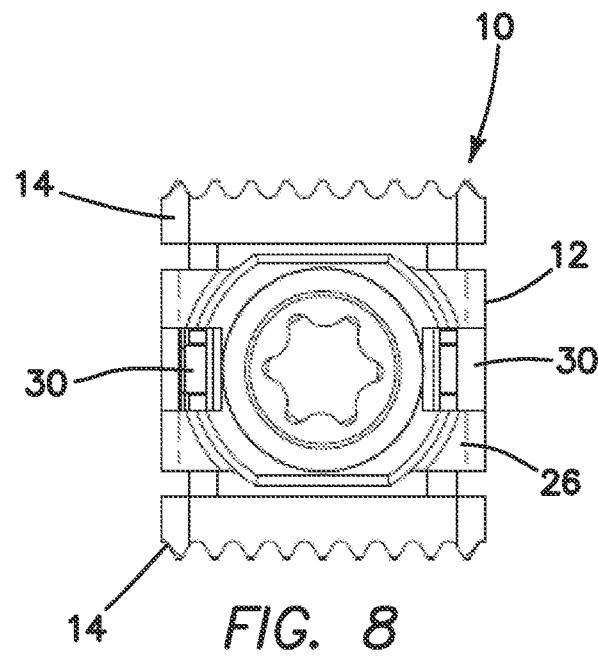
FIG. 8 is rear elevational view of the expandable interbody spacer of FIG. 2.
Figure 9:
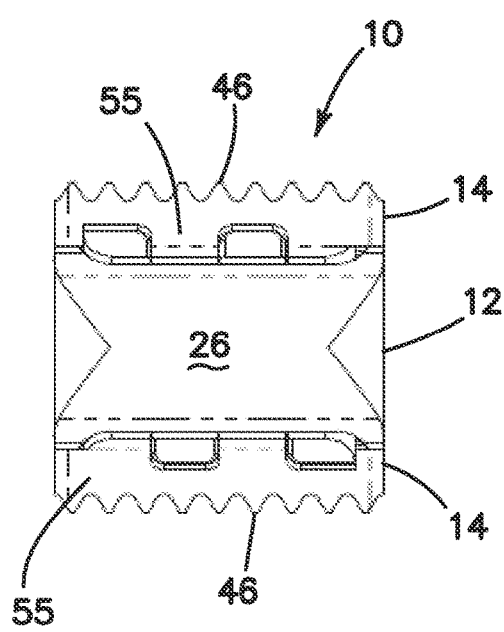
FIG. 9 is a front elevational view of the expandable interbody spacer of FIG. 1.
Figure 10:
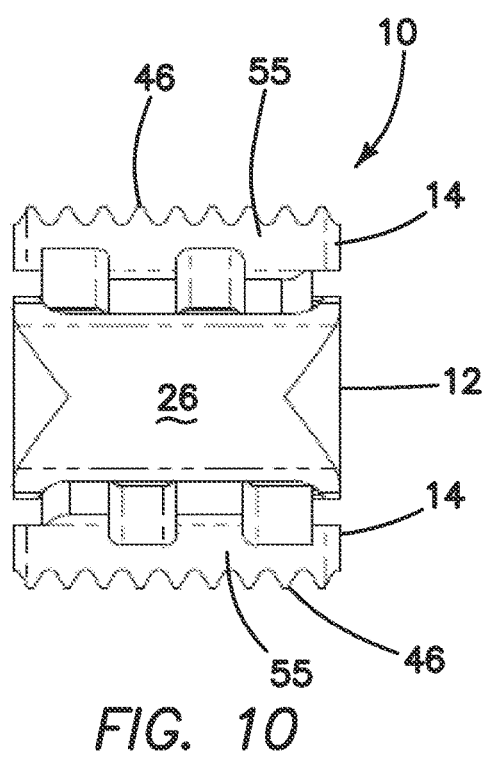
FIG. 10 is a front elevational view of the expandable interbody spacer of FIG. 2.
Figure 11:
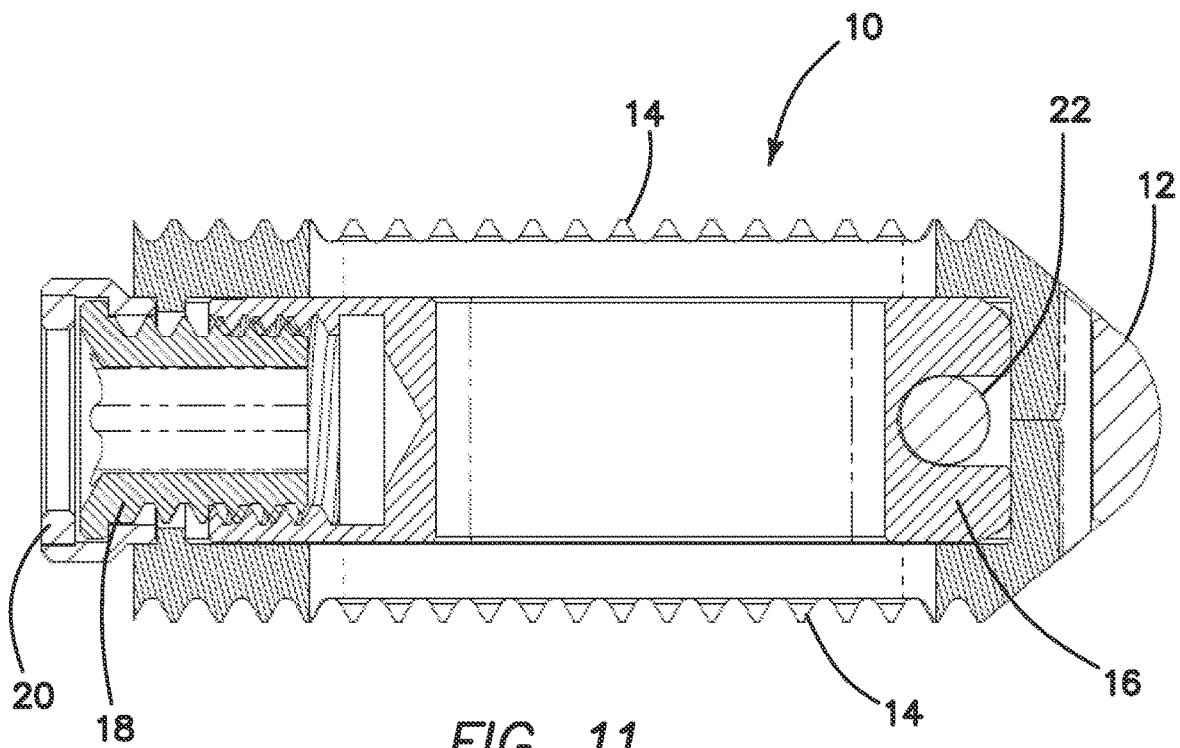
FIG. 11 is a cross-sectional view of the expandable interbody spacer of FIG. 1.
Figure 12:
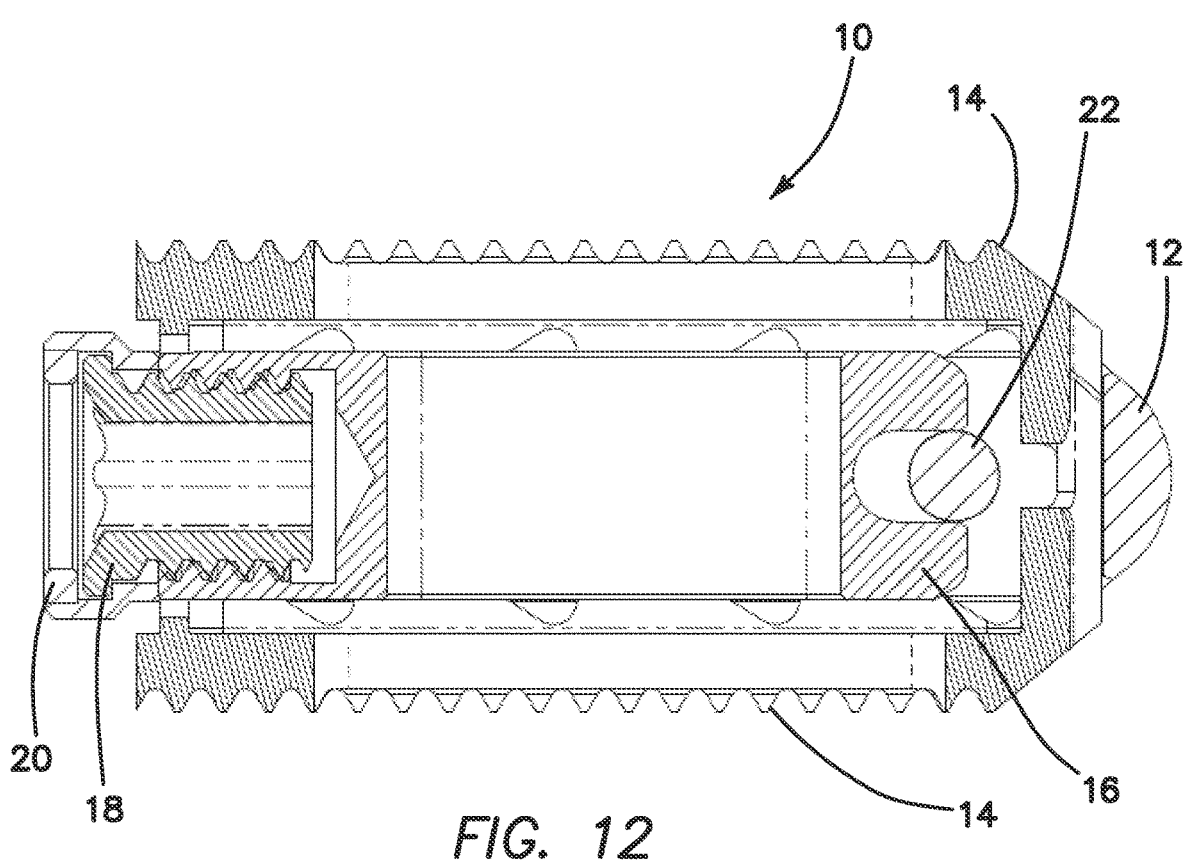
FIG. 12 is a cross-sectional view of the expandable interbody spacer of FIG. 2.
Figure 13:
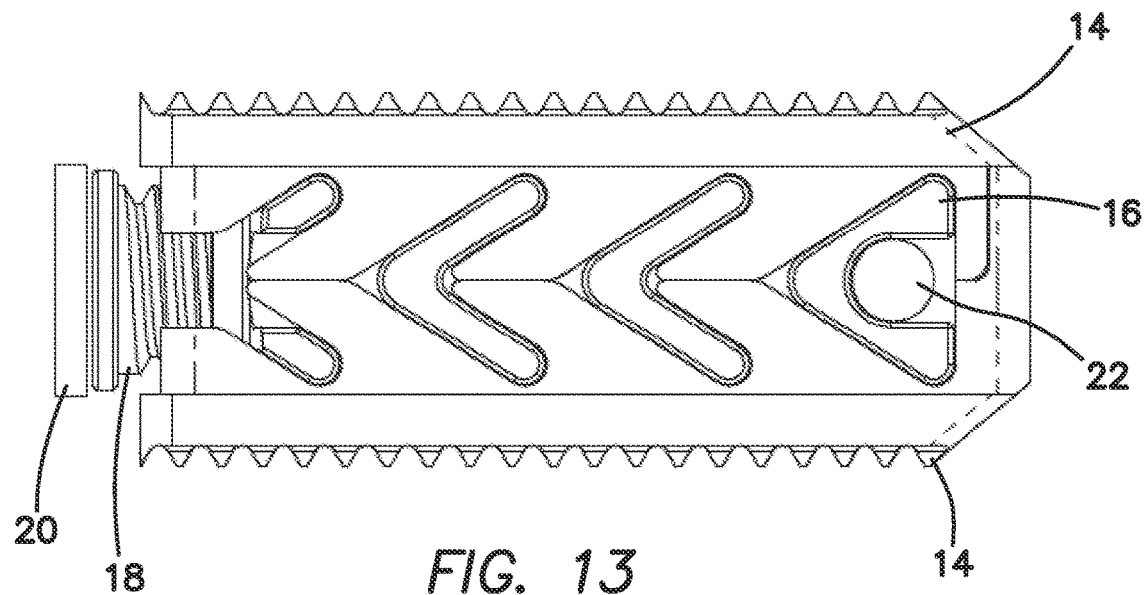
FIG. 13 is a side elevational view of the expandable interbody spacer of FIG. 1 without a housing.
Figure 14:
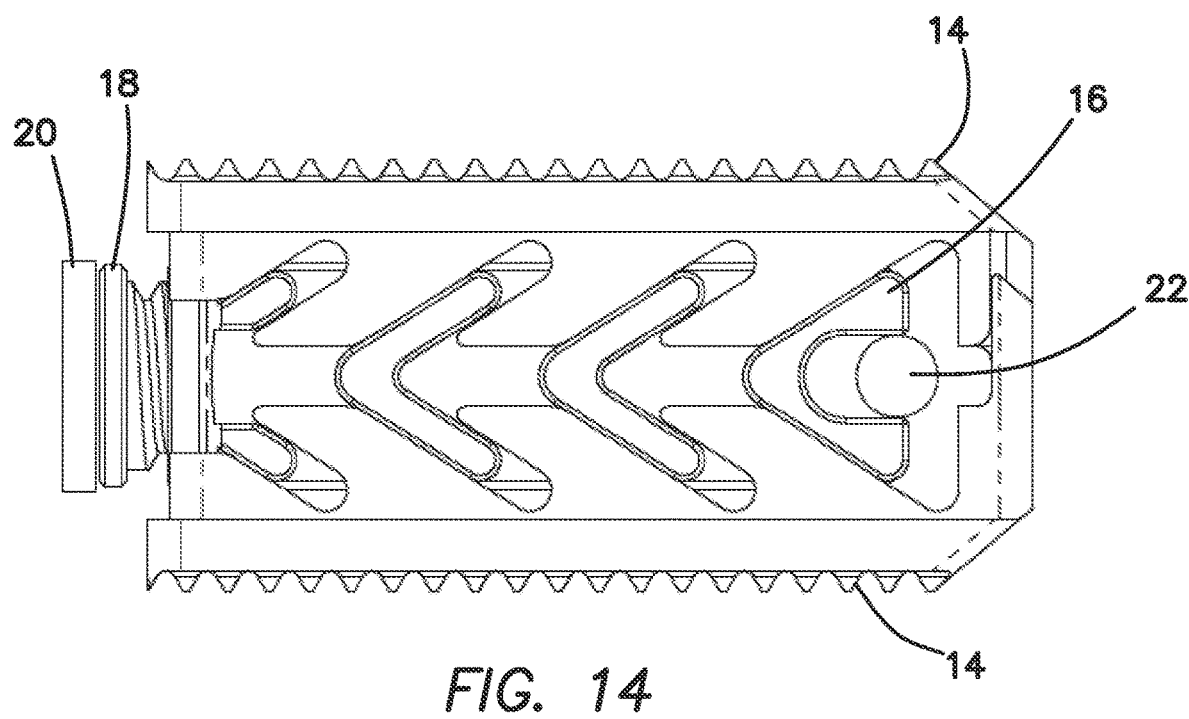
FIG. 14 is a side elevational view of the expandable interbody spacer of FIG. 2 without a housing.
Figure 83:
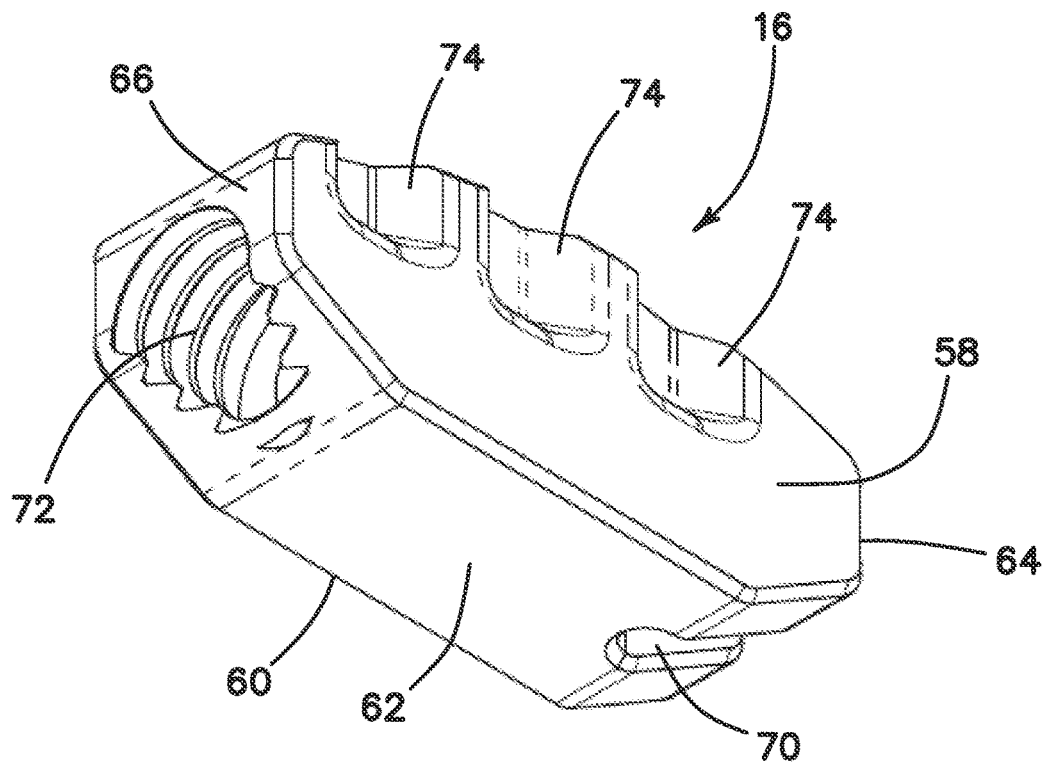
FIG. 83 is a bottom perspective view of the actuator of FIG. 80.

Turning to FIGS. 60-83, another variation of an expandable interbody spacer 10 will be described wherein like reference numbers are used to describe like parts. The expandable interbody spacer 10 comprises a housing 12, upper and lower endplates 14, an actuator 16 located inside the housing 12 and between the upper and lower endplates 14, a locking screw 18 connected to the housing 12 by a locking ring 20 and configured to move the actuator 16, an alignment pin 22 connected to the housing 12 to guide the actuator 16, and two pivot pins 23 connected to the housing 12 about which the endplates 14 pivot. The expandable interbody spacer 10 is insertable into the disc space between two adjacent vertebral bodies from a posterior approach while in an unexpanded state. The unexpanded state is illustrated in FIGS. 60, 62, 64, 66, 68 and 70. Once inserted and properly positioned inside the disc space, both upper and lower endplates 14 are expanded laterally angularly with respect to the housing 12 such that the height along one longitudinal side of the expandable spacer 10 increases relative to the other side of the spacer 10. Expansion is effected by rotating the locking screw 18 with an instrument. Rotation of the locking screw 18 moves the actuator 16 proximally which in turn moves the endplates 14 simultaneously into a laterally angular expanded state illustrated in FIGS. 61, 63, 65, 67, 69 and 71. The expandable interbody spacer 10 is advantageously easier to implant, does not require a stock of multiple implants of different sizes and helps create a lordotic angle in the spine in which the anterior height of the disc space is greater than the posterior height thereby restoring a more natural lordotic curvature of the particular segment of the spine. The spacer 10 of FIGS. 6-83 is shown to have a curvilinear geometry between the distal end and the proximal end that may be described as having a kidney bean-like, banana-like, crescent, curved, slightly curved, arcuate, c-like shape that facilitates contact with the cortical bone and is typical of implants used in a TLIF procedure. The shape is defined by the housing 12, endplates 14 and actuator 16. Even though a crescent-like shape of the spacer 10 is depicted, the invention is not so limited in order to effect a laterally angularly expandable spacer 10 and the mechanism herein described can be employed in a spacer 10 of any shape that is commonly employed for interbody spacers.

Figure 68:
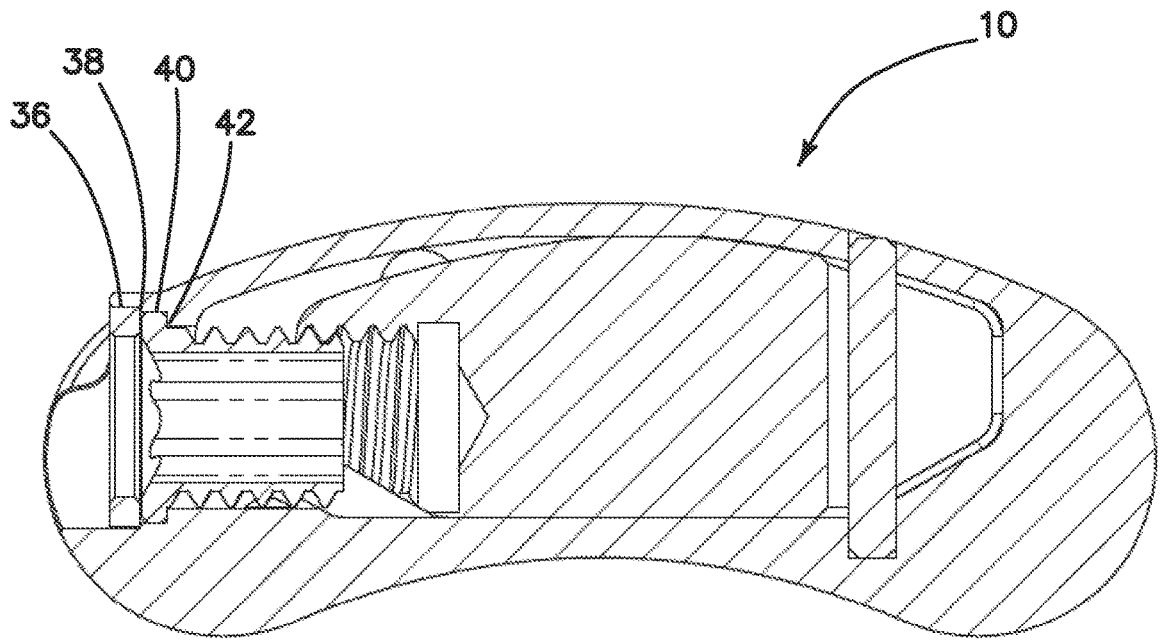
FIG. 68 is a cross-sectional view taken along line 68-68 of the expandable interbody spacer of FIG. 66.
Figure 69:
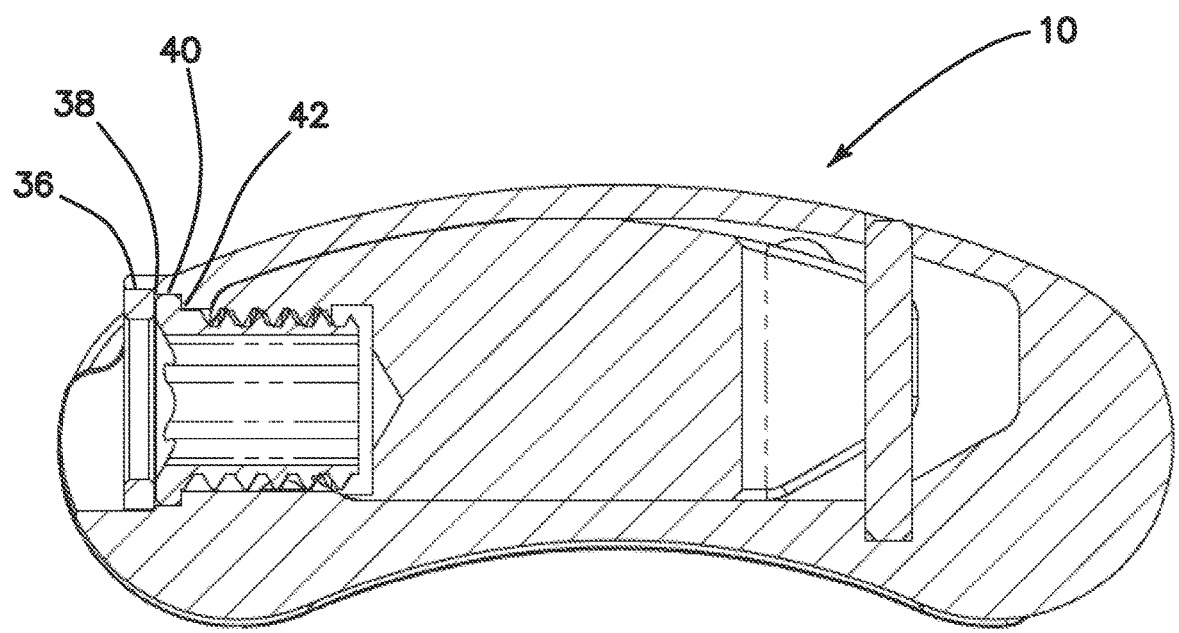
FIG. 69 is a cross-sectional view taken along line 69-69 of the expandable interbody spacer of FIG. 67.
Figure 70:
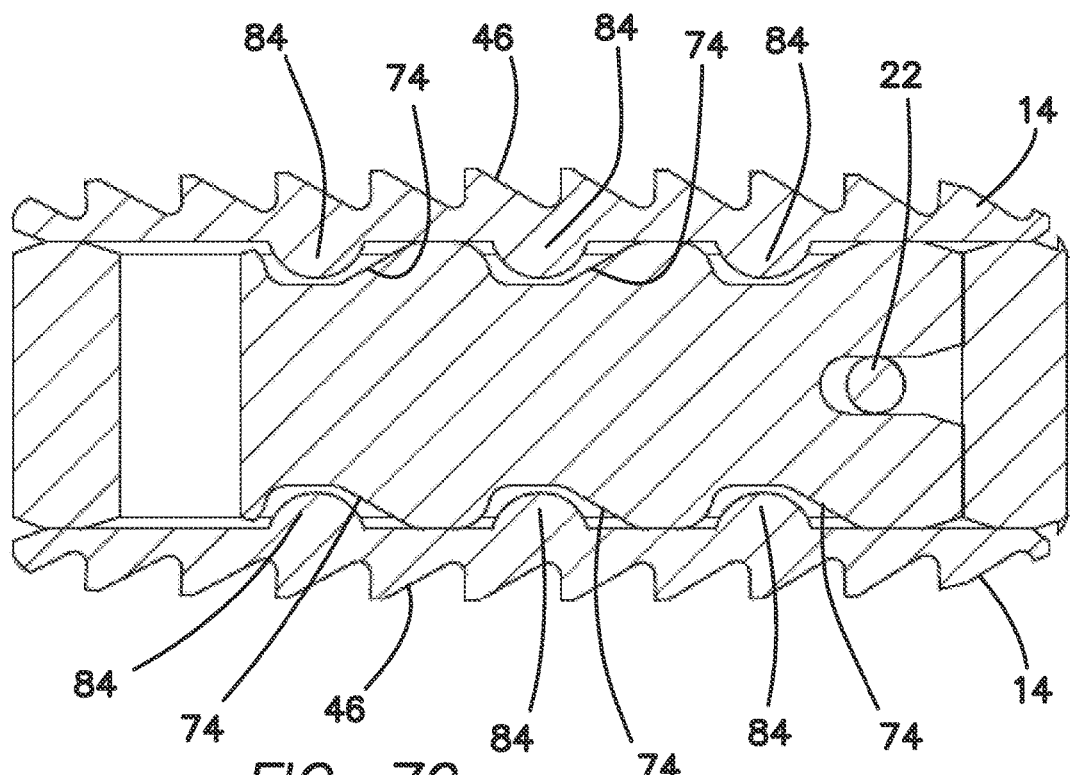
FIG. 70 is a cross-sectional view of the expandable interbody spacer of FIG. 60.
Figure 71:
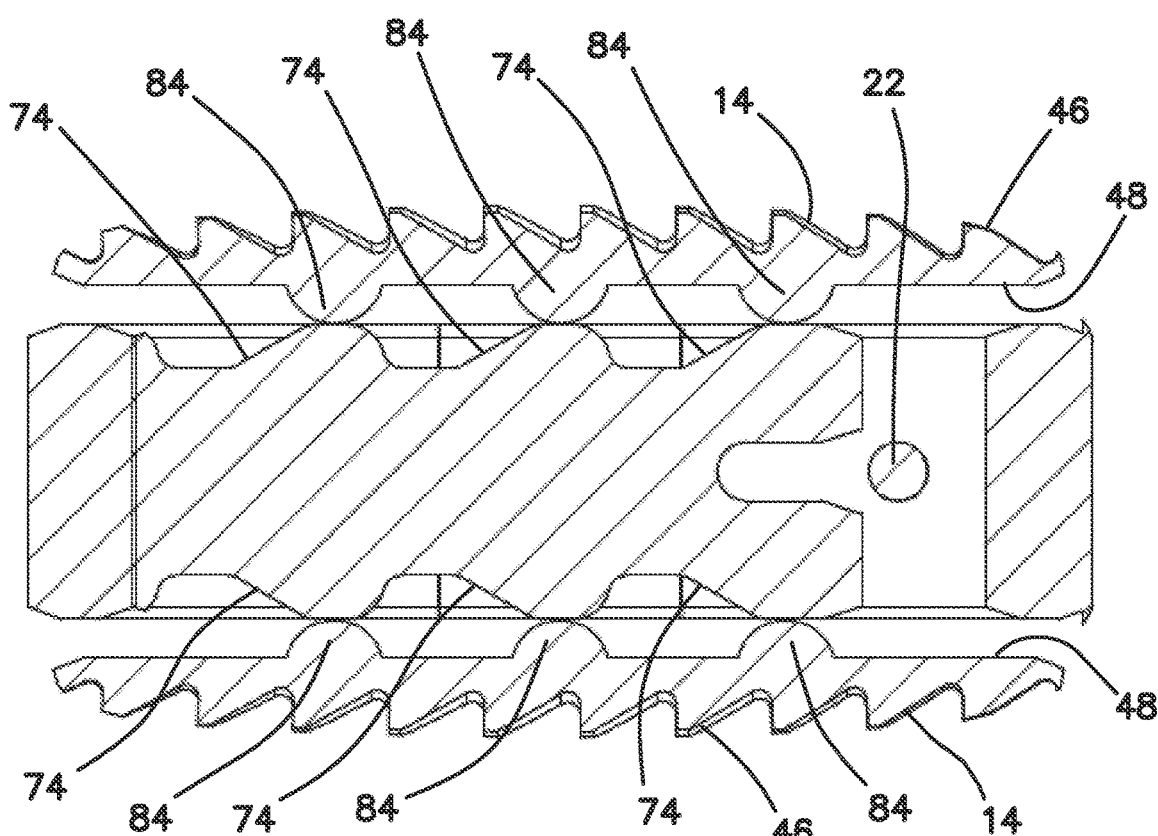
FIG. 71 is a cross-sectional view of the expandable interbody spacer of FIG. 61.
Figure 74:
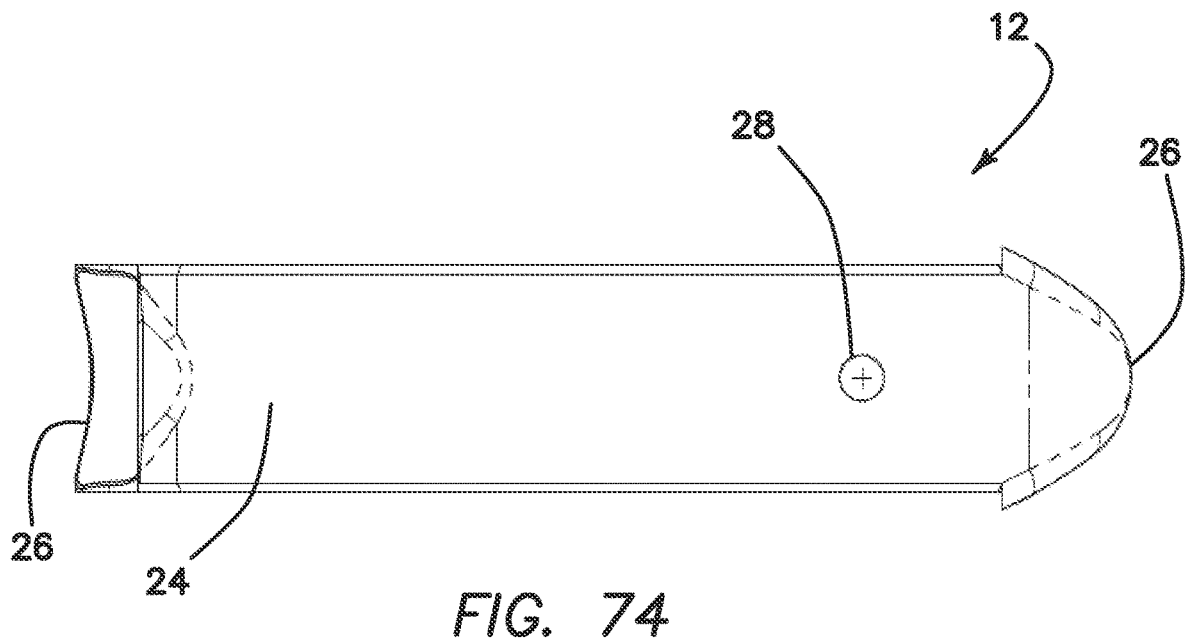
FIG. 74 is a side elevational view of the housing of FIG. 72.
Figure 75:
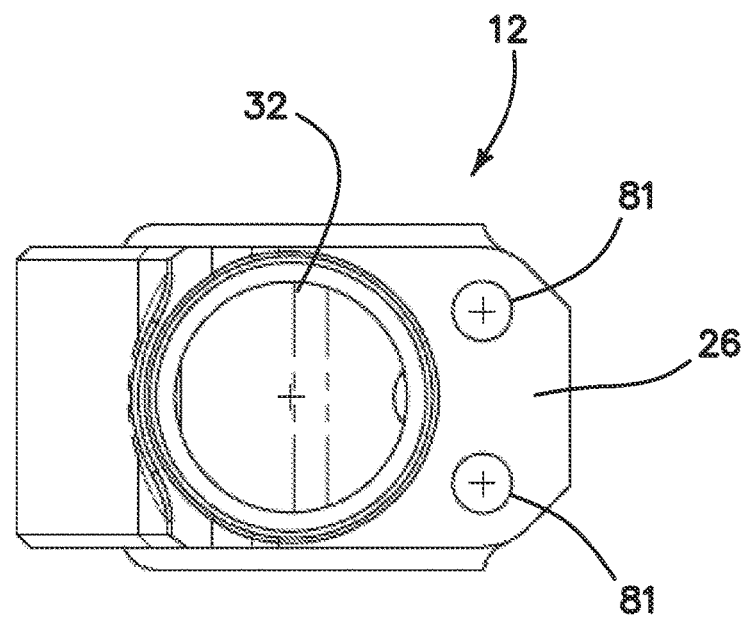
FIG. 75 is a rear elevational view of the housing of FIG. 72.
Figure 76:
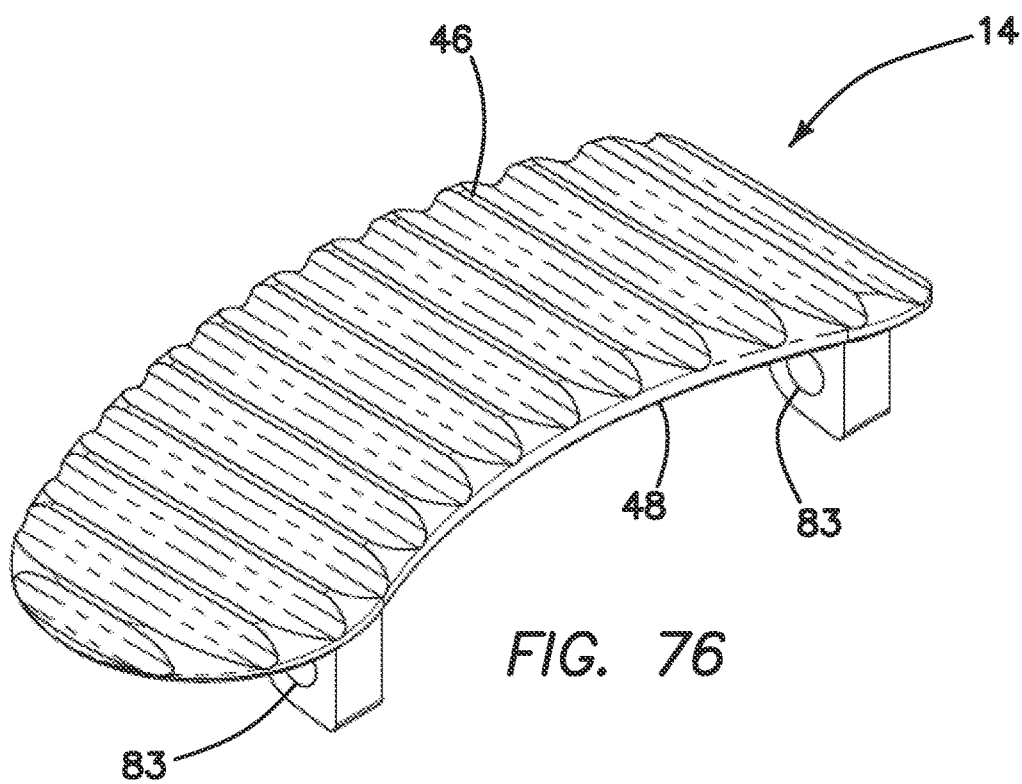
FIG. 76 is a top perspective view of an endplate of the expandable interbody spacer of FIG. 60.
Figure 77:
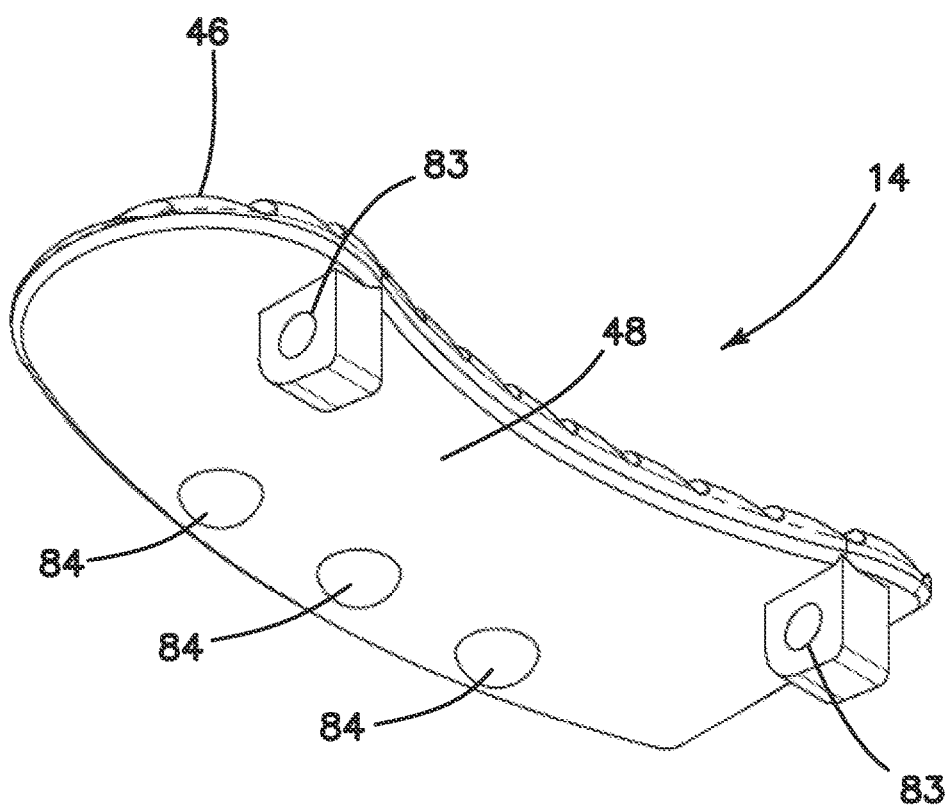
FIG. 77 is a bottom perspective view of the endplate of FIG. 76.
Figure 78:
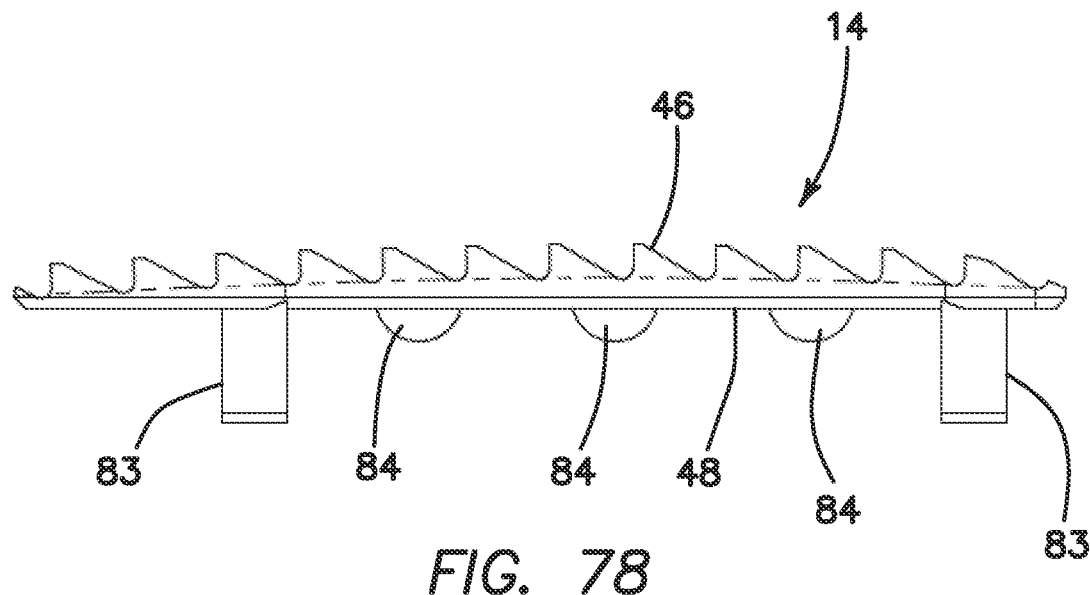
FIG. 78 is a side elevational view of the endplate of FIG. 76.
Figure 79:
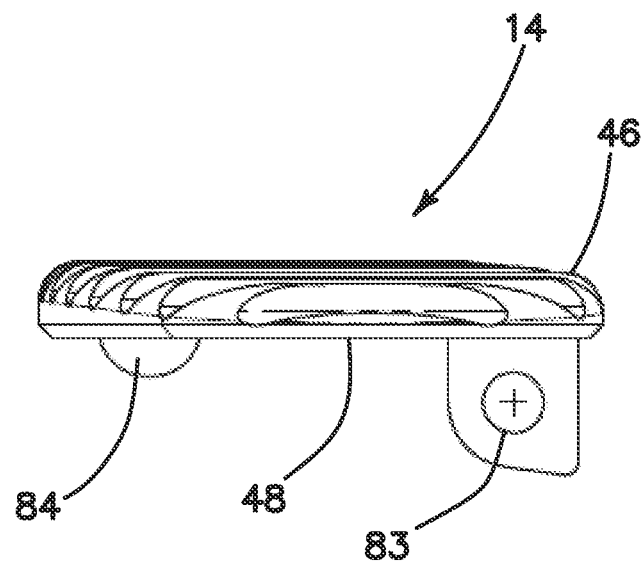
FIG. 79 is an end elevational view of the endplate of FIG. 76.
Figure 80:
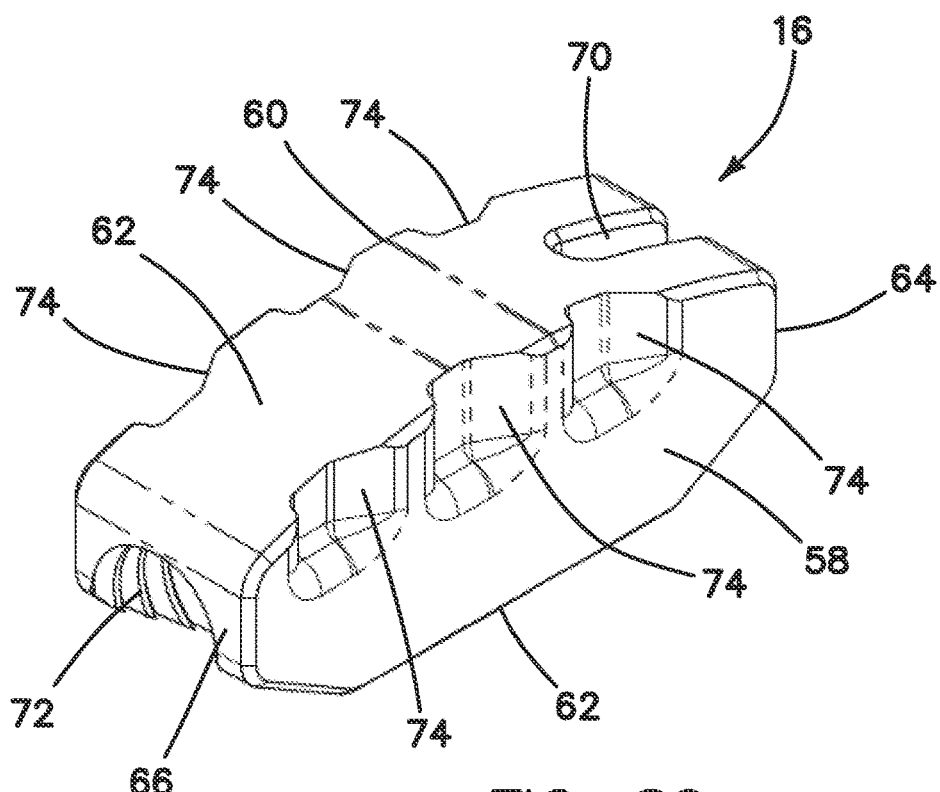
FIG. 80 is a rear top perspective view of an actuator of the expandable interbody spacer of FIG. 60.
Figure 81:
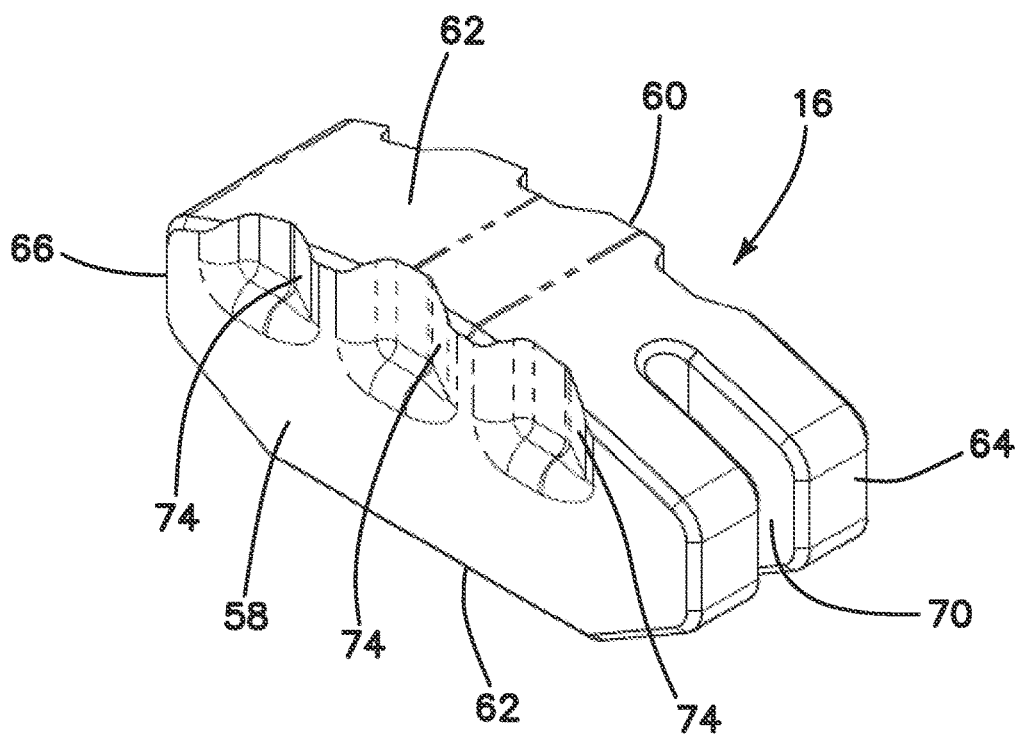
FIG. 81 is a front top perspective view of the actuator of FIG. 80.
Figure 82:
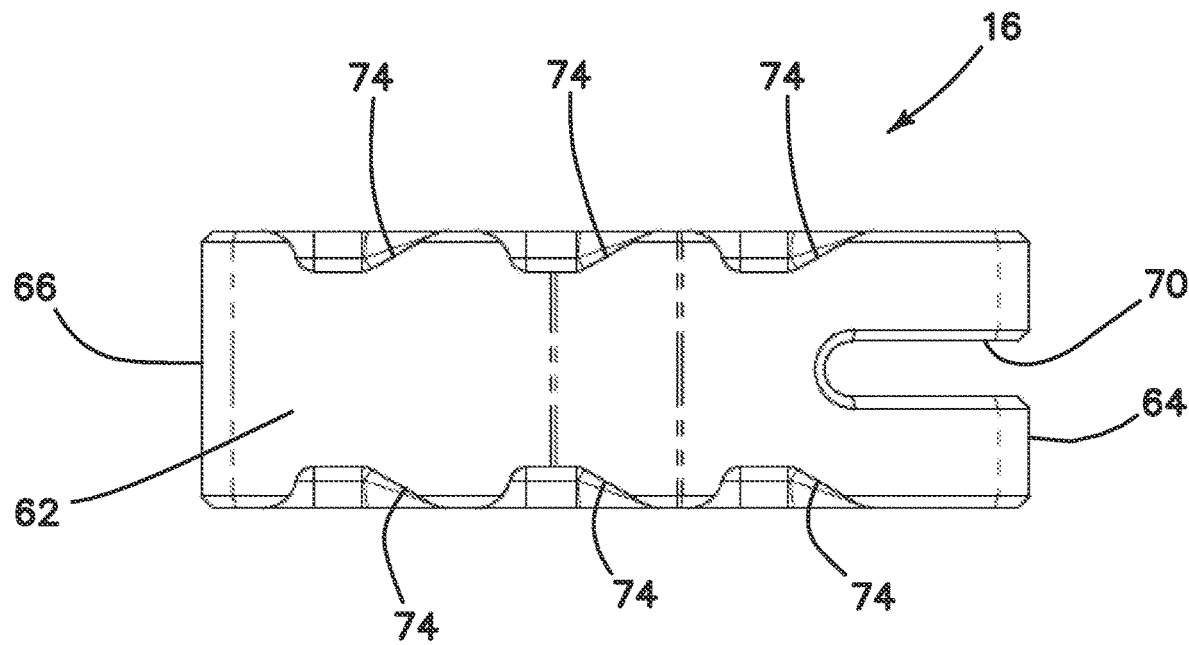
FIG. 82 is a top view of the actuator of FIG. 80.

Turning now to the FIGS. 72-75, the housing 12 will now be described in greater detail. The housing 12 includes two opposite sidewalls 24 interconnected by two opposite endwalls 26 that together define an interior of the housing 12. The sidewalls 24 of the housing 12 are bowed in a parallel fashion with one sidewall 24 having a concave outer surface and the opposite sidewall 24 having a convex outer surface interconnected by generally curved endwalls 26. The distal endwall 26 is curved outwardly and defines a peak-like tip. The proximal endwall 26 is also curved and includes a recess where the rear opening 32 is located. The rear opening 32 opens to the interior of the housing 12. The housing 12 defines a curved interior for receiving a similarly-curved actuator 16 through the open top or bottom of the housing 12. Each of the two sidewalls 24 includes an aperture 28 oppositely disposed from each other near the distal end of the housing 12 and sized and configured for receiving therethrough the alignment pin 22 of FIG. 25. A first pair of apertures 81 extend along the longitudinal axis on one side of the housing 12 near the top end and a second pair of apertures 81 extend along the longitudinal axis parallel to the first pair of apertures 81 near the bottom end of the housing 12. Each of these four pivot pin apertures 81 are sized and configured to receive four pivot pins 23. The pivot pin apertures 81 intersect with eyelet receiving locations 86 that are sized and configured to receive the eyelets 83 of the top and bottom endplates 14. The top endplate 14 is connected to the housing 12 via the two pivot pins 23 near the top end of the housing 12 and the bottom endplate 14 is connected to the housing via the two pivot pins 23 near the bottom end of the housing 12. The top and bottom endplates 14 angulate about their respect pivot pins 23 in moving between the low-profile configuration and the high-profile configuration. The housing 12 has a central opening extending between an open top end and open bottom end. The top end and the bottom end are parallel to each other. The proximal end of the housing 12 defines a first recess 36 for receiving the locking ring 20 of FIG. 24. The first recess 36 may include a first ledge 38 to provide a stop for the locking ring 20 when connected to the housing 12. The inner surface of the opening 32 also includes a second recess 40. The second recess 40 is sized and configured to receive the proximal end or head of the locking screw 18. The second recess 40 may include a second ledge 42 such that the proximal end of the locking screw 18 is retained in the second recess 40 between the second ledge 42 at the distal end and first ledge 38 and the locking ring 20 at the proximal end such that the locking screw 18 is permitted to rotate with respect to the housing 12 without translating with respect to the housing 12 or falling out of the housing 12. The recesses 36, 40 and ledges 38, 42 are also shown in FIGS. 68-69.

Turning now to FIGS. 76-79, the top and bottom endplates 14 will now be described. The top and bottom endplates 14 are identical and are connected to the housing 12 via the actuator 16. Each endplate 14 has a bone-engaging surface 46 and an interior surface 48. The bone-engaging surface 46 includes a plurality of tooth-like ridges. The ridges have pointed peaks to engage and increase the purchase on the adjacent vertebra between which the implant is located. The ridges may further be angled to help hold and prevent migration of the spacer 10 relative to the adjacent vertebrae when implanted within the intervertebral space. The spacer 10 is shown without an endplate opening; however, one may be included for the insertion of bone graft material. The endplates 14 have a width that is equal to the overall width of the spacer 10 and equal to the width of the housing 12. The sides of the endplate 14 are curved giving the endplates 14 a crescent-like shape that corresponds to the curved shape of the housing 12. One side of each endplate 14 is concave and the opposite side is convex and substantially parallel to each other. The proximal end is straight and the distal end is curved to conform to the curved penetrating distal end of the housing 12. The interior surface of the endplates 14 includes two holes 83 extending outwardly from the interior surface. The eyelets 83 are aligned with each other and sized and configured to receive a pivot pin 23 that anchors the endplate 14 to the housing 12. The endplates 14 are configured to angulate about the pivot pin 23 when going from the low-profile configuration into an angled high-profile configuration. The eyelets 83 are located along one side of the undersurface of the endplate 14. The laterally opposite side of the undersurface is provided with a plurality of semi-spherical, protrusions 84 aligned in a row. The protrusions 84 are curved surfaces sized and configured to engage the actuator 16 as will be described in greater detail below. Three protrusions 84 are shown depending from the interior surface 48 of the endplate 14 and located on the lateral side of the spacer 10 that increases in height relative to the opposite side where the eyelets are located 83 and about which the endplates 14 angulate into a high-profile configuration from a low-profile configuration.

Turning now to FIGS. 80-83, the actuator 16 will now be described. The actuator 16 is located between the two endplates 14 and inside the interior of the housing 12. The actuator 16 includes two sidewalls 62 interconnected by a top wall 58, bottom wall 60, a front wall 64 and a back wall 66. The actuator 16 is polygonal in shape and conforms to the rectangular-like shape of the interior of the housing 12. The front wall 64 of the actuator 16 includes an alignment channel 70 sized and configured to receive the alignment pin 22. The alignment channel 70 extends along the front wall 64 and between the two sidewalls 62. The back wall 66 includes a threaded opening 72 sized and configured for threaded engagement with the locking screw 18. The top wall 58 includes at least one ramped surface 74 extending downwardly from the surface of the top wall 58. In particular, three ramped surfaces 74 are formed such that each define scallop-like indentations or recesses that are sized and configured to receive the three semi-spherical protrusions 84 of the top endplate 14 when in a low-profile configuration wherein the top endplate 14 is parallel to the top wall 58 and not angulated therewith. The bottom wall 60 includes at least one ramped surface 74 extending downwardly from the surface of the bottom wall 60. In particular, three ramped surfaces 74 are formed such that each define scallop-like indentations or recesses that are sized and configured to receive the three semi-spherical protrusions 84 of the bottom endplate 14 when in a low-profile configuration wherein the bottom endplate 14 is parallel to the bottom wall 60 and not angulated therewith. The ramped surfaces 74 are formed into the top and bottom walls 58, 60 and into the sidewall 62 that is adjacent to the outwardly convex sidewall 24 of the housing 12.

The expandable interbody spacer 10 of FIGS. 60-83 is assembled by inserting the actuator 16 into the interior of the housing 12. An alignment pin 22 is inserted through the alignment pin aperture 28 of the housing 12 to secure the actuator 16 to the housing 12. The eyelets 83 of the endplates 14 are inserted into the eyelet receiving locations 86 of the housing 12 and four pivot pins 23 are inserted through the four pivot pin apertures 81 of the housing 12 and through the four eyelet holes 83 of the top and bottom endplates 14 to secure the endplates 14 to the housing 12. The semi-spherical protrusions 84 of the endplates 14 are located within the scalloped recesses that form the ramped surfaces 74. The locking screw 18 is inserted through the rear opening 32 of the housing 12 and into the threaded opening 72 of the actuator 16. The locking ring 20 is inserted in through the rear opening 32 of the housing 12 and welded thereto where it prevents the locking screw 28 from backing out of the housing 12.

In use, the present expandable interbody spacer 10 is inserted into the disc space between adjacent vertebral bodies as described above with respect to the other expandable interbody spacers 10. The spacers 10 of FIGS. 38-59 are generally configured for use as a TLIF cage in spinal surgical procedures. Similarly, as described above, an insertion instrument is connected at the proximal end of the spacer 10. The insertion instrument includes a drive mechanism that is configured to engage the socket 45 of the locking screw 18. The surgeon uses the insertion instrument to grasp the spacer 10 and place it at the mouth of the intervertebral space in its low-profile configuration. The spacer 10 is moved and orientated into its proper position within the intervertebral space. The spacer 10 is placed such that the top endplate 14 contacts the lower endplate of the upper vertebral body and the bottom endplate 14 of the spacer 10 contacts the upper endplate of the lower vertebral body on either side of the target intervertebral space. When the spacer 10 is in position, the insertion instrument is used to deploy the spacer 10 into its expanded or high-profile configuration. The insertion instrument is configured to rotate the locking screw 18 in one of a first clockwise or counter-clockwise direction. Rotation of the locking screw 18 in a first direction results in translation of the actuator 16 in a proximal direction relative to the housing 12 as can be seen in FIGS. 68-69 and in FIGS. 70-71. Other than rotation about its longitudinal axis, the locking screw 18 remains stationary with respect to the housing 12. As the actuator 16 moves proximally relative to the housing 12, the semi-spherical protrusions 84 slide against the ramped surfaces 74 of the endplates 14 moving both the top and bottom endplates 14 up relative to the ramps 74 and outwardly into angular expansion that is proportional to the degree of rotation of the locking screw 18. In the high-profile configuration, the semi-spherical protrusions 84 of the top endplate 14 rest against the top wall 58 of the actuator 16 and semi-spherical protrusions 84 of the bottom endplate 14 rest against the bottom wall 60 of the actuator 16. Angular expansion is achieved because a first side of the endplates 14 are pinned with the pivot pin 23 forcing angulation of the endplates 14 about the pivot pin 23. Along the convex side of the housing 12, the spacer 10 increases in height as the endplates 14 simultaneously angulate into the high-profile configuration along that side. The angular expansion aids in restoring the natural lordotic curvature of the spine segment. The degree of angulation of each endplate is approximately between zero and 30 degrees. Similar to the spacers 10 described above, the longitudinal length of the spacer 10 remains the same before expansion and after expansion and, therefore, does not result in the locking screw 18 protruding outwardly beyond the perimetrical footprint in the longitudinal direction of the spacer 10 and potentially impinging on surrounding tissue or interfering spatially with bone ingrowth around the spacer 10. Advantageously, the spacer 10 does not change in length or width. After the spacer 10 is properly positioned, the insertion instrument is detached and removed from the operating field. Also, advantageously, the spacer 10 of the present invention angulates uniformly, simultaneously and bilaterally along the longitudinal direction.

It is understood that various modifications may be made to the embodiments of the interbody spacer disclosed herein. Therefore, the above description should not be construed as limiting, but merely as exemplifications of preferred embodiments. Those skilled in the art will envision other modifications within the scope and spirit of the present disclosure.

We claim:

1. An expandable interbody spacer for a spine, comprising:

a housing having two sides interconnected by a distal endwall and a proximal endwall defining a hollow interior; the proximal endwall having a rear opening;
a top endplate and a bottom endplate each having a bone-engaging surface and an interior surface opposite to the bone-engaging surface and at least two oppositely disposed angled ramps extending from the interior surface;
an actuator located within the hollow interior of the housing and between the interior surfaces of the top endplate and the bottom endplate; the actuator having a top wall and a bottom wall interconnected by a distal wall and a proximal wall and a first sidewall and a second sidewall; the actuator having at least one driving surface formed in the first sidewall and at least one driving surface formed in the second sidewall; the driving surfaces being configured to mate in relative sliding engagement with the angled ramps of the top and bottom endplates; the actuator including a threaded opening formed in the proximal wall and aligned with the rear opening of the housing;
a locking screw threadingly connected to the threaded opening of the actuator and connected to the housing such that the locking screw rotates and does not translate longitudinally relative to the housing;
wherein rotation of the locking screw in a first direction translates the actuator relative to the housing to slide the driving surfaces along the angled ramps and move the top endplate and the bottom endplate outwardly away from the housing from a low-profile configuration into a high-profile configuration, wherein the distance between the top endplate and bottom endplate is greater in the high-profile configuration.

2. The expandable interbody spacer of claim 1 wherein the housing further includes an opening extending from a top to a bottom of the housing and each of the top endplate and the bottom endplate includes an endplate opening extending between the bone-engaging surface and the interior surface; the endplate openings being in communication with the actuator opening.

3. The expandable interbody spacer of claim 1 wherein the at least one driving surface formed in the first sidewall is configured to engage the angled ramps of both the top endplate and the bottom endplate and the at least one driving surface formed in the second sidewall is configured to engage the angled ramps of both the top endplate and bottom endplate.

4. The expandable interbody spacer of claim 3 wherein the driving surfaces are angled ramped surfaces interconnected to form a V-shape.

5. The expandable interbody spacer of claim 1 wherein rotation of the locking screw in a second direction opposite to the first direction translates the actuator relative to the housing and moves the top endplate and the bottom endplate inwardly toward the housing from the high-profile configuration into the low-profile configuration.

6. The expandable interbody spacer of claim 1 wherein the distal wall of the actuator includes an alignment channel configured to receive an alignment pin connected to and extending between the two sides of the housing.

7. The expandable interbody spacer of claim 1 wherein the bone-engaging surface of the top endplate and bottom endplate is angled such that a height of a distal end of the spacer is greater relative to a proximal end of the spacer in both the low-profile and high-profile configurations.

8. The expandable interbody spacer of claim 1 wherein the top endplate is parallel to the bottom endplate in the low-profile and high-profile configurations.

9. An expandable interbody spacer for a spine, comprising:
- a housing having two sides interconnected by a distal endwall and a proximal endwall defining a hollow interior; the proximal endwall having a rear opening;
- a top endplate and a bottom endplate each having a bone-engaging surface and an interior surface opposite to the bone-engaging surface and at least two oppositely disposed angled ramps extending from the interior surface and at least two oppositely disposed eyelets extending from the interior surface; each eyelet defining a pivot pin opening;
- an actuator located within the hollow interior of the housing and between the interior surfaces of the top endplate and the bottom endplate; the actuator having a top wall and a bottom wall interconnected by a distal wall and a proximal wall and a first sidewall and a second sidewall; the actuator having at least one driving surface formed in the first sidewall and at least one driving surface formed in the second sidewall; the driving surfaces being configured to mate in relative sliding engagement with the angled ramps of the top and bottom endplates; the actuator including a threaded opening formed in the proximal wall and aligned with the rear opening of the housing; the actuator including a pivot slot aligned with the pivot pin openings and extending between the first sidewall and the second sidewall;
- a locking screw threadingly connected to the threaded opening of the actuator and connected to the housing such that the locking screw rotates and does not translate longitudinally relative to the housing;
- a pivot pin extending through the pivot slot of the actuator and the pivot pin openings of the top endplate and bottom endplate;
- wherein rotation of the locking screw in a first direction translates the actuator relative to the housing to slide the driving surfaces along the angled ramps and move the top endplate and the bottom endplate outwardly away from the housing from a low-profile configuration into a high-profile configuration, wherein a distance between the top endplate and the bottom endplate at a distal end of the spacer is greater than a distance between the top and bottom endplates at a proximal end of the spacer in the high-profile configuration.

10. The expandable interbody spacer of claim 9 wherein the driving surfaces are cylindrical protrusions.

11. The expandable interbody spacer of claim 9 wherein rotation of the locking screw in the first direction causes the top endplate and the bottom endplate to angulate about the pivot pin from the low-profile configuration to the high-profile configuration.

12. The expandable interbody spacer of claim 9 wherein the top endplate is parallel to the bottom endplate in the low-profile configuration and angled in the high-profile configuration.

13. The expandable interbody spacer of claim 9 wherein rotation of the locking screw in a second direction opposite to the first direction translates the actuator in an opposite direction relative to the housing and moves the top endplate and the bottom endplate inwardly toward the housing from the high-profile configuration into the low-profile configuration.

14. The expandable interbody spacer of claim 9 wherein the distal wall of the actuator includes an alignment channel configured to receive an alignment pin connected to and extending between the two sides of the housing.

15. An expandable interbody spacer for a spine, comprising:
- a housing having a first longitudinal sidewall oppositely disposed from a second longitudinal sidewall interconnected by a distal endwall and a proximal endwall defining a hollow interior; the proximal endwall having a rear opening;
- a top endplate and a bottom endplate each having a bone-engaging surface and an interior surface opposite to the bone-engaging surface; each interior surface having at least two protrusions adjacent a first longitudinal side near the first longitudinal sidewall;
- wherein the top endplate is pivotably connected to the housing and wherein the bottom endplate is pivotably connected to the housing;
- an actuator located within the hollow interior of the housing and between the interior surfaces of the top endplate and the bottom endplate; the actuator having a proximal end and a distal end and a top wall and a bottom wall interconnected by a distal wall and a proximal wall and a first longitudinal sidewall and a second longitudinal sidewall; the top wall of the actuator having at least two driving surfaces near the first longitudinal sidewall sized and configured to engage the at least two protrusions of the top endplate; the bottom wall of the actuator having at least two driving surfaces near their first longitudinal side sized and configured to engage the at least two protrusions of the bottom endplate; the actuator having a threaded opening formed in the proximal wall that is aligned with the rear opening of the housing;
- a locking screw threadingly connected to the threaded opening of the actuator and connected to the housing such that the locking screw does not translate longitudinally relative to the housing;
- wherein rotation of the locking screw in a first direction translates the actuator relative to the top and bottom endplates and pivots the top and bottom endplates into angulation from a low-profile configuration to a high-profile configuration, wherein the distance between the top and bottom endplates adjacent the first longitudinal sidewall is greater than the distance between the top and bottom endplates adjacent the second longitudinal sidewall when the spacer is in the high-profile configuration.

16. The expandable interbody spacer of claim 15 wherein the driving surfaces of the actuator are ramped surfaces.

17. The expandable interbody spacer of claim 15 wherein rotation of the locking screw in a second direction opposite to the first direction translates the actuator relative to the top and bottom endplates and pivots the top and bottom endplates from the high-profile configuration to the low-profile configuration.

18. The expandable interbody spacer of claim 15 wherein the protrusions of the top and bottom endplates are semispherical in shape.

19. The expandable interbody spacer of claim 15 wherein the driving surfaces of the top wall are recessed relative to the top wall and the driving surfaces of the bottom wall are recessed relative to the bottom wall.

20. The expandable interbody spacer of claim 19 wherein in the low-profile configuration the protrusions of the top endplate are located in the recessed driving surfaces of the top wall and the protrusions of the bottom wall are located in the recessed driving surfaces of the bottom wall and in the high-profile configuration, wherein the protrusions of the top endplate are in contact with unrecessed portions of the top wall and the protrusions of the bottom wall are in contact with unrecessed portions of the bottom wall.

\* \* \* \* \*